(12) United States Patent
Wagner, Jr. et al.

(10) Patent No.: US 12,048,734 B2
(45) Date of Patent: Jul. 30, 2024

(54) BIOACTIVE PEPTIDES AND METHODS OF USE THEREOF

(71) Applicant: OP-T LLC, Denver, CO (US)

(72) Inventors: David H. Wagner, Jr., Denver, CO (US); Gisela M. Vaitaitis, Centennial, CO (US); Charles W. Henry, Denver, CO (US); Martin G. Yussman, Denver, CO (US)

(73) Assignee: OP-T LLC, Aurora, CO (US)

( * ) Notice: Subject to any disclaimer, the term of this patent is extended or adjusted under 35 U.S.C. 154(b) by 416 days.

(21) Appl. No.: 17/233,141

(22) Filed: Apr. 16, 2021

(65) Prior Publication Data

US 2022/0000979 A1  Jan. 6, 2022

Related U.S. Application Data

(60) Provisional application No. 63/031,192, filed on May 28, 2020, provisional application No. 63/011,921, filed on Apr. 17, 2020.

(51) Int. Cl.
| | | |
|---|---|---|
| A61K 38/17 | (2006.01) | |
| A61K 38/08 | (2019.01) | |
| A61K 38/10 | (2006.01) | |
| A61K 38/19 | (2006.01) | |
| A61K 47/60 | (2017.01) | |
| A61K 47/68 | (2017.01) | |
| A61P 31/14 | (2006.01) | |
| A61P 37/06 | (2006.01) | |

(52) U.S. Cl.
CPC ............ *A61K 38/191* (2013.01); *A61K 47/60* (2017.08); *A61K 47/6811* (2017.08); *A61P 31/14* (2018.01); *A61P 37/06* (2018.01)

(58) Field of Classification Search
CPC .... A61K 38/08; A61K 38/10; A61K 38/1793; A61K 47/62; A61K 47/60
See application file for complete search history.

(56) References Cited

U.S. PATENT DOCUMENTS

| | | |
|---|---|---|
| 4,642,295 A | 2/1987 | Baker |
| 6,264,951 B1 | 7/2001 | Armitage |
| 6,319,671 B1 | 11/2001 | U'ren et al. |
| 6,812,203 B1 | 11/2004 | Pype et al. |
| 7,087,573 B1 | 8/2006 | Lazarus |
| 7,098,322 B2 | 8/2006 | Pype et al. |
| 7,189,518 B2 | 3/2007 | Schonbeck et al. |
| 7,601,335 B2 | 10/2009 | McCutcheon et al. |
| 7,741,280 B2 | 6/2010 | Guichard et al. |
| 8,476,008 B2 | 7/2013 | Nagalla et al. |
| 9,409,987 B2 | 8/2016 | Toporik et al. |
| 9,562,088 B2 | 2/2017 | Wagner |
| 10,882,911 B2 | 1/2021 | Park et al. |
| 11,130,795 B2 | 9/2021 | Wagner |
| 11,793,854 B2 | 10/2023 | Wagner, Jr. et al. |
| 2003/0078269 A1 | 4/2003 | Pearson et al. |
| 2004/0072750 A1 | 4/2004 | Phillips et al. |
| 2005/0101769 A1 | 5/2005 | Pype et al. |
| 2005/0202531 A1 | 9/2005 | Toporik |
| 2006/0234316 A1 | 10/2006 | Wagner |
| 2007/0041971 A1 | 2/2007 | Wagner |
| 2007/0243259 A1 | 10/2007 | Sung et al. |
| 2008/0050369 A1 | 2/2008 | Yellin et al. |
| 2008/0058360 A1 | 3/2008 | Schonbeck et al. |
| 2010/0062471 A1 | 3/2010 | Kantor et al. |
| 2010/0172869 A1 | 7/2010 | Masuoka |
| 2011/0177556 A1 | 7/2011 | Prussak et al. |
| 2011/0178000 A1 | 7/2011 | Freyberg et al. |
| 2011/0229495 A1 | 9/2011 | Wagner |
| 2012/0282291 A1 | 11/2012 | Berghman et al. |
| 2013/0203719 A1 | 8/2013 | Kalergis et al. |
| 2013/0209463 A1 | 8/2013 | Rotman et al. |
| 2013/0236495 A1 | 9/2013 | Wagner |
| 2013/0306034 A1 | 11/2013 | Hamedovic et al. |
| 2014/0044641 A1 | 2/2014 | Toporik et al. |
| 2014/0135684 A1 | 5/2014 | Kuo et al. |
| 2014/0170141 A1 | 6/2014 | Toporik et al. |
| 2015/0366946 A1 | 12/2015 | Vol et al. |
| 2016/0200823 A1 | 7/2016 | Burkly et al. |
| 2016/0296609 A1 | 10/2016 | Oh et al. |
| 2016/0347816 A1 | 12/2016 | Toporik et al. |
| 2016/0356771 A1 | 12/2016 | Smith et al. |
| 2017/0108514 A1 | 4/2017 | Wagner |
| 2017/0232062 A1 | 8/2017 | Rotman et al. |
| 2017/0306034 A1 | 10/2017 | Honczarenko et al. |
| 2017/0319671 A1 | 11/2017 | Faulkner et al. |
| 2017/0355747 A1 | 12/2017 | Wagner |
| 2018/0194829 A1 | 7/2018 | Toporik et al. |

(Continued)

FOREIGN PATENT DOCUMENTS

| | | |
|---|---|---|
| WO | WO-1999/011263 A1 | 3/1999 |
| WO | WO-2005/006949 A2 | 1/2005 |

(Continued)

OTHER PUBLICATIONS

International Search Report and Written Opinion for International Application No. PCT/US2021/027749 dated Oct. 11, 2021.
Invitation to Pay Additional Fees for International Application No. PCT/US2021/027749 dated Aug. 18, 2021.
Vaitaitis et al., "A CD40 targeting peptide prevents severe symptoms in experimental autoimmune encephalomyelitis," Journal of Neuroimmunology, 332: 8-15 (2019).
Vaitaitis et al., "A CD40-targeted peptide controls and reverses type 1 diabetes in NOD mice," Diabetologia, 57: 2366-2373 (2014).

(Continued)

*Primary Examiner* — Barry A Chestnut
(74) *Attorney, Agent, or Firm* — Foley Hoag LLP; Brendan T. Jones; David E. Shore

(57) ABSTRACT

Methods and compositions are disclosed for treating and preventing cytokine release syndrome (CRS), acute respiratory distress syndrome (CRS), and alveolar capillary injury (ACI) in a subject.

14 Claims, 23 Drawing Sheets

Specification includes a Sequence Listing.

(56) References Cited

U.S. PATENT DOCUMENTS

| | | |
|---|---|---|
| 2018/0194847 A1 | 7/2018 | Park et al. |
| 2019/0194290 A1 | 6/2019 | Wagner, Jr. et al. |
| 2019/0231848 A1 | 8/2019 | Rotman et al. |
| 2019/0263888 A1 | 8/2019 | Wagner, Jr. et al. |
| 2020/0072837 A1 | 3/2020 | Wagner, Jr. et al. |
| 2020/0297795 A1 | 9/2020 | Wagner, Jr. et al. |
| 2020/0326333 A1 | 10/2020 | Wagner, Jr. et al. |
| 2021/0008162 A1 | 1/2021 | Wagner, Jr. et al. |
| 2021/0332104 A1 | 10/2021 | Wagner, Jr. et al. |
| 2022/0000979 A1 | 1/2022 | Wagner, Jr. et al. |
| 2022/0106381 A1 | 4/2022 | Wagner |
| 2023/0101772 A1 | 3/2023 | Wagner, Jr. et al. |
| 2024/0115651 A1 | 4/2024 | Wagner, Jr. et al. |

FOREIGN PATENT DOCUMENTS

| | | |
|---|---|---|
| WO | WO-2007/090280 A1 | 8/2007 |
| WO | WO-2008/036675 A2 | 3/2008 |
| WO | WO-2010/055510 A2 | 5/2010 |
| WO | WO-2012/054584 A2 | 4/2012 |
| WO | WO-2012/154215 A1 | 11/2012 |
| WO | WO-2015/148389 A2 | 10/2015 |
| WO | WO-2019/032945 A1 | 2/2019 |
| WO | WO-2019/094581 A1 | 5/2019 |
| WO | WO-2019/136307 A1 | 7/2019 |
| WO | WO-2020/210726 A1 | 10/2020 |
| WO | WO-2021/011437 A1 | 1/2021 |
| WO | WO-2021/212013 A2 | 10/2021 |
| WO | WO-2021/231898 A2 | 11/2021 |

OTHER PUBLICATIONS

"Society commits $19.4 Million for New MS Research Projects," National Multiple Sclerosis Society, 2013 retrieved from http://vitaminad.nositio.net/news/New_Research_Fall_2013.pdf, 28 pages.

Aart et al., Inhibition of CD40-TRAF6 interactions by the small molecule inhibitor 6877002 reduces neuroinflammation, Journal of Neuroinflammation, 14: 105-118 (2014).

Aarts et al., "The CD40-CD40L dyad in Experimental Autoimmune Encephalomyelitis and Multiple Sclerosis," Chapter 2 Front. Immunol., 8(1791): 24-45 (2017).

Abdelhak et al., "Primary Progressive Multiple Sclerosis: Putting Together the Puzzle," Frontiers in Neurology, 8:234 (2017).

Alaoui-Ismaili et al., "Design of second generation therapeutic recombinant bone morphogenetic proteins," Cytokine & Growth Factor Reviews, 20: 501-507 (2009).

Amer. Diabetes Association Diagnosis and Classification of Diabetes Mellitus, Diabetes Care, 2014, 37, Suppl.I :S8 I-S90.

Anderson et al., "Multiple sclerosis, seizures, and antiepileptics: role of IL-18, IDO, and melatonin," European Journal of Neurology, 18(5): 680-685 (2011).

Angelini et al., "Analysis of HLA DP, DQ, and DR alleles in adult Italian rheumatoid arthritis patients," Human Immunology, 34(2): 135-141 (1992).

Arbour et al., "A new clinically relevant approach to expand myelin specific T cells," Journal of Immunological Methods, 310(1-2): 53-61 (2006).

Armitage et al., "CD40L: a multi-functional ligand," Semin Immunol, 5(6): 404-412 (1993).

Armitage et al., "CD40L: a multi-functional ligand," Seminars in Immunology, 5: 401-412 (1993).

Attwood et al., "The Babel of Bioinformatics," Science, 290(5491): 471-473 (2000).

Bak et al., "Physicochemical and Formulation Developability Assessment for Therapeutic Peptide Delivery—A Primer," The AAPS Journal, 17(1): 144-155 (2015).

Baker et al., "CD40 on NOD CD4 T cells contributes to their activation and pathogenicity," Journal of Autoimmunity, 31(4): 385-392 (2008).

Balasa et al., "CD40 Ligand-CD40 Interactions Are Necessary for the Initiation of Insulitis and Diabetes in Nonobese Diabetic Mice," The Journal of Immunology, 159: 4620-4627 (1997).

Barker et al., "Prediction of Autoantibody Positivity and Progression to Type 1 Diabetes: Diabetes Autoimmunity Study in the Young (DAISY)," Journal of Clinical Endocrinology & Metabolism, 89(8):3896-3902 (2004).

Becker et al., "CD40, an extracellular receptor for binding and uptake of Hsp70-peptide complexes," The Journal of Cell Biology, 158(7): 1277-1285 (2002).

Benveniste et al., "Molecular regulation of CD40 gene expression in macrophages and microglia," Brain, Behavior, and Immunity, 18(1): 7-12 (2004).

Biosyn., "Why acetylate and amidate a peptide," accessed on Mar. 22, 2021 at <https://biosyn.com/faq/why-acetylate-and-amidate-apeptide.aspx>: 1 page (2008).

Bonifacio, "Predicting Type 1 Diabetes Using Biomarkers," Diabetes Care, 38: 989-996 (2015).

Boon et al., "Prevention of Experimental Autoimmune Encephalomyelitis in the Common Marmoset (*Allithrix jacchus*) Using a Chimeric Antagonist Monoclonal Antibody Against Human CD40 Is Associated with Altered B Cell Response," J. Immunol., 167: 2942-2949 (2001).

Bourgeois et al., "A Role for CD40 Expression on CD8+ T cells in the Generation of CD8+ T Cell Memory," Science, 297: 2060-2063 (2002).

Bowie et al., "Deciphering the Message in Protein Sequences: Tolerance to Amino Acid Substitutions," Science, 247(4948): 1306-1310 (1990).

Bretscher, "The two-signal model of lympocyte activation twenty-one years later," Immunology Today, 13(2): 74-76 (1992).

Burge et al., "The Role of a Coronary Artery Calcium Scan in Type 1 Diabetes," Diabetes Technology & Therapeutics, 18(9): 594-603 (2016).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138 (1990).

Campean et al., "CD40-CD154 expression in calcified and non-calcified coronary lesions of patients with chronic renal failure," Atherosclerosis, 190(1): 156-166 (2007).

Carter et al., "CD40 engagement of CD4+ CD40+ T cells in a neo-self antigen disease model ablates CTLA-4 expression and indirectly impacts tolerance," Eur J Immunol, 42: 424-435 (2012).

Carter et al., "CD40 engagement of CD4+CD40+ T cells in a neo-self antigen disease model ablates CTLA-4 expression and indirectly impacts tolerance," European Journal of Immunology, 42: 424-435 (2012).

Catchpole et al., "Canine diabetes mellitus: can old dogs teach US new tricks?," Diabetologia, 48: 1948-1956 (2005).

Chatzigeorgiou et al., "Blocking CD40-TRAF6 signaling is a therapeutic target in obesity-associated insulin resistance," PNAS, 111(7): 2686-2691 (2014).

Christensen et al., "Systemic Inflammation in Progressive Multiple Sclerosis Involves Follicular T-Helper, Th17- and Activated B-Cells and Correlates with Progression," PLOS ONE, 8(3): e57820 (2013).

Cipollone et al., "Enhanced soluble CD40 ligand contributes to endothelial cell dysfunction in vitro and monocyte activation in patients with diabetes mellitus: effect of improved metabolic control," Diabetologia, 48: 1216-1224 (2005).

Cooper et al., "Cutting Edge: TCR Revision Occurs in Germinal Centers," J Immunol, 73: 6532-6536 (2004).

Cooper et al., "Cutting Edge: TCR Revision Occurs in Germinal Centers," The Journal of Immunology, 173: 6532-6536 (2004).

Davidson et al., "Co-Stimulatory Blockade in the Treatment of Murine Systemic Lupus Erthematosus (SLE)," NY Acad Sci. 987: 188-198 (2003).

Davidson et al., "Co-Stimulatory Blockade in the Treatment of Murine Systemic Lupus Erythematosus," Ann. NY Acad. Sci, 987: 188-198 (2003).

(56) References Cited

OTHER PUBLICATIONS

De Ramon et al., "CD154-CD40 T-cell co-stimulation pathway is a key mechanism in kidney ischemia-reperfusion injury," Kidney International, 88(3): 538-549 (2015).
De Ramon et al., "CD154-CD40 T-cell co-stimulation pathway is a key mechanism in kidney ischemia-reperfusion injury," Kidney International, 88: 538-549 (2015).
Devaraj et al., "Increased Monocytic Activity and Biomarkers of Inflammation in Patients With Type 1 Diabetes," Diabetes, 55: 774-779 (2006).
Durie et al., "Prevention of Collagen-Induced Arthritis with an Antibody to gp39, the Ligand for CD40," Science, 261: 1328-1330 (1993).
Durie, F.H., R.A. Fava, T.M. Foy, A. Aruffo, J.A. Ledbetter, and R.J. Noelle. 1993. Science 281:1328.
Ellmark et al., "Modulation of the CD40-CD40 ligand interaction using human anti-CD40 single-chain antibody fragments obtained from the n-CoDeR phage display library," Immunology, 106: 456-463 (2002).
Ellmark et al., "Modulation or the CD40-CD40 ligand interaction using human anti-CD40 single-chain antibody fragments obtained from the n-CoDeR phage display library," Immunology, 106: 456-463 (2002).
Extended European Search Report for EP Application No. 18877124.0 dated Jul. 26, 2021.
Extended European Search Report for EP Application No. 19736089.4 dated Nov. 5, 2021.
Extended European Search Report for EP Application No. EP 11835055 dated Mar. 31, 2014.
Extended European Search Report for EP Application No. EP 18162234 dated Nov. 30, 2018.
Extended European Search Report for EP Application No. PCT/US2015/022033 dated Mar. 22, 2018.
Extended European Search Report for European Patent Application No. 15768543.9, dated Mar. 22, 2018, 6 pages.
Fanslow et al., "Recombinant CD40 Ligand Exerts Potent Biologic Effect on T Cells," Journal of Immunology, 152: 4262-4269 (1994).
Fanslow et al., "Recombinant CD40 ligand exerts potent biologic effects on T cells," J Immunol, 152(9): 4262-4269 (1994).
Final Action for U.S. Appl. No. 13/880,387, dated Feb. 18, 2016, 8 pages.
Fisniku et al., "Disability and T2 MRI lesions: a 20-year follow-up of patients with relapse onset of multiple sclerosis," Brain, 131(3): 808-817 (2008).
Fox, "Clinical features, pathogenesis, and treatment of Sjogren's syndrome," Current Opinion in Rheumatology, 8(5): 438-445 (1996) (Abstract Only).
Garlichs et al., "Upregulation of CD40 and CD40 ligand (CD154) in patients with moderate hypercholesterolemia," Circulation, 104: 2395-2400 (2001).
Gerritse et al., "CD40-CD40 ligand interactions in experimental allergic encephalomyelitis and multiple sclerosis," PNAS, 93: 2499-2504 (1996).
Girvin et al., "CD40/CD40L Interaction is Essential for the Induction of EAE in the Absence of CD28-Mediated Co-stimulation," Journal of Autoimmunity, 18(2): 83-94 (2002).
Giuliani et al., "Minocycline attenuates T cell and microglia activity to impair cytokine production in T cell-microglia interaction," Journal of Leukocyte Biology, 78: 135-143 (2005).
Goodnow et al., "Pathways for self-tolerance and the treatment of autoimmune diseases," Lancet, 357: 2115-2121 (2001).
Goodnow, "Pathways for self-tolerance and the treatment of autoimmune diseases," Lancet, 357: 2115-2121 (2001).
Gottlieb et al., "Managing feline diabetes: current perspectives," Vet Med (Auckl), 9: 33-42 (2018).
Goverman et al., "Transgenic mice that express a myelin basic protein-specific T cell receptor develop spontaneous autoimmunity," Cell, 72(4): 3018-3027 (1993).
Graber et al., "Interleukin-17 in transverse myelitis and multiple sclerosis," Journal of Neuroimmunology, 196(1-2): 124-132 (2008).
Grabstein et al., "The regulation of T cell-dependent antibody formation in vitro by CD40 ligand and IL-2," J Immunol, 150(8): 3141-3147 (1993).
Grabstein, "The Regulation or T Cell-Dependent Antibody Formation in Vitro by CD40 Liqand and IL-2," The Journal of Immunology, 150(8): 3141-3147 (1993).
Grant application entitled "Developing a small peptide to control autoimmune inflammation in type 1 diabetes" by PI: David H, Wagner and received on Sep. 2, 2016 and publicly available on Jan. 5, 2018, p. 1-46 (2018).
Grossman, "Avoiding Tolerance Against Prostatic Antigens With Subdominant Peptide Epitopes," Journal of Immunotherapy, 23(3): 237-241 (2001).
Grossman, M.E., E. Davila, and E. Celis. 2001. *J Immunother* 24:237-241.
Guo et al., "CD40L-Dependant Pathway is Active at Various Stages of Rheumatoid Arthritis Disease Progression," The Journal of Immunology,198: 4490-4501 (2017).
Guo et al., "CD40L-Dependent Pathway Is Active at Various Stages of Rheumatoid Arthritis Disease Progression," J Immunol, 198(11): 4490-4501 (2017).
Guo et al., "Protein tolerance to random amino acid change," PNAS, 101(25): 9205-9210 (2004).
Guptill, L., et al., Vet. J., 2003, 165:240-47.
Hafler et al., "Risk alleles for multiple sclerosis identified by a genomewide study," New England Journal of Medicine, 357(9): 851-862 (2007).
Hancock., "Preventing and managing diabetes: an exemplar for NCDS," C3 Collaborating for Health: pp. 1-8 (2012).
Harrington et al., "Differential tolerance is induced in T cells recognizing distinct epitopes of myelin basic protein," Immunity, 8(5): 571-580 (1998).
Hemmer et al., "New concepts in the immunopathogenesis of multiple sclerosis," Nature Reviews Neuroscience, 3(4): 291-301 (2002).
Hernandez et al., "CD40-CD40 Ligand Interaction between Dendritic Cells and CDS+ T Celis Is Needed to Stimulate Maximal T Cell Responses in the Absence of CD4+ T Cell Help," The Journal of Immunology, 178: 2844-2852 (2007).
Hernandez et al., "CD40-CD40 Ligand Interaction between Dendritic Cells and CD8+ T Cells Is Needed to Stimulate Maximal T Cell Responses in the Absence of CD4+ T Cell Help," J Immunol, 178(5) 2844-2852 (2007).
Hoffjan et al., "The genetics of multiple sclerosis: an update 2010," Molecular and Cellular Probes, 24(5): 237-243 (2010).
Homann et al., "CD40L Blockade Prevents Autoimmune Diabetes by Induction of Bitypic NK/DC Reaulatory Geils," Immunity, 16: 403-415 (2002).
Homann et al., "CD40L Blockade Prevents Autoimmune Diabetes by Induction of Bitypic NK/DC Regulatory Cells," Immunity, 16: 403-415 (2002).
Howard et al., "Immunotherapy Targeting the CD40/CD154 Costimulatory Pathway for Treatment of Autoimmune Disease," Autoimmunity, 37(5): 411-418 (2004).
Howard, L.M., and S.D. Miller. 2004. *Autoimmunity* 37:411-418.
Huang et al., Resolving the Conundrum of Islet Transplantation by Linking Metabolic Dysregulation, Inflammation, and Immune Regulation, Endocrine Reviews, 29(5): 603-630 (2008).
Huseby et al., "A pathogenic role for myelin-specific CD8+ T cells in a model for multiple sclerosis," Journal of Experimental Medicine, 194(5): 669-676 (2001).
Ichikawa et al., "Increased Fas antigen on T cells in multiple sclerosis," Journal of Neuroimmunology, 71(1-2): 125-129 (1996).
Iezzi et al., "CD40-CD40L cross-talk integrates strong antigenic signals and microbial stimuli to induce development of IL-17-producing CD4+ T cells," Proc Natl Acad Sci USA, 106: 876-881 (2009).
Ilonen et al., "Abnormalities within CD4 and CD8 T lymphocyte subsets in type 1 (insulin-dependent) diabetes," Clin. exp. Immunol., 85(2): 278-281 (1991).
International Preliminary Report on Patentability for International (PCT) Patent Application No. PCT/US11/56860 dated May 2, 2013, 8 pages.

(56) References Cited

OTHER PUBLICATIONS

International Preliminary Report on Patentability for International (PCT) Patent Application No. PCT/US2015/022033 dated Oct. 6, 2016, 17 pages.
International Preliminary Report on Patentability for International Application No. PCT/US11/56860 dated Apr. 23, 2013.
International Preliminary Report on Patentability for International Application No. PCT/US2015/022033 dated Jul. 24, 2015.
International Search Report and Written Opinion for International (PCT) Patent Application No. PCT/US11/56860 dated May 4, 2012, 11 pages.
International Search Report and Written Opinion for International (PCT) Patent Application No. PCT/US2015/022033 dated Jul. 24, 2015, 20 pages.
International Search Report and Written Opinion for International Application No. PCT/US11/56860 dated May 4, 2012.
International Search Report and Written Opinion for International Application No. PCT/US2019/012425 dated May 7, 2019.
International Search Report and Written Opinion for International Application No. PCT/US2020/027804 dated Jun. 22, 2020.
International Search Report and Written Opinion for International Application No. PCT/US2020/041744 dated Nov. 13, 2020.
Jensen et al., "Increased T cell expression of CD154 (CD40-ligand) in multiple sclerosis," European Journal of Neurology, 8: 321-328 (2001).
Johnson et al., "Diabetes, Insulin Resistance, and Metabolic Syndrome in Horses," J Diabetes Sci Technol, 6(3): 534-540 (2012).
Karpusas et al., "2 .ANG. crystal structure of an extracellular fragment of human CD40 ligand," Structure, 3,(10): 1031-1039 (1995).
Karpusas et al., "2 å crystal structure of an extracellular fragment of human CD40 ligand," Structure, 3(10): 1031-1039 (1995).
Kennedy et al., "Acute Exercise Induces GLUT4 Translocation in Skeletal Muscle of Normal Human Subjects and Subjects With Type 2 Diabetes," Diabetes, 48: 1-6 (1999).
Kent et al., "Expanded T cells from pancreatic lymph nodes of type 1 diabetic subjects recognize an insulin epitope," Nature, 435(7039): 224-228 (2005).
Khambhati et al., "Immunotherapy for the prevention of atherosclerotic cardiovascular disease: Promise and possibilities," Atherosclerosis 276: 1-9 (2018).
Khan et al., "Differential peptide binding to CD40 evokes counteractive responses," Hum Immunol, 73(5): 465-469 (2012).
Khan et al., "Differential peptide binding to CD40 evokes counteractive responses," Human Immunology, 73: 465-469 (2012).
King et al., "The Use of Animal Models in Diabetes Research," British Journal of Pharmacology, 166: 877-894 (2012).
Kitagawa et al., "Identification of three novel peptides that inhibit CD40-CD154 interaction," Mod. Rheumatol, 15: 423-426 (2005).
Kitagawa, M., et al.—2014—Modern Rheumatology. vol. 15-6, 423-426.
Kobata et al., "Role of costimulatory molecules in autoimmunity," Rev Immunogenet, 2(1): 74-80 (2000).
Kobata et al., "Role of costimulatory molecules in autoimmunity," Reviews in Immunogenetics, 2: 74-80 (2000).
Kuo et al., "IL-17 and CD40 ligand synergistically stimulate the chronicity of diabetic nephropathy," Nephrol Dial Transplant, 33: 248-256 (2018).
Laman et al., "Protection of marmoset monkeys against EAE by treatment with a murine antibody blocking CD40 (mu5D12)," Eur. J. Immunol., 32: 2218-2228 (2002).
Laman et al., "Therapy with antibodies against CD40L (CD154) and CD44-variant isoforms reduces experimental autoimmune encephalomyelitis induced by a proteolipid protein peptide," Multiple Sclerosis, 4: 147-153 (1998).
Lederman et al., "Identification of a Novel Surface Protein on Activated CD4+ T Cells That Induces Contact-dependant B Cell Differentiation (Help)," J. Exp. Med., 175: 1091-1101 (1992).

Lederman et al., "Identification of a novel surface protein on activated CD4+ T cells that induces contact-dependent B cell differentiation (help)," J. Exp. Med., 75(4): 1091-1101 (1992).
Lederman et al., "Molecular Interactions Mediating T-B Lymphocyte Collaboration in Human Lymphoid Follicies: Roles of T Cell-B Cell-Activating Molecule (5c8 Antigen) and CD40 in Contact-Dependent Help," The Journal of Immunology, 149(12): 3817-3826 (1992).
Lederman et al., "Molecular interactions mediating T-B lymphocyte collaboration in human lymphoid follicles. Roles of T cell-B-cell-activating molecule (5c8 antigen) and CD40 in contact-dependent help," J Immunol, 149(12): 3817-3826 (1992).
Lee et al., "Mouse models of atherosclerosis: a historical perspective and recent advances," Lipids in Health and Disease, 16: 1-11 (2017).
Leighton et al., "A Practical Review of C-Peptide Testing in Diabetes," Diabetes Ther, 8(3): 475-487 (2017).
Liu et al., "CD127 expression inversely correlates with FoxP3 and suppressive function of human CD4+T reg cells," Journal of Experimental Medicine, 203(7): 1701-1711 (2006).
Lovett-Racke et al., "Decreased dependence of myelin basic protein-reactive T cells on CD28-mediated costimulation in multiple sclerosis patients," Journal of Clincial Investigation, 101(4): 725-730 (1998).
Lucchinetti et al., "Inflammatory Cortical Demyelination in Early Multiple Sclerosis," New England Journal of Medicine, 365(23): 2188-2197 (2011).
Lutgens et al., "Long-term reversal of hypercholesterolemia in low density lipoprotein receptor (LDLR)-deficient mice by adenovirus-mediated LDLR gene transfer combined with CD154 blockade," Nature Medicine, 5: 1313-1316 (1999).
Lutterotti et al., "Antigen-specific tolerance by autologous myelin peptide-coupled cells: a phase 1 trial in multiple sclerosis," Science Translational Medicine, 5(188) 20 pages (2013).
Mach et al. "Reduction of atherosclerosis in mice by inhibition of CD40 signalling", Nature, vol. 3694, pp. 200-203, Jul. 9, 1998.
Mackey et al., "Calcifications, arterial stiffness, and atherosclerosis," Atherosclerosis, Large Arteries and Cardiovascular Risk. Adv Cardiol., 44: 234-244 (2008).
Marsh, "Nomenclature for factors of the HLA system, updated Jan. 2012," Human Immunology, 73: 593-596 (2012).
Marsh, Steven G.E. 2012. Human Immunology. vol. 73, 593-596.
Matthews et al., "Utility of murine models for the study of spontaneous autoimmune type 1 diabetes," Pediatric Diabetes, 6: 165-177 (2005).
Mayo Clinic Diabetes, mayoclinic.org/diseases-conditions/diabetes/symptoms-causes/syc-2037 1444 ?; pp. 1-7; mayoclinic.org/diseases-conditions/diabetes/diagnosis-treatment/drc-20371451?p=1; pp. 1-1 1, downloaded Feb. 20, 2012. (Year: 2012).
Mayo Clinic: Arteriosclerosis / Athersclerosis, mayoclinic.org/diseases-conditions/arteriosclerosis atherosclerosis/symptoms-causes /syc-20350569?, pp. 1-4; mayoclinic.org/diseases-conditions/arteriosclerosis- atherosclerosis/diagnosis-treatment/drc-20350575 ?p=1; pp. 1-7; downloaded Feb. 10, 2021. (Year: 2021).
McMahon et al., "Epitope spreading initiates in the CNS in two mouse models of multiple sclerosis," Nature Medicine, 11(3): 335-339 (2005).
Mcwhirter et al., "Crystallographic analysis of CD40 recognition and signaling by human TRAF2," Proc. Natl. Acad. Sci. USA, 96: 8408-8413 (1999).
McWhirter, Sarah, et al.—1999—Biochemistry—vol. 96, 8408-8413.
Miller et al., "Antigen presentation in the CNS by myeloid dendritic cells drives progression of relapsing experimental autoimmune encephalomyelitis," Annals of the New York Academy of Sciences, 1103: 179-191 (2007).
Miller et al., "Clinically isolated syndromes," Lancet Neurology, 11(2): 157-169 (2012).
Miller et al., "The role of magnetic resonance techniques in understanding and managing multiple sclerosis," Brain, 121: 3-24 (1998).
Miller et al., "Virus-induced autoimmunity: epitope spreading to myelin autoepitopes in Theiler's virus infection of the central nervous system," Advances in Virus Research, 56: 199-217 (2001).

(56) References Cited

OTHER PUBLICATIONS

Munroe et al., "Pro-Inflammatory. Adaptive Cytokines and Shed Tumor Necrosis Factor Receptors are Elevated Preceding Systemic Lupus Erythematosus Disease Flare," Arthritis Rheumatol., 66(7): 1888-1899 (2014).
Munroe et al., "Proinflammatory Adaptive Cytokine and Shed Tumor Necrosis Factor Receptor Levels Are Elevated Preceding Systemic Lupus Erythematosus Disease Flare," Arthritis Rheumatol, 66(7): 1888-1899 (2014).
Nelson et al., "Classification and etiology of diabetes in dogs and cats," Thematic Review, T1-T9 (2014).
Nguyen et al., "CD+CD40+ T cell levels predict risk of developing type I diabetes pre-diabetics," J Invest Med, Abstract, 62(1): 151-152 (2014).
Notice of Allowance and Fees Due for U.S. Appl. No. 13/880,387 dated Sep. 21, 2016.
Notice of Allowance for U.S. Appl. No. 13/880,387, dated Sep. 21, 2016.
Nyakeriga et al., "TCR-induced T cell activation leads to simultaneous phosphorylation at Y505 and Y394 of p56(lck) residues," Cytometry A, 81(9): 797-805 (2012).
O'Connor et al., "Antibodies from inflamed central nervous system tissue recognize myelin oligodendrocyte glycoprotein," Journal of Immunology, 175(3): 1974-1982 (2005).
O'Kell et al., "Comparative Pathogenesis of Autoimmune Diabetes in Humans, NOD Mice, and Canines: Has a Valuable Animal Model of Type 1 Diabetes Been Overlooked?," Diabetes, 66(7): 1443-1452 (2017).
Official Action for European Application No. 11835055.2, date Feb. 9, 2017, 4 pages.
Official Action for European Application No. 11835055.2, dated Jun. 14, 2016, 4 pages.
Official Action for European Application No. 11835055.2, dated Nov. 20, 2014, 5 pages.
Official Action for U.S. Appl. No. 13/880,387, dated Jun. 24, 2015, 14 pages.
Official Action for U.S. Appl. No. 13/880,387, dated Jun. 24, 2015, 15 pages.
Partial Supplementary European Search Report for EP Application No. EP 20840056.4 dated Mar. 23, 2023.
Patel et al., "Recent developments in protein and peptide parenteral delivery approaches," Ther. Deliv., 5(3): 337-365 (2014).
Pawson et al., "Assembly of Cell Regulatory Systems Through Protein Interaction Domains," Science, 300: 445-452 (2003).
Poggi et al., "The inflammatory receptor CD40 is expressed on human adipocytes: contribution to crosstalk between lymphocytes and adipocytes," Diabetologia, 52: 1152-1163 (2009).
Polman et al., "Diagnostic criteria for multiple sclerosis: 2010 revisions to the McDonald criteria," Annals of Neurology, 69(2): 292-302 (2011).
Polman et al., "Drug treatment of multiple sclerosis," Medicine Cabinent, 173: 398-402 (2000).
Polman et al., "Multiple sclerosis diagnostic criteria: three years later," Multiple Sclerosis Journal, 11(1): 5-12 (2005).
Pullen et al., "CD40 Signaling through Tumor Necrosis Factor Receptor-associated Factors (TRAFs)," The Journal of Biological Chemistry, 274(20): 14246-14254 (1999).
Pullen et al., "CD40 Signaling through Tumor Necrosis Factor Receptor-associated Factors (TRAFs): Binding Site Specificity and Activation of Downstream Pathways by Distinct TRAFs," J Biol Chem, 274(20): 14246-14254 (1999).
Ramsdell et al., "CD40 ligand acts as a costimulatory signal for neonatal thymic gamma delta T cells," J Immunol, 152(5): 2190-2197 (1994).
Ramsdell et al., "CD40 Ligand Acts As a Costimulatory Signal for Neonatal Thymic Gamma Delta T Cells," The Journal of Immunology, 152: 2190-2197 (1994).

Resetkova et al., "Antibody to gp39, the Ligand for CD40 Significantly Inhibits the Humoral Response from Graves' Thyroid Tissues Xenografted into Severe Combined Immunodeficient (SCID) Mice," Thyroid, 6(4): 267-273 (1996).
Richards et al., "A peptide containing a novel FPGN CD40-binding sequence enhances adenoviral infection of murine and human dendritic cells," Eur. J. Biochem., 270: 2287-2294 (2003).
Rivera et al., "Using Th40:Treg Ratio as a Predictor of Multiple Sclerosis and Other Autoimmune Diseases," University of Notre Dame, 2013, retrieved from http:/iwww.ucdenver.edu/academics/colleges/medicalschool/centersM!ebbWaring/Documents/Summer%20Students0/o202013/Erika%20Rivera%20Poster%20Final.pdf, 1 page.
Russo et al., "Platelet-Activating Factor Mediates CD40-Dependent Angiogenesis and Endothelial-Smooth Muscle Cell Interaction," J Immunol, 171: 5489-5497 (2003).
Russo et al., "Platelet-Activating Factor Mediates CD40-Dependent Angiogenesis and Endothelial-Smooth Muscle Cell Interaction," The Journal of Immunology, 5489-5497 (2003).
Sarawar et al., "Stimulation via CD40 can substitute for CD4 T cell function in preventing reactivation of a latent herpesvirus," PNAS, 98(11): 6325-6329 (2001).
Sarawar et al., "Stimulation via CD40 can substitute for CD4 T cell function in preventing reactivation of latent herpesvirus," PNAS, 98: 6325-6329 (2001).
Sawcer et al., "Genetic risk and a primary role for cell-mediated immune mechanisms in multiple sclerosis," Nature, 476(7359): 214-219 (2011).
Sawcer, "The complex genetics of multiple sclerosis: pitfalls and prospects," Brain, 131: 3118-3131 (2008).
Schonbeck et al., "Molecules in focus, CD154 (CD40 ligand)," The International Journal of Biochemistry & Cell Biology 32: 687-693 (2000).
Schonbeck et al., "The CD40/CD154 receptor/ligand dyad," CMLS—Cellular and Molecular Life Sciences, 58: 4-43 (2001).
Schönbeck et al., "CD154 (CD40 ligand)," The International Journal of Biochemistry and Cell Biology, 32(7): 687-693 (2000).
Schönbeck et al., "The CD40/CD154 receptor/ligand dyad," Cell Mol Life Sci, 58: 4-43 (2001).
Seijkens et al., "CD40-CD40L: linking pancreatic, adipose tissue and vascular inflammation in type 2 diabetes and its complications," Diab Vasc Dis Res, 10: 115-122 (2012).
Seko et al., "Expression of Tumor Necrosis Factor (TNF) Receptor/Ligand Superfamily Co-Stimulatory Molecules CD40, CD30L, CD27L, and Ox40L in Murine Hearts with Chronic Ongoing Myocarditis Caused by Coxsackie Virus B3," J. Pathol., 188: 423-430 (1999).
Seko et al., "Expression of tumour necrosis factor (TNF) receptor/ligand superfamily co-stimulatory molecules CD40, CD30L, CD27L, and OX40L in murine hearts with chronic ongoing myocarditis caused by Coxsackie virus B3," J Pathol, 188: 423-430 (1999).
Shi et al., "Ldlr-Deficient Mice with and Atherosclerosis-Resistant Background Develop Severe Hyperglycemia and Type 2 Diabetes on a Western-Type Diet," Biomedicines 10(6): 12 pages (2022).
Shukshith et al., "Water for Pharmaceutical Use," Int. J. Pharm. Sci. Rev. Res., 36(1): 199-204 (2016).
Siebert et al., "An analytical workflow for investigating cytokine profiles," Cytometry A, 73(4): 289-298 (2008).
Skolnick et al., "From genes to protein structure and function: novel applications of computational approaches in the genomic era," Trends in Biotech, 18: 34-39 (2000).
Smith et al., "Multi-peptide coupled-cell tolerance ameliorates ongoing relapsing EAE associated with multiple pathogenic autoreactivities," Journal of Autoimmunity, 27(4): 218-231 (2007).
Steck et al., "Genetics of type 1 c!iabetes," Clinical Chemistry, 57(2): 176-185 (2011).
Stein et al., "Long-term reversal of hypercholesterolemia in low density lipoprotein receptor (LDLR)-deficient mice by adenovirus-mediated LDLR gene transfer combined with CD154 blockade," The Journal of Gene Medicine, 2(1): 41-51 (2000).
Stumpf et al., "Enhanced levels of CD154 (CD40 ligand) on platelets in patients with; chronic heart failure," Eur J Heart Fail, 5: 629-637 (2003).

(56) References Cited

OTHER PUBLICATIONS

Stumpf et al., "Enhanced levels or CD154 (CD40 ligand) on platelets in patients with chronic heart failure," The European Journal of Heart Failure, 5: 629-637 (2003).
Sun et al., "Co-stimulation agonists as a new immunotherapy for autoimmune diseases," Trends in Molecular Medicine, 9(11): 483-489 (2003).
Sun, Yonglian et al., "Co-stimulation agonists as a new immunotherapy for autoimmune diseases," Trends Mol Med, 9(11): 483-489 (2003).
Thorsby et al., "Particular HLA-DQ molecules play a dominant role in determining susceptibility or resistance to Type 1 (insulin-dependent) diabetes mellitus," Diabetologia, 36(5): 371-377 (1993) (Abstract Only).
Toubi et al., "The Role of CD40-CD154 Interactions in Autoimmunity and the Benefit of Disrupting this Pathway," Autoimmunity, 37: 457-464 (2004).
Townsend et al., "CD40 signaling regulates innate and adaptive activation of microglia in response to amyloid ?-peptide," Eur J Immunol, 35: 901-910 (2005).
Townsend et al., "CD40 signaling regulates innate and adaptive activation of microglia in response to amyloid b-peptide," Eur. J. Immunol., 35: 901-910 (2005).
Vaitaitis et al, "Cutting Edge: CD40-Induced Expression of Recombination Activating Gene (RAG) 1 and RAG2: A Mechanism for the Generation of Autoaggressive T Cells in the Periphery," The Journal of Immunology, 170: 3455-3459 (2003).
Vaitaitis et al., "An Alternative Role for Foxp3 As an Effector T Cell Regulator Controlled through CD40," The Journal of Immunology, 191: 717-725 (2013).
Vaitaitis et al., "CD40 glycoforms and TNF-receptors 1 and 2 in the formation of CD40 receptor(s) in autoimmunity," Molecular Immunology, 47: 2303-2313 (2010).
Vaitaitis et al., "CD40 interacts directly with RAG1 and RAG2 in autoaggressive T cells and Fas prevents CD40 induced RAG expression," Cellular and Molecular Immunology, 10(6): 483-489 (2013).
Vaitaitis et al., "CD40-mediated signalling influences trafficking, T-cell receptor expression, and T-cell pathogenesis, in the NOD model of type 1 diabetes," Immunology, 152: 243-254 (2017).
Vaitaitis et al., "Cutting Edge: CD40-Induced Expression of Recombination Activating Gene (RAG) 1 and RAG2: A Mechanism for the Generation of Autoaggressive T Cells in the Periphery," J Immunol 170: 3455-3459 (2003).
Vaitaitis et al., "Galectin-9 Controls CD40 Signaling through a Time Independent Mechanism and Redirects the Cytokine Profile of Pathogenic T Cells in Autoimmunity," PLoS ONE, 7(6): e38708:1-13 (2012).
Vaitaitis et al., "High Distribution of CD40 and TRAF2 in Th40 T Cell Rafts Leads to Preferential Survival of this Auto-Aggressive Population in Autoimmunity," PlosOne, 3(4): e2076 (11 pages) (2008).
Vaitaitis et al., "High Distribution of CD40 and TRAF2 in TMO T Cell Rafts Leads to Preferential Survival of this Auto-Aggressive Population in Autoimmunity," PLoS ONE, 3(4): e2076: 1-11 (2008).
Vaitaitis et al., "Th40 cells (CD4+CD40+ Tcells) drive a more severe form of Experimental Autoimmune Encephalomyelitis than conventional CD4 T cells," Plos One 12(2): e0172037 (24 pages) (2017).
Vaitaitis et al., "Th40 cells (CD4+CD40+ Tcells) drive a more severe form of Experimental Autoimmune Encephalomyelitis than conventional CD4 T cells," PLoS ONE, 12: e0172037 pp. 1-24 (2017).
Vaitaitis et al., "The Expanding Role of TNF-Receptor Super Family Member CD40 (tnfrsf5) in Autoimmune Disease: Focus on Th40 Cells," Current Immunology Reviews, 6(2): 130-136 (2010).
Vaitaitis et al., Molecular Immunology. vol. 47, 2307-2313 (2010).
Vaitaitis et al., "An Alternative Role for Foxp3 As an Effector T Cell Regulator Controlled through CD40," J Immunol, 191(2): 717-725 (2013).
Vaitaitis, G.M. et al.—2012—PlosOne—vol. 7, e38708, p. 1-13.

Varo et al., "Elevated Plasma Levels of the Atherogenic Mediator Soluble CD40 Ligand in Diabetic Patients," Circulation, 107: 2664-2669 (2003).
Varo et al., "Soluble CD40L—Risk Prediction After Acute Coronary Syndromes," Circulation, 108: 1049-1052 (2003).
Wagner et al., "Expression of CD40 identifies a unique pathogenic T cell population in type 1 diabetes," PNAS, 99(6): 3782-3787 (2002).
Wagner et al., "Increased expression of CD40 on thymocytes and peripheral T cells in autoimmunity: a mechanism for acquiring changes in the peripheral T cell receptor repertoire," Int J Mol Med, 4(3): 231-273 (1999).
Wagner et al., "Increased expression of CD40 on thymocytes and peripheral T cells in autoimmunity: A mechanism for acquiring changes in the peripheral T cell receptor repertoire," International Journal of Molecular Medicine, 4: 231-242 (1999).
Waid et al., "A unique T cell subset described as CD4loCD40+ T cells (TCD40) in human type 1 diabetes," Clinical Immunology, 124: 138-148 (2007).
Waid et al., "A unique T cell subset, Th40, are pathogenic and diagnostic in mulitple sclerosis," Journal of Immunology, 186(1): Meeting Abstract (2011).
Waid et al., "Defining a new biomarker for the autoimmune component of Multiple Sclerosis: Th40 cells," J Neuroimmunol, 270(1-2): 75-85 (2014).
Waid et al., "Defining a New Biomarker for the Autoimmune Component of Multiple Sclerosis: Th40 cells," J. Neuroimmunol., 270: 75-85 (2014).
Waid et al., "Disruption of the homeostatic balance between autoaggressive (CD4+CD40+) and regulatory (CD4+CD25+FoxP3+) T cells promotes diabetes," J Leukocyte Biol, 84: 431-439 (2008).
Waid et al., "Disruption of the homeostatic balance between autoaggressive (CD4+CD40+) and regulatory (CD4+CD25+FoxP3+) T cells promotes diabetes," Journal of Leukocyte Biology, 84: 431-439 (2008).
Waid et al., "Peripheral CD4lo CD40+ auto-aggressive T cell expansion during insulin-dependent diabetes mellitus," Eur J Immunol, 34: 1488-1497 (2004).
Wang et al., "Parenteral Formulations of Proteins and Peptides: Stability and Stabilizers," Journal of Parenteral Science and Technology, 42(2S): S3-S25 (1988).
Wikipedia, "Phosphate-buffered saline," <https://en.wikipedia.org/wiki/Phosphate-bufferedsaline>: Accessed on Mar. 25, 2022 (Year: 2022).
Winer et al., "B Lymphocytes promote insulin resistance through modulation of T Lymphocytes and production of pathogenic lgG antibody," Nat Med, 17: 610-617 (2011).
Wucherpfennig et al., "A Review of T-Cell Receptors in Multiple Sclerosis: Clonal Expansion and Persistence of Human T-Cells Specific for an Immunodominant Myelin Basic Protein Peptidea," Annals of the New York Academy of Sciences, 756(1): 241-258 (1995).
Yu et al., "Targeting CD40 with a Selective Phage Display Derived Peptide," pp. 61-74.
Yu et al., "Targeting CD40 with a Selective Phage Display Derived Peptide," Universiteit Leiden The Netherlands: 61-74 (2007).
Zhang et al., "T cell and antibody responses in remitting-relapsing experimental autoimmune encephalomyelitis in (C57BL/6 x SJL) F1 mice," Journal of Neuroimmunology, 148(1-2): 1-10 (2004).
Allen et al., "Therapeutic peptidomimetic strategies for autoimmune diseases: costimulation blockade," The Journal of Peptide Research, 65(6): 591-604 (2005).
Aruffo et al., "The CD40 Ligand, gp39, Is Defective in Activated T Cells from Patients with X-Linked Hyper-lgM Syndrome," Cell, 72: 291-300 (1993).
Bai et al., "Cerebrospinal Fluid and Blood Cytokines as Biomarkers for Multiple Sclerosis: A Systematic Review and Meta-Analysis of 226 Studies With 13,526 Multiple Sclerosis Patients," *Front. Neurosci.*, 2019, 13: 1026.
Bee et al., "Exploring the Dynamic Range of the Kinetic Exclusion Assay in Characterizing Antigen-Antibody Interactions," Plos One, 7(4): e36261 (2012).

(56) References Cited

OTHER PUBLICATIONS

Bojadzic et al., "CD40-targeting KGYY15 peptides do not efficiently block the CD40-CD40L interaction," Diabetologia, 62: 2158-2160 (2019).
Buzzard et al., "Multiple Sclerosis: Basic and Clinical," Adv. Neurobiol., 2017, 15: 211-252.
Ceccarelli et al., "Microglia extracellular vesicles: focus on molecular composition and biological function," Biochem. Soc. Trans., 2021, 49(4): 1779-1790.
Chen et al., "CD40/CD40L dyad in the inflammatory and immune responses in the central nervous system," Cell Mol. Immunol., 2006, 3(3): 163-169.
Deambrosis et al., "Inhibition of CD40-CD154 costimulatory pathway by a cyclic peptide targeting CD154," J. Mol. Med., 87: 181-197 (2009).
DeGraba et al., "Efficacy of an Interdisciplinary Intensive Outpatient Program in Treating Combat-Related Traumatic Brain Injury and Psychological Health Conditions," Front Neurol, 2020, 11: 580182.
Druzd et al., "Lymphocyte Circadian Clocks Control Lymph Node Trafficking and Adaptive Immune Responses," Immunity, 2017; 46: 120-32 [PubMed: 28087238].
Edwards et al., "Interleukin-6 is associated with acute concussion in military combat personnel," BMC Neurol., 2020, 20(1): 209.
Elliott et al., "Chronic white matter lesion activity predicts clinical progression in primary progressive multiple sclerosis," Brain a Journal of Neurology, 2019, 142(9): 2787-2799.
Eshaghi et al., "Progression of regional grey matter atrophy in multiple sclerosis," Brain a Journal of Neurology, 2018, 141(6): 1665-1677.
Fan et al., "The emerging role of exosome-derived non-coding RNAs in cancer biology," Cancer Lett., 2018, 414: 107-115.
Goetzl et al., "Altered levels of plasma neuron-derived exosomes and their cargo proteins characterize acute and chronic mild traumatic brain injury," FASEB Jour., 2019, 33(4): 5082-5088.
Goetzl et al., "Traumatic brain injury increases plasma astrocyte-derived exosome levels of neurotoxic complement proteins," FASEB Jour., 2020, 34(2): 3359-3366.
Hamlett et al., "Neuronal exosomes reveal Alzheimer's disease biomarkers in Down syndrome," Alzheimers Dement., 2017, 13(5): 541-549.
Hart et al., "Preclinical assessment of therapeutic antibodies against human CD40 and human interleukin-12/23p40 in a nonhuman primate model of multiple sclerosis," Neurodegener. Dis., 2008, 5(1): 38-52.
Hartung et al., "Diagnosis of multiple sclerosis: revisions of the McDonald criteria 2017—continuity and change," Curr. Opin. Neurol., 2019, 32(3): 327-337.
Heath et al., "Monoclonal antibodies to murine CD40 define two distinct functional epitopes," Eur. J. Immunol., 24: 1828-1834 (1994).
Kalatha et al., "Glial and neuroaxonal biomarkers in a multiple sclerosis (MS) cohort," Hell. J. Nucl .Med., 2019, 22 Suppl 2: 113-121.
Kutzelnigg et al., "Cortical demyelination and diffuse white matter injury in multiple sclerosis," Brain a Journal of Neurology, 2005, 128(Pt 11): 2705-2712.
Laemmli ., "Cleavage of Structural Proteins during the Assembly of the Head of Bacteriophage T4," Nature, 227: 680-685 (1970).
Ledreux et al., "Assessment of Long-Term Effects of Sports-Related Concussions: Biological Mechanisms and Exosomal Biomarkers," Front. Neurosci. 2020, 14: 761.
Ledreux et al., "Small Neuron-Derived Extracellular Vesicles from Individuals with Down Syndrome Propagate Tau Pathology in the Wildtype Mouse Brain," J. Clin. Med., 2021, 10(17): 3931.
Liu et al., "NG2 glia are required for maintaining microglia homeostatic state," Glia, 2020, 68(2): 345-355.
Liu et al., "Targeted exosome-mediated delivery of opioid receptor Mu siRNA for the treatment of morphine relapse," Sci. Rep., 2015, 5: 17543.

Macaron et al., "Diagnosis and Management of Progressive Multiple Sclerosis," Biomedicines, 2019, 7(56): 23 pages.
Maggi et al., "Chronic White Matter Inflammation and Serum Neurofilament Levels in Multiple Sclerosis," Neurology 2021, 97(6): e543-e553.
Najafian et al., "T cell costimulatory pathways: blockade for autoimmunity," Expert Opin. Biol. Ther., 2003, 3(2): 227-236.
Nourelden et al., "Safety and Efficacy of Teplizumab for Treatment of Type One Diabetes Mellitus: A Systematic Review and Meta-Analysis," Endocr. Metab. Immune Disord Drug Targets, 10: Abstract Only (2020).
Ontaneda., "Progressive Multiple Sclerosis," Continuum (Minneap Minn), 2019, 25(3): 736-752.
Peng et al., "Microglia-Derived Exosomes Improve Spinal Cord Functional Recovery after Injury via Inhibiting Oxidative Stress and Promoting the Survival and Function of Endothelia Cells," Oxid. Med. Cell Longev., 2021, 2021: 1695087.
Pulliam et al., "Plasma neuronal exosomes serve as biomarkers of cognitive impairment in HIV infection and Alzheimer's disease," J. Neurovirol., 2019, 25(5): 702-709.
Quezada et al., "Distinct Mechanisms of Action of Anti-CD154 in Early Versus Late Treatment of Murine Lupus Nephritis," Arthritis & Rheumatism, 48(9): 2541-2554 (2003).
Rolink et al., "The SCID but Not the RAG-2 Gene Product Is Required for S?-S? Heavy Chain Class Switching," Immunity, 5(4): 319-330 (1996).
Rosetti et al., "The many faces of Mac-1 in autoimmune disease," Immunological Reviews, 269: 175-193 (2016).
Ruiz et al., "Resolution of inflammation during multiple sclerosis," Semin. Immunopathol., 2019, 41(6): 711-726.
Santilli et al., "CD40/CD40L system and vascular disease," Intern. Emerg. Med., 2007, 2(4): 256-268.
Schuh et al., "Features of Human CD3+CD20+ T Cells," J. Immunol., 2016, 197(4): 1111-1117.
Sharma et al., "Glioma-derived exosomes drive the differentiation of neural stem cells to astrocytes," PLoS One 2020, 15(7): e0234614.
Siracusa et al., "Astrocytes: Role and Functions in Brain Pathologies," Front. Pharmacol. 2019, 10: 1114.
Stys et al., "Recent advances in understanding multiple sclerosis," F1000Res, 2019, 8: 8 pages.
Sun et al., "Characterization and Biomarker Analyses of Post-COVID-19 Complications and Neurological Manifestations," Cells, 2021, 10(386): 17 pages.
Takada et al., "Integrin Binding to the Trimeric Interface of CD40L Plays a Critical Role in CD40/CD40L Signaling," J. Immunol., 203: 1383-1391 (2019).
Takahashi et al., "The role of extracellular vesicle microRNAs in cancer biology," Clin. Chem. Lab Med., 2017, 55(5): 648-656.
Takeda et al., "Neuronal Differentiation of Human Mesenchymal Stem Cells Using Exosomes Derived from Differentiating Neuronal Cells," PLoS One, 2015, 10(8): e0135111.
Thouvenot., "Update on clinically isolated syndrome," Presse Med., 2015, 44(4 Pt 2): e121-136.
Vaitaitis et al., "A CD40 targeting peptide prevents severe symptoms in experimental autoimmune encephalomyelitis," J. Neuroimmunol., 2019, 332: 8-15.
Vaitaitis et al., "Biomarker discovery in pre-Type 1 Diabetes; Th40 cells as a predictive risk factor," J. Clin. Endocrinol. Metab., 2019, 104(9): 4127-4142.
Vaitaitis et al., "CD40-targeted peptide proposed for type 1 diabetes therapy lacks relevant binding affinity to its cognate receptor Reply to Pagni PP, Wolf A, Lo Conte M et al [letter]," Diabetologia, 62: 1730-1731 (2019).
Van Kooten et al., "CD40-CD40 ligand," J. Leukoc. Biol., 2000, 67(1): 2-17.
Vaz et al., "Phenotypic Effects of Wild-Type and Mutant SOD1 Expression in N9 Murine Microglia at Steady State, Inflammatory and Immunomodulatory Conditions," Front. Cell. Neurosci., 2019, 13: 109.
Verma et al., "Not Just an Adhesion Molecule: LFA-1 Contact Tunes the T Lymphocyte Program," The Journal of Immunology, 199: 1213-1221 (2017).

(56) References Cited

OTHER PUBLICATIONS

Walling et al., "LFA-1 in T Cell Migration and Differentiation," Frontiers in Immunology, 9: Article 952 (2018).

Winston et al., "Assessing Neuronal and Astrocyte Derived Exosomes From Individuals With Mild Traumatic Brain Injury for Markers of Neurodegeneration and Cytotoxic Activity," *Front. Neurosci.*, 2019, 13: 1005.

Yu et al., "Reduced oligodendrocyte exosome secretion in multiple system atrophy involves SNARE dysfunction," *Brain a Journal of Neurology*,, 2020, 143(6): 1780-1797.

Zhang et al., "The regulation of integrin function by divalent cations," Cell Adhesion & Migration, 6(1): 20-29 (2012).

Harigai, "Involvement of CD40-D154 interaction in immunopathogenesis of collagen diseases and its application to a novel therapeutic strategy", Jpn. J. Clin. Imnunol., 27 (6) 379-388 (2004).

Poggi et al., "OP 27 New pathways involved in the cross talk between immune cells and metabolic tissues" Diabelologia 55:[Suppll JS1-S538 (2012).

Balla et al., "Iron Homeostasis in chronic inflammation" Acta Physiolgica Hungarica, vol. 94, Issue 1-2, pp. 95-106 (2007).

Barichello et al., "Biomarkers for sepsis: more than just fever and leukocytosis-a narrative review" Critical Care, 26:14 (2022).

Barichello et al., "Neurochemical effects of sepsis on the brain" Clinical Science, vol. 137, p. 401-414 (2023).

Barichello et al., "The blood-brain barrier dysfunction in sepsis" Tissue Barriers, vol. 9, No. 1. (2021).

Chew et al., "Soluble CD40L (CD154) is increased in patients with shock" Inflammation Research, vol. 59, p. 979-982 (2010).

Curran et al., "Ocrevus reduces TH40 cells, a biomarker of systemic inflammation, in relapsing multiple sclerosis (RMS) and in progressive multiple sclerosis (PMS)" Journal of Neuroimmunology, vol. 374 (2023).

Extended European Search Report for EP Application No. 23181309.8 dated Sep. 19, 2023.

Gambichler et al., "Prognostic Performance of Inflammatory Biomarkers Based on Complete Blood Counts in COVID-19 Patients" Viruses, vol. 15 (2023).

Hager et al., "Affinity and Epitope Profiling of Mouse Anti?CD40 Monoclonal Antibodies", Scandinavian journal of immunology 57.6: 517-524 (2003).

Hao et al., "Increased inflammatory mediators levels are associated with clinical outcomes and prolonged illness in severe COVID-19 patients" International Immunopharmacology, vol. 123 (2023).

Liu et al., "CD11b is a Novel Alternate Receptor for CD154 during Alloimmunity" Am J Transplant, vol. 20, No. 8, p. 2216-2225 (2020).

Matsumoto et al., "The clinical importance of a cytokine network in the acute phase of sepsis" Scientific Reports, vol. 8 (2018).

Michels et al., "CD40-CD40 Ligand Pathway Is a Major Component of Acute Neuroinflammation and Contributes to Long-term Cognitive Dysfunction after Sepsis" Molecular Medicine, vol. 21 (2015).

Nolan et al., "CD40 but Not CD154 Knockout Mice Have Reduced Inflammatory Response in Polymicrobial Sepsis: a Potential Role for *Escherichia coli* Heat Shock Protein 70 In CD40-Mediated Inflammation in Vivo" Shock, vol. 22, No. 6, pp. 538-542 (2004).

Sekino et al., "Sepsis-associated brain injury: underlying mechanisms and potential therapeutic strategies for acute and long?term cognitive impairments" Journal of Neuroinflammation, vol. 19 (2022).

Tang et al., "Molecular basis and therapeutic implications of CD40/CD40L immune checkpoint" Pharmacol Ther, vol. 219 (2021).

Urbanski et al., "Serum ferritin/C-reactive protein ratio is a simple and effective biomarker for diagnosing iron deficiency in the context of systemic inflammation" QJM: An International Journal of Medicine (2023).

Yao et al., "Neutrophil to lymphocyte ratio (NLR), platelet to lymphocyte ratio (PLR), and systemic immune inflammation index (SII) to predict postoperative pneumonia in elderly hip fracture patients"Journal of Orthopaedic Surgery and Research (2023).

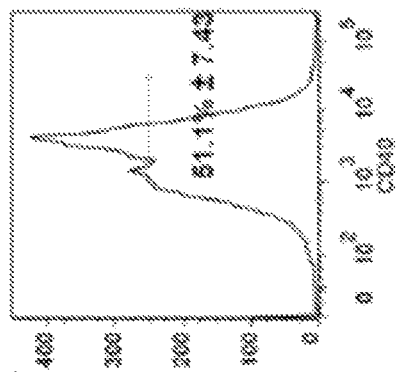
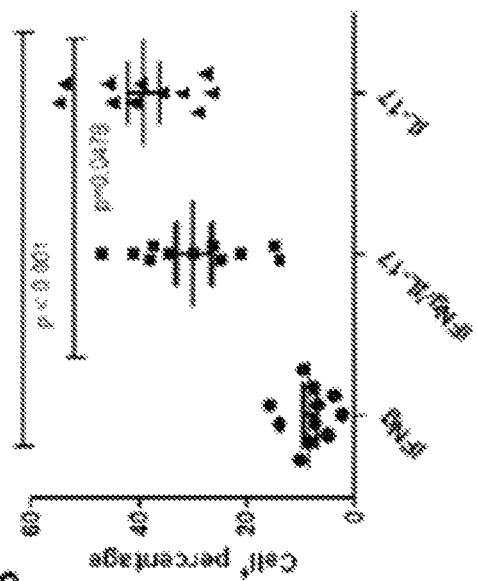
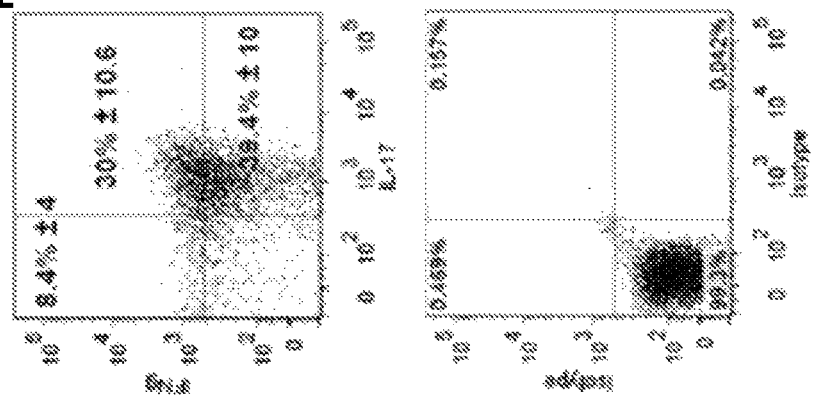
FIG. 2A
FIG. 2B

Glucose during GTT

Insulin during GTT

Fructoseamine

Fructoseamine

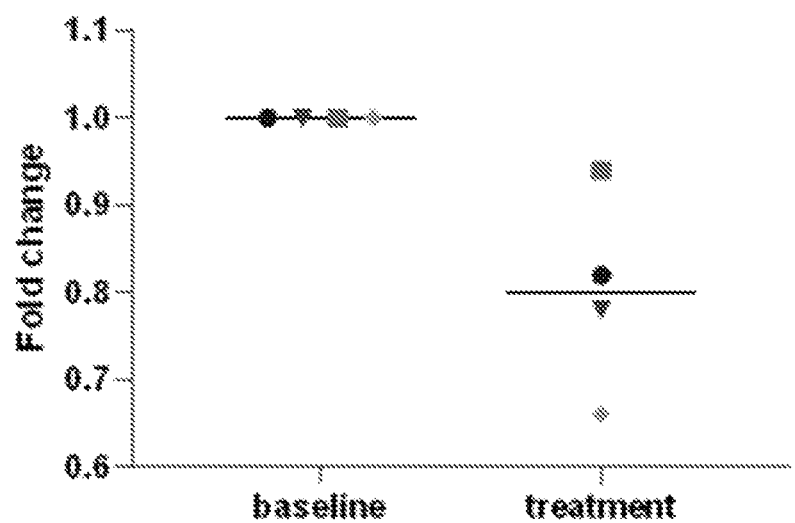

Outlier removed

BIOACTIVE PEPTIDES AND METHODS OF USE THEREOF

CROSS-REFERENCE TO RELATED APPLICATION

This application claims the benefit of the following U.S. Provisional Application Nos.: 63/011,921, filed Apr. 17, 2020, and 63/031,192, filed May 28, 2020, the entire contents of each are incorporated herein by reference.

SEQUENCE LISTING

The instant application contains a Sequence Listing which has been submitted electronically in ASCII format and is hereby incorporated by reference in its entirety. Said ASCII copy, created on Aug. 30, 2021, is named OPB-01001A_SL.txt and is 12,532 bytes in size.

FIELD

The present developments relate to the use of bioactive peptides for providing therapeutic relief to patients suffering from cytokine release syndrome (CRS). The developments, in the field of biochemistry, molecular biology, and medicine relate to the treatment of cytokine release syndrome (CRS), acute lung injury (ALI), acute respiratory distress syndrome (ARDS), including additional symptoms that develop in seriously ill individuals. More specifically, the developments include compositions of matter, including peptides, and methods of use thereof for interfering and/or inhibiting the interaction of the CD40 complex with CD154.

BACKGROUND

Cytokine Release Syndrome

Many patients with severe COVID-19 may experience cytokine release syndrome (CRS), which may also cause of death (Zhang et al, 2020; Mehta et al, 2020; Ruan et al, 2020).

Physicians and researchers may characterize CRS as a systemic inflammatory response that may be caused by several factors. Additionally, CRS may be an adverse effect of some monoclonal antibody therapies, most notably, but not limited to, anti-CD3 (OKT3), anti-CD52 (alemtuzumab), anti-CD20 (rituximab), and the CD28 super-agonist, TGN1412. (Lee et al, 2014). Other studies have shown that some instances, immune system related diseases, immune-related therapies, e.g., CAR-T cell therapy, organ transplantation related sepsis, viral infections, and some drugs may lead to CRS. (Zhang et al, 2020; Lee et al, 2014).

Clinicians and researchers alike have contemplated and proposed a number of theories and hypotheses regarding the biological and cellular aspects of CRS. Generally, cytokines are broadly defined to be small proteins, or peptides, released by cells that may have a specific effect on the interaction or communication between cells, or the behavior of cells. Cytokines may include interleukins, lymphokines, and other cell signal molecules, such as tumor necrosis factors (TNFs) and interferons (IFNs), which may trigger inflammation and may assist a body in responding to an infection.

Thus, one hallmark of CRS may be a sharp increase in the level of many pro-inflammatory cytokines such as interferon-γ (IFN-γ), tumor necrosis factor α (TNF α), interleukin-2 (IL-2), interleukin-1 alpha and 1 beta (IL-la and IL-1b) and interleukin-6 (IL-6) among others, along with changes in vital signs such as a high fever. (Lee et al, 2014). Additionally, research regarding CRS in mouse models may demonstrate that mortality and cytokine release is dependent on TCRa T cells. (Faulkner et al, 2005).

Research concerning severe acute respiratory syndrome coronavirus 2 (SARS-CoV-2), which causes COVID-19, shows that the virus (SARS-CoV-2) binds to alveolar epithelial cells and consequently the innate and the adaptive immune system may be activated. (Zhang et al, 2020). Additionally, many other coronaviruses, including SARS-CoV-1 and MERS may also bind to lung epithelium, and in particular to type 2 pneumocytes. Moreover, current research also suggests that influenza can also bind to lung epithelium and cause the innate and adaptive immune systems to be activated. As a result of the activation of the innate and adaptive immune system, the tissues may release many cytokines, including IL-6. Additional research regarding COVID-19 has shown that while there are other comorbidities such as hypertension, cardiovascular disease, and diabetes associated with the disease, fatalities in the most severe cases of COVID-19 may be caused by CRS and may be predicted by increased levels of ferritin and IL-6. (Mehta et al, 2020; Ruan et al, 2020; Zhang et al, 2020).

Several treatment options have been put forward to address and control CRS. One approach uses Actemra® (Tocilizumab) which is an immunosuppressive drug that is a humanized monoclonal antibody against the IL-6 receptor. Although anecdotal evidence suggests Actemra® may be efficacious in reducing CRS, no randomized trial has provided direct evidence of IL-6R blockade resulting in reduced incidence or severity of CRS. Another approach to attempt to control CRS utilizes Lenzilumab which is a humanized monoclonal antibody (class IgG 1 kappa) that targets colony stimulating factor 2 (CSF2) I granulocyte-macrophage colony stimulating factor (GM-CSF). Lenzilumab is thought to work by reducing activation of myeloid cells and decreasing the production of IL-1, IL-6, MCP-1, and IP-10. These treatments that utilize monoclonal antibodies are designed to alter the immune system's response to self-tissues, as they occur during autoimmune diseases such as rheumatoid arthritis or systemic juvenile idiopathic arthritis as with Tocilizumab; or graft versus host disease as with Lenzilumab; however, clinical trials are only now beginning to test these treatment options while COVID-19 continues to spread and cause severe CRS in patients. Moreover, humanized monoclonal antibodies while often functional, may cause a variety of undesirable side effects that may be immediate and/or latent.

Thus, there may exist a need in the art for alternative compositions and methods for treatment and prevention of CRS. The present developments address this need by describing a novel method for treatment of CRS.

Acute Respiratory Distress Syndrome

The alveolar capillary membrane is the thin tissue barrier between the alveolar sacs ("the alveolus") of the lungs and the pulmonary capillaries through which gases, notably oxygen and carbon dioxide, are exchanged. (Fanelli V, et al. J. of Thoracic Disease 5:326-34, 2013). Additionally, the alveolar capillary membrane is actively involved in solute and fluid flux between the alveolar surface, interstitium, and the blood, as well as fluid clearance from the alveolar spaces into interstitial spaces. Proper gas and fluid exchange and regulation at the alveolar capillary membrane is important to proper oxygenation and prevention of hypoxemia (decreased oxygen in the blood) and hypercapnia (increased carbon dioxide in the blood) and a central feature of maintaining health. (Id).

Alveolar capillary membrane injury is often preceded, initiated, and caused by a wide variety of predisposing insults (Id; Ware, L B Seminars in Respiratory and Critical Care Medicine 27:337-49, 2006; Brady, V. Critical Care Nursing Clinics of North America 25:7-13, 2013). Oftentimes alveolar capillary injury can arise following and complicate infection, sepsis, pneumonia, aspirations, trauma, hyperoxia, radiation, hemorrhage, blast exposure, pancreatitis, brain injury, smoke inhalation, transfusions, drug reactions, complex surgery and many other predisposing disorders; however, the reasons for these developments remain unknown. Individuals possessing any pre-disposing disorders or conditions such as those listed above may be more likely to develop Acute Respiratory Distress Syndrome (ARDS).

Alveolar capillary membrane injury is a feature of an can cause syndromes such as ARDS and many other related and similar disorders that are known as shock lung, Da Nang Lung, white lung, adult respiratory distress syndrome, acute lung injury, acute edematous lung injury, wet lung, lung edema, pulmonary edema, and other names that are used as synonyms of alveolar capillary membrane injury. ARDS may also characterized or classified as the often fatal, non-cardiogenic, acute, usually diffuse, edematous, hemorrhagic and/or inflammatory lung injury. ARDS may in many instances lead to multiple organ failure (MOF) and death. Moreover, ARDS may contribute to addition long term disorders including severe muscle weakness, psychiatric disorders, and/or other continuing disabilities with long term consequences.

The process or events that incite or lead to ARDS may be unclear in some instances; however in other instances ARDS may be brought on by infection with a known viral infection such as the case with severe acute respiratory syndrome coronavirus 2 (SARS-CoV-2), which causes COVID-19. In either case, that is whether the acute cause is known or unknown, ARDS appears to involve a cytokine-triggered systemic and lung inflammation characterized by increased blood and lung cytokine levels (e.g. IL-I, IFN-γ, TNF-α, and IL-8) and a rapid influx of inflammatory cells including neutrophils (PMN), lymphocytes, and mononuclear phagocytes into the lung.

Research supports a role for neutrophils, macrophages, platelets, and T-lymphocytes each playing a role in the development of ARDS. For example, prior experiments and studies have shown that neutrophil depletion may decrease acute edematous lung injury in animal models and the ability of neutrophils to cause acute edematous injury in isolated perfused lungs. However, compared to investigations of neutrophils, macrophages, and platelets, the participation of T-lymphocytes ("T-cells") in ARDS has been relatively underappreciated (Smiley D, et al, Annals N Y Acad. Of Sci. 12:1-11, 2010; Lleva R and Inzucchi S E, Curr. Op. in Endo. Diab. and Obesity 18:110-18, 2011; Van den Berghe et al, NEJM, 345: 1359-67, 2001). This may be unexpected because T-cells are of important players and early drivers in immune responses and inflammation.

Furthermore, some research has suggested that T-cells may play an important role such as one study that showed that IL-17 producing CD4+ and CD8+ T-cells were increased in lung lavages of ARDS patients. (Smiley D, et al, supra). In addition, RAG (recombination activating gene)-knockout mice developed milder ARDS and less neutrophil migration into the lung. (Lleva R and Inzucchi S E, supra). However, little work has been done regarding CD40+ T cells and because of the different functions of T cell subsets, it may be unexpected that CD40+ T cells would be involved or contribute to ARDS, or that a bioactive peptide that acts upon the CD40 complex may be able to prevent, modulate, control, inhibit, or in some way affect ARDS.

Interestingly, no specific evidence exists that hyperglycemia occurs or contributes to ARDS; however, administering intensive insulin to maintain blood glucose at or below 110 mg/dl may reduce morbidity and mortality among critically ill patients in a surgical intensive care unit compared to a group of patients in which blood glucose levels were higher ranging from 140-200 mg/dl. (Van den Berghe G., supra). Remarks and observations of patient with chronic disorders, such as obesity, may implicate a relationship between hyperglycemia, inflammation, and oxidative stress but the effects of acute hyperglycemia on the development of alveolar capillary membrane injury and the effects of hyperglycemia on inflammation remain unclear. (de Carvalho V F, et al., Nutrition Hospital 27: 1391-98, 2012).

Currently, ARDS treatments are limited to mechanical ventilation, which may include airway pressure release ventilation or positive end-expiratory pressure, oxygen therapy, prone positioning, fluid management, extracorporeal membrane oxygenation (ECMO), and in some cases inhaled nitric oxide (NO). However, no pharmaceutical therapies are currently available that treat or remedy the root cause of ARDS or other syndromes associated with the development or acute or chronic consequences of alveolar capillary membrane injury. And according to the National Heart, Lung, and Blood Institute of the NIH, the only medicinal treatments available for the treatment of ARDS appear to be limited to anti-microbials or anti-virals used for treating the pathogen that may be an underlying cause, and therapeutic agents which may provide supportive care, relieve pain, and/discomfort caused by the syndrome.

Many practitioners and clinicians recognize that ARDS as a disease that is extremely difficult to treat once it has become sufficiently established in a corporeal body. Moreover, practitioners and clinicians acknowledge that the currently available and necessary treatments may be potentially harmful. For example, mechanical ventilation may be associated with complications such as ventilator-associated pneumonia and ventilator-associated lung injury. Further, the use of high concentrations of inspire oxygen needed to avoid hypoxemia may also be potentially toxic to the lung, possibly because they may increase the production of toxic oxygen free radicals. Therefore, a treatment is needed that is effective, and not harmful when given before, during, or after exposure to an ARDS-inciting insult and after ARDS has started.

CD40, a member of the TNF receptor superfamily, is known to drive inflammatory responses and cytokine production by many immune cells including monocytes, T cells, and dendritic cells. (Wagner, 1996; Poe et al, 1997; Vaitaitis et al, 2014; Ma and Clark, 2009). CD40 may drive the expansion of self-reactive pro-inflammatory T cells, a subpopulation of TCRa CD4 T cells that are characterized by expression of CD40 (Th40 cells). Th40 cells may be responsible for auto-inflammation in Type 1 Diabetes (T1D) and Multiple Sclerosis (MS) as research has demonstrated that Th40 cells express pro-inflammatory cytokines that drive the auto-inflammation in both T1D and MS. (Vaitaitis et al, Immunology, 2017; Waid et al, 2008; Wagner et al, 2002). Moreover, additional and further research interestingly suggests that SARS-like viral particles may induce CD40 expression on dendritic cells. (Bai, et al, 2008).

CD40 is a 50-kDa integral membrane protein of the tumor necrosis factor receptor (TNF-R) family. It is constitutively expressed as a homotrimer (Foy T M, et al., Ann. Rev. Immunol., 14:591, 1996). In general, stimulation of all CD40-expressing cell types induces operations which contribute to inflammation, such as enhancement of costimulatory and adhesion molecules, and up-regulation of proteolytic enzymes (Mach, F. et al., Atherosclerosis. 137 Suppl: 589-95, 1998).

CD40's ligand—CD154—is a 39-kDa protein that belongs to the tumor necrosis factor (TNF) family. CD40 forms a trimer that binds CD154 at the interface of the three monomers. CD154 is expressed commonly on cells beyond the surface-expressed CD154, as CD154 may also exist in a soluble biologically active form (sCD154) that is shed from the cell surface after activation. The main source of sCD154 is platelets. (Kaufman, J. et al., J. Thrombosis Haemostasis, 5:788-96, 2007).

CD154 is known to interact with aMβ2 (CD11b/CD18), a5β1 (CD49e/CD29), and α11b β3 (CD41/CD61) found on platelets. Moreover, CD154 has been found to interact with several other integrins including aL (CD11a), aM (CD11b), αD (CD11d), β4 (CD104), α3 (CD49c), and α5 (CD49e). Interestingly, Th40 cells are capable of reactivating recombination activating gene (RAG) 1 and 2 which leads to alteration of the TCRs expressed by these mature, peripheral T cells. Such alterations could potentially lead to epitope spreading, thus expanding the TCR repertoire.

As described above, both CRS and ARDS are potentially deadly conditions and often require intensive and immediate medical attention; however, currently few therapeutic treatment options currently may exist to treat these conditions. Thus, there exists a need in the art for alternative compositions and methods for treatment and prevention of CRS and ARDS. The present developments address this need by describing a novel method for treatment of CRS and ARDS.

SUMMARY

The present developments provide a novel method for treating, modulating, and/or reducing cytokine release syndrome (CRS). In some instances, CRS may arise as a result of an infection with severe acute respiratory syndrome coronavirus 2 (SARS-CoV-2), which causes COVID-19. In other instances, CRS may arise as a result of an infection with other coronaviruses, influenzas, pneumonia, or any other form of CRS, including those instances caused by medical treatments and physical trauma. The developments hereof may also treat CRS that may not be related to ARDS, ALI, trauma, monoclonal antibodies or other therapies, including but not limited other treatments such as cancer chemotherapy treatments and CAR-T cell treatments that may result in CRS.

The present developments also relate to methods of treating subjects before, during, and/or after the development of ALI and/or ARDS, with a specific peptide and/or other compounds to simultaneously reduce alveolar capillary membrane injury, CD40+ T cell levels in the blood and lung, and hyperglycemia.

Thus, the developments and implementations disclosed herein and hereof may include compositions of matter and methods of treating and/or reducing the incidence of cytokine release syndrome (CRS) and acute respiratory distress syndrome (ARDS). These methods include administering to a subject in need of a treatment an effective amount of a peptide to inhibit, interfere, or affect the binding between proteins associated with CD40 complex, including but not limited to CD154. In these methods, the diseases or disorders may include CRS, ARDS, acute lung injury, severe lung inflammation, emphysema, chronic obstructive pulmonary disease, asthma, bronchitis, pneumonia, pulmonary edema, acute bacterial lung infection, acute viral lung infection, infant respiratory distress syndrome, sepsis, lung trauma, aspiration, pancreatitis, burn, toxin inhalation, pulmonary infection, and/or any other alveolar capillary membrane injury inciting or producing event, and any condition resulting in the cytokine release syndrome or cytokine storm syndrome.

The developments are based on the knowledge that interaction of CD40-ligand (CD154 protein) with CD40 protein expressed on T-cells (Th40 cells), is important pathway in inflammatory disorders. While targeting of selected cytokines may be useful in blunting the most severe peak of CRS, it may be advantageous to target several of the pro-inflammatory cytokines at once. A treatment that could possibly achieve that is the unique peptide KGYY15, with a sequence derived from the CD154 protein. CD154 (a member of the TNF super family) is the ligand for CD40 and the mouse CD154-derived sequence VLQWAKKGYYTMKSN spans a region with known CD40– interacting amino acids. Thus, the developments hereof may also be based on the elucidation of the critical residues in CD40 and CD154 that are important for this interaction. The present developments relate to blocking the interaction between a CD40 protein and a CD154 protein through the use of small peptides that interact with the CD40 protein at a site where the CD154 protein would normally bind. The present developments also relate to using such peptides to reduce the level of Th40 cells, thereby reducing the severity of disease.

The inhibitor peptides useful in the methods hereof may be a peptide that binds to CD40. The inhibitor peptide may disrupt, affect, or modify the interaction of CD40 with CD154 thereby reducing the number of Th40 cells in the subject. The inhibitor peptide may include an amino acid sequence selected from the group of SEQ ID NO: 3, SEQ ID NO: 4, SEQ ID NO: 27, SEQ ID NO: 28, SEQ ID NO: 29, and SEQ ID NO: 30. The bioactive peptide may have the amino acid sequence of SEQ ID: 3. These inhibitor peptides may include a modification selected from phosphorylation and glycosylation, and/or may be linked to a polyethylene glycol (PEG) molecule, and/or may be linked to one or more domains of an Fc region of human IgG immunoglobin, and/or may be linked to an epitope tag polypeptide comprising between 6 and 50 amino acid residues. Additionally, the inhibitor peptides hereof may also include modifications of termini such as acetylation and amidation. Additionally, peptides hereof may include several salt forms including hydrochloride salts, acetate salts, TFA salts, and sodium chloride salts.

In these methods, the therapeutic peptide hereof may be administered to the lungs of the subject. For example, the peptide may be via an inhaled mist or administered intranasally. Moreover, in these methods the therapeutic peptide hereof may be administered to the subject in combination with a therapeutically effective amount of one or more compounds including N-acetylcysteine (NAC), ergothioneine (ERGO), alpha-lipoic acid, a CD40+ T cell reducing or inactivating agent, and a hypoglycemic agent. Administration is described in more detail below; however, the developments hereof contemplate and include IV bolus, infusion, subcutaneous, intramuscular, and oral routes of administration.

Thus, one aspect of the present disclosure provides a method of treating or reducing the incidence and/or severity of a disease or disorder that results from inflammatory cytokine production, comprising administering to a subject in need of such a treatment an effective amount of a peptide that alters or modulates the binding or interaction between CD40 complex and CD154 proteins.

Numerous embodiments are further provided that can be applied to any aspect disclosed herein and/or combined with any other embodiment described.

For example, in some embodiments, the disease or disorder is selected from the group of cytokine release syndrome (CRS), acute respiratory distress syndrome (ARDS), alveolar capillary membrane injury, and acute lung injury (ALI). In other embodiments, the disease or disorder selected from the group of severe lung inflammation, emphysema, chronic obstructive pulmonary disease (COPD), asthma, bronchitis, pneumonia, pulmonary edema, acute bacterial lung infection, acute viral lung infection, infant respiratory distress syndrome (IRDS), sepsis, lung trauma, aspiration, pancreatitis, bum, toxin inhalation, pulmonary infection, severe blood loss and/or any other alveolar capillary membrane injury inciting or producing event. In still other embodiments, the peptide binds to CD40 complex. In some embodiments, the peptide disrupts or alters the interaction of CD40 complex with CD154 and reduces the number of Th40 cells in the subject. In some embodiments, the peptide is selected from the group consisting of SEQ ID NO:4, SEQ ID NO:5, SEQ ID NO:6, SEQ ID NO:7, SEQ ID NO:8, SEQ ID NO:27, SEQ ID NO:28, SEQ ID NO:29, SEQ ID NO:30, SEQ ID NO:32, SEQ ID NO:33, and SEQ ID NO:34. In some embodiments, the peptide having an amino acid sequence of SEQ ID NO: 3. In some embodiments, the peptide decreasing an amount of inflammatory cytokine selected from the group of IL-2, IFNγ, IL-6, TNFα, and IL-17A. In some embodiments, the peptide comprises a modification selected from phosphorylation, glycosylation, acetylation on the N-terminus and/or amidation on the C-terminus. In some embodiments, the peptide is linked to a polyethylene glycol (PEG) molecule. In some embodiments, the peptide is linked to one or more domains of an Fc region of human IgG immunoglobin. In some embodiments, the Fc region is human IgG hinge, CH2, CH3 region that is fused to at least one of the amino-terminus or carboxyl-terminus of the peptide. In some embodiments, the peptide is administered to the lungs of the subject.

Another aspect of the present disclosure provides a method of treating or reducing the incidence and/or severity of an acute inflammation disorder, comprising administering to a subject in need of such treatment an effective amount of an inhibitor modulating CD40 cell levels. In some embodiments, the acute inflammation disorder is selected from the group consisting of sepsis, acute lung injury (ALI), acute respiratory distress syndrome (ARDS), severe lung inflammation, emphysema, chronic obstructive pulmonary disease (COPD), asthma, bronchitis, pneumonia, pulmonary edema, acute bacterial lung infection, acute viral lung infection, infant respiratory distress syndrome, lung trauma, aspiration, pancreatitis, burn, toxin inhalation, pulmonary infection and/or any other alveolar capillary membrane injury inciting or producing event. In some embodiments, the inhibitor is a peptide that binds to or otherwise interacts with CD40. In some embodiments, the inhibitor is a peptide that disrupts the interaction of CD40 with CD154 thereby reducing the number of Th40 cells in the subject. In some embodiments, the inhibitor is a peptide comprising an amino acid sequence selected from the group consisting of SEQ ID NO:2, SEQ ID NO:3, SEQ ID NO:4, and SEQ ID NO:5. In some embodiments, the inhibitor is a peptide comprising the amino acid sequence of SEQ ID NO:4. In some embodiments the inhibitor peptide comprises a modification selected from phosphorylation and glycosylation. In some embodiments, the inhibitor peptide is linked to a polyethylene glycol (PEG) molecule. In some embodiments, the number of ethylene glycol (EG) units in the PEG molecule is between 460 to 1840. In some embodiments, the inhibitor peptide is linked to one or more domains of an Fc region of human IgG immunoglobulin. In some embodiments, the Fc region is a human IgG hinge, CH2, and CH3 region that is fused to at least one of the amino-terminus or carboxyl-terminus of the peptide. In some embodiments, the inhibitor peptide is linked to an epitope tag polypeptide comprising between 6 and 50 amino acid residues. In some embodiments, the inhibitor is administered via IV infusion, subcutaneous injection, intranasally, in pill form or transdermally to the subject. In some embodiments, the inhibitor is administered intranasally. In some embodiments, the method further comprises administering to the subject a therapeutically effective amount of one or more compounds selected from the group consisting of N-acetylcysteine (NAC), ergothioneine (ERGO), alpha-lipoic acid, a CD40+ T cell reducing or inactivating agent, and a hypoglycemic agent.

Another aspect provides a method of treating, controlling or preventing hyperglycemia in a subject, with or without diabetes, comprising administering to the subject a composition comprising an amino acid sequence selected from the group consisting of SEQ ID NO:2, SEQ ID NO:3, SEQ ID NO:4, and SEQ ID NO:5, and functional fragments and/or analogs thereof, in an amount and under conditions effective to decrease hyperglycemia in the subject. In some embodiments, the blood glucose levels of the subject are reduced to less than 140 mg/dl, or less than 120 mg/dl, or less than 110 mg/dl. In some embodiments, the blood glucose levels of the subject are maintained greater than 80 mg/dl, or greater than 90 mg/dl, or greater than 100 mg/dl. In some embodiments, the subject is developing an acute inflammation disorder or suspected of developing an acute inflammation disorder or at risk of developing an acute inflammation disorder. In some embodiments, the hyperglycemia in the subject is reduced in the treatment of toxemia, inflammation, infection, bacteremia, sepsis, septic shock, acute lung injury, severe acute respiratory syndrome (SARS), systemic inflammatory response syndrome (SIRS), or multiple organ dysfunction syndrome (MODS). In some embodiments, the levels of insulin used in the hyperglycemic subject are reduced due to the improved control of blood glucose levels. In some embodiments, the levels of ferritin in the circulating blood is lowered as a result of the administration of the peptide.

In yet another aspect of the present disclosure, a peptide is provided that binds to or modulates CD40 complex; alters or modulates the binding or interaction between CD40 complex and CD154 proteins; and/or treats or prevents a disease or disorder selected from the group of cytokine release syndrome (CRS), acute respiratory distress syndrome (ARDS), alveolar capillary membrane injury, and acute lung injury (ALI).

Another aspect provides a peptide that disrupts or alters the interaction of CD40 complex with CD154 and reduces the number of Th40 cells in the subject.

In some embodiments of any of the aspects provided herein, the peptide is selected from the group consisting of SEQ ID NO: 2; SEQ ID NO: 3; SEQ ID NO: 4, SEQ ID NO:5, SEQ ID NO:6, SEQ ID NO:7, SEQ ID NO:8, SEQ ID NO: 27, SEQ ID NO:28, SEQ ID NO:29, SEQ ID NO:30, SEQ ID NO: 32, SEQ ID NO:33, and SEQ ID NO: 34. In some embodiments, the peptide having an amino acid sequence of SEQ ID NO: 3. In some embodiments, the peptide decreasing an amount of inflammatory cytokine selected from the group of IL-2, IFNγ, IL-6, TNFα, and IL-17A. In some embodiments, the peptide comprises a modification selected from phosphorylation, glycosylation, acetylation on the N-terminus and/or amidation on the C-terminus. In some embodiments, the peptide is linked to a polyethylene glycol (PEG) molecule. In some embodiments, the peptide is linked to one or more domains of an Fc region of human IgG immunoglobin. In some embodiments, the Fc region is human IgG hinge, CH2, CH3 region that is fused to at least one of the amino-terminus or carboxyl-terminus of the peptide. In some embodiments, the peptide is administered to the lungs of the subject. In some embodiments, the peptide one or more of affects, decreases, increases, and/or modulates the blood cytokine levels of one or more of IL-1β, IL-6, TNFα, IFN-γ, IL-2, IL-17A, IL-12, IL-4, IL-10, IL-2rec, IL-5, and/or IL-8. In some embodiments, the peptide one or more of affects or results in changes to one or more of CD3+, CD4+, CD45RA+, CD45RO+, CD8+ and CD19+ lymphocytes, and NK cells. In some embodiments, the peptide one or more of affects or results in changes to one or more of ferritin, high-sensitivity C-reactive protein (hs CRP), and/or LDH. In some embodiments, the administration of the peptide does not cause any abnormal increase in the clotting cascade.

This Summary is neither intended nor should it be construed as being representative of the full extent and scope of the present disclosure. Moreover, references made herein to "the present disclosure" or aspects thereof, should be understood to mean certain implementations of the present disclosure and should not necessarily be construed as limiting all implementations to a particular and/or description. These as well as other alternative and/or additional aspects are exemplified in a number of illustrated alternative and/or additional implementations and applications, some of which are shown in the figures and characterized in the claims section that follows. However, as will be understood by the ordinarily skilled artisan, the above summary and the detailed description below do not describe the entire scope of the developments hereof and are indeed not intended to describe each illustrated embodiment or every implementation of the present developments nor provide any limitation on the claims or scope of protection herein set forth below. Additional features, versions, characteristics and aspects of the present disclosure may become more readily apparent from the Detailed Description, particularly when taken together with the drawings.

BRIEF DESCRIPTION OF THE DRAWINGS

The drawings include:
FIG. 1A compares TNFα expression from T1D subjects and controls.
FIG. 1B compares IFNγ expression from T1D subjects and controls.
FIG. 1C compares IL-6 expression from T1D subjects and controls.
FIG. 1D compares IL-4 expression from T1D subjects and controls.
FIG. 1E compares IL-6 expression from T1D subjects and controls.
FIG. 1D compares Th1 and Th2 cells from T1D subjects and controls.

FIGS. 2A and 2B provide dot plots and graphs of memory phenotype Th40 cells from MS patients showing production of both IL-17 and IFNγ. FIG. 2A shows flow cytometry data of total blood lymphocytes gated for CD4 and CD45RO expression to delineate memory cells. Within that population Th40 cells were assayed for IFNγ and IL-17 production by intra-cellular staining. Levels of IL-17 and IFNγ were determined above isotype controls. FIG. 2B shows levels of IFNγ only, IL-17 only and IFNγ/IL-17 double positive cells from 11 RRMS subjects.

FIG. 3A shows data characterizing purified peripheral blood lymphocytes from MS patients with high Th40 cell levels stained for CD3, CD4, CD40 and intracellularly for different cytokines then analyzed by flow cytometry. FIG. 3B shows data characterizing purified peripheral blood lymphocytes from MS patients with low Th40 cell levels stained for CD3, CD4, CD40 and intracellularly for different cytokines then analyzed by flow cytometry. For FIGS. 3A and 3B, cells were gated on CD4 versus CD40 and CD3 expression was confirmed for Th40 cells then cytokine expression was analyzed within the Th40 population. FIG. 3C shows that IL-6, IFNγ, and IL-2 were statistically different between Th40 high and Th40 low (Two-way ANOVA with Sidak's multiple comparisons test).

FIG. 4A shows data for lymphocytes isolated from CA/CPR induced mice at 3 hr., 24 hr., 48 hr. and 72 hr. post injury and stained intracellularly for the Th1, pro-inflammatory cytokine TNFα. FIG. 4B shows data for lymphocytes isolated from CA/CPR induced mice at 3 hr., 24 hr., 48 hr. and 72 hr. post injury and stained intracellularly for the Th1, pro-inflammatory cytokine IFNγ. FIGS. 4A and 4B show cytokines in total CD4+ T cells. FIG. 4C shows data for lymphocytes isolated from CA/CPR induced mice at 3 hr., 24 hr., 48 hr. and 72 hr. post injury and stained intracellularly for the Th1, pro-inflammatory cytokine TNFα. FIG. 4B shows data for lymphocytes isolated from CA/CPR induced mice at 3 hr., 24 hr., 48 hr. and 72 hr. post injury and stained intracellularly for the Th1, pro-inflammatory cytokine IFNγ. FIGS. 4C and 4D show cytokines in the Th40 subset of CD4+ cells FIG. 5 provides graphs of IFNγ, TNF α, IL-17, IL-10, IL-2, and IL-21 measurements of draining lymph nodes from EAE mice.

FIG. 6, which includes FIG. 6A and FIG. 6B, provides graphs of cytokine production of CFA+MOG35-55 challenged mice.

FIG. 9A shows data for lymphocytes isolated from the peripheral lymph nodes from NOD mice treated with KGYY15 (grey) and control mice (black) and stained for cytokines. FIG. 9B shows data for lymphocytes isolated from the pancreatic lymph nodes from NOD mice treated with KGYY15 (grey) and control mice (black) and stained for cytokines. FIG. 9C shows data for lymphocytes isolated from the spleens from NOD mice treated with KGYY15 (grey) and control mice (black) and stained for cytokines. Bars show cytokine-positive cells within gated CD4+CD40+ cell populations (Th40), represented as a percentage. Data are from three individual mice from each group and are represented as the mean±SEM. *p<0.05, **p<0.01 by two-tailed unpaired t test.

FIG. 12A shows that KGYY6 improves glucose tolerance. FIG. 12B shows that KGYY6 improves insulin sensitivity. Graphs represent a statistically significant improvement in glucose tolerance (A; p<0.05) and insulin sensitivity (B; p<0.005). Graphs represent a statistically significant improvement in glucose tolerance (A; p<0.05) and insulin sensitivity (B; p<0.005).

FIGS. 14A-14C provide charts demonstrating that 15-mer peptide decreases fructosamine levels in T1D dogs. FIG. 14A shows that dog 15-mer peptide treatment significantly decreases fructoseamine levels in TID dogs. FIG. 14B shows that dog 15-mer peptide treatment significantly decreases fructoseamine levels in TID dogs. FIG. 14C shows the fold change observed in fructoseamine levels in in T1D dogs administered the dog 15-mer peptide treatment. Levels of fructoseamine were measured before the first infusion and several weeks after initiation of treatment.

FIG. 15A shows that a 15-mer peptide used to treat diabetic dogs was able to positively impact and help control blood glucose levels. FIG. 15B shows the same data as FIG. 15A but with the outlier in the treatment group removed.

DETAILED DESCRIPTION

Figure 1A:
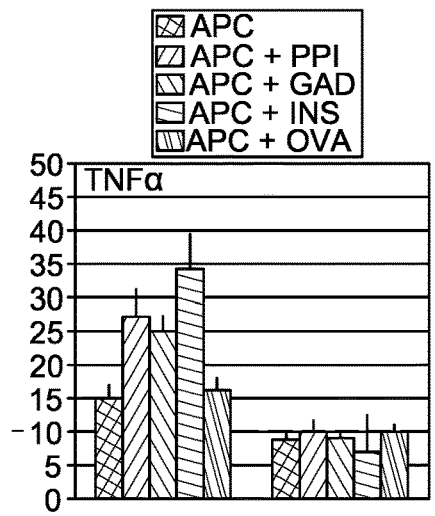
FIGS. 1A-1E provide graphs of how certain Th40 cells from T1D subjects respond to self-antigens when induced to make pro-inflammatory cytokines.
Figure 1C:
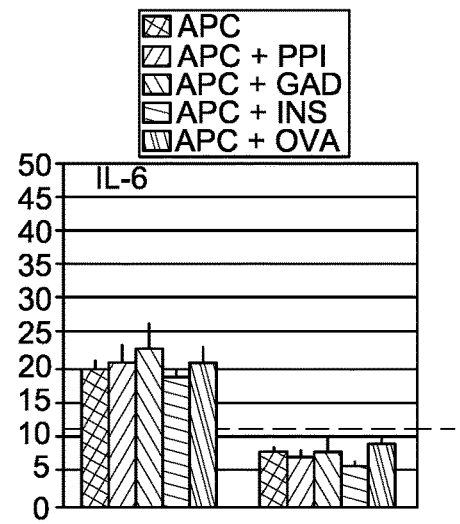
Figure 1B:
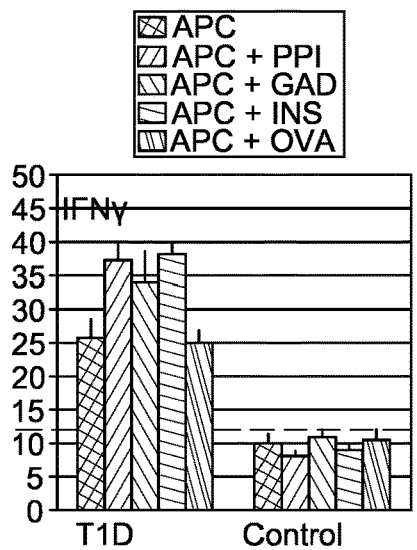
Figure 1D:
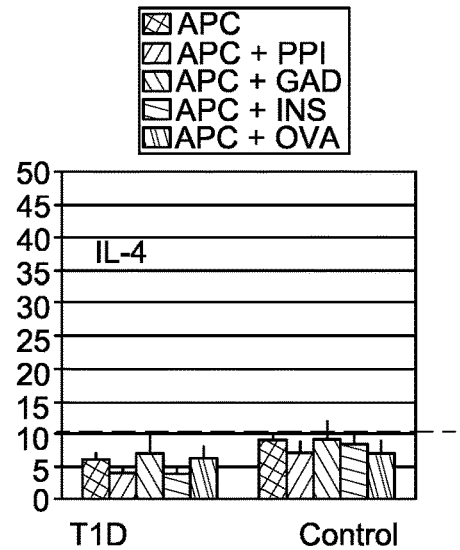
Figure 1E:
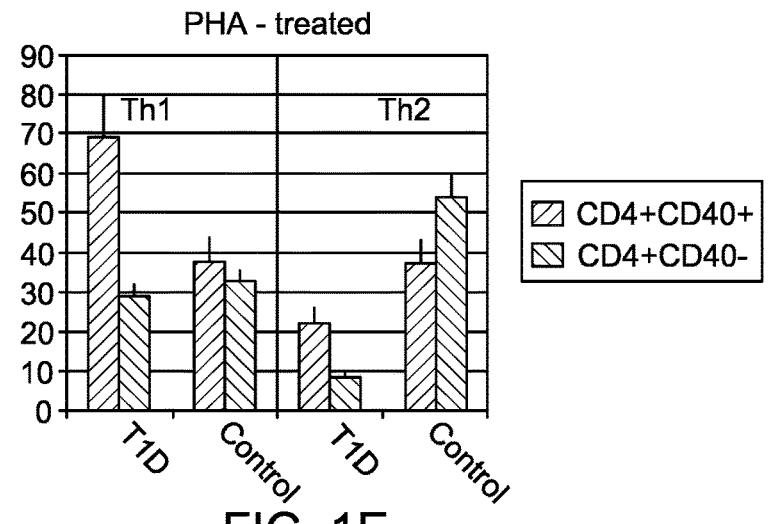

The developments hereof provide peptides and methods of treating subjects with cytokine release syndrome (CRS). As used herein, the phrase cytokine release syndrome (CRS) may mean any condition whereby a systemic inflammatory response syndrome (SIRS) is triggered by any factor, including but not limited to infections via viruses or bacteria, certain drugs, and physical trauma. The treatments described herein, therefore, may positively modulate or modify the levels or interactions of inflammatory cytokines, thus providing some relief to a patient that may be afflicted with the syndrome.

The developments hereof also provide peptides and methods of treating subjects with acute respiratory distress syndrome. As used herein, the phrase acute respiratory distress syndrome (ARDS) may include any condition whereby the subject suffers from alveolar capillary membrane injury. Alveolar capillary membrane injury may include any condition whereby the alveolar capillary membrane of a subject has reduced integrity or function. Moreover, in some implementations the treatments described herein, therefore, may increase the capacity of the injured alveolar membrane or it may completely restore lung compliance and the ability of the membrane to conduct gas exchange and/or fluid regulation and/or other vital functions of the alveolar capillary membrane. Moreover, the methods of this disclosure may act upon either the gas exchange conductance properties of the membrane or the fluid regulating properties of the membrane, or both.

Further, the methods hereof may be used to treat any condition or syndrome involving or causing alveolar capillary membrane injury. Examples of syndromes or conditions involving alveolar capillary injury include, but are not limited to, acute lung injury (ALI), acute respiratory distress syndrome (ARDS), infant respiratory distress syndrome (IRDS), traumatic brain injury (TBI), and neurogenic pulmonary edema (NPE). Some of the predisposing factors that contribute to ARDS may include infection, trauma, shock, lung trauma, surgery, drug reactions, drug overdose, transfusions, salt water inhalation, noxious gas or smoke inhalation, radiation, aspiration, pancreatitis, shock, and hyperoxia exposure. The possibilities are many and drivers and include new pre-disposing causes of alveolar capillary membrane injury as they are discovered. Regardless of the root cause of the membrane injury, these methods can be used to treat or prevent the alveolar membrane, and thus treat ARDS.

Before the present developments are further described, it is to be understood that these developments are not strictly limited to particular implementations described, as such may of course vary. It is also to be understood that the terminology used herein is for the purpose of describing particular implementations only, and is not intended to be limiting, since the scope of the present developments will be limited only by the claims.

It must be noted that as used herein and in the appended claims, the singular forms "a," "an," and "the" include plural referents unless the context clearly dictates otherwise. It should further be understood that as used herein, the term "a" entity or "an" entity refers to one or more of that entity. For example, a nucleic acid molecule refers to one or more nucleic acid molecules. As such, the terms "a," "an," "one or more," and "at least one" can be used interchangeably. Similarly, the terms "comprising," "including," and "having" can be used interchangeably.

Unless defined otherwise, all technical and scientific terms used herein have the same meaning as commonly understood by one of ordinary skill in the art to which these developments belong. Although any methods and materials similar or equivalent to those described herein can also be used in the practice or testing of the present developments, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present developments are not entitled to antedate such publication by virtue of prior invention. Further, the dates of publication provided may be different from the actual publication dates, which may need to be independently confirmed.

It is appreciated that certain features of the developments, which are, for clarity, described in the context of separate implementations, may also be provided in combination in a single implementation. Conversely, various features of the developments, which are, for brevity, described in the context of a single embodiment, may also be provided separately or in any suitable sub-combination. All combinations of the implementations are specifically embraced by the present developments and are disclosed herein just as if each and every combination was individually and explicitly disclosed. In addition, all sub-combinations are also specifically embraced by the present developments and are disclosed herein just as if each and every such sub-combination was individually and explicitly disclosed herein.

It is further noted that the claims may be drafted to exclude any optional element. As such, this statement is intended to serve as antecedent basis for use of such exclusive terminology as "solely," "only," and the like in connection with the recitation of claim elements or use of a "negative" limitation.

Furthermore, as used herein the term animal refers to a vertebrate, preferably a mammal, more preferably a human. Suitable mammals on which to use the methods of the present developments include but are not limited farm animals, sports animals, pets, primates, mice, rats, horses, dogs, cats, and humans. The term animal can be used interchangeably with the terms subject or patient.

As used herein, the term "treatment" means a procedure which ameliorates or prevents one or more causes, symptoms, or unwanted/untoward effects of CRS, ARDS, or alveolar capillary membrane injury in a subject or patient. Similarly, the term "treat" is used to indicate performing a treatment. Treatments described herein, can, but need not, cure the subject, i.e. remove the cause(s), or remove entirely the symptom(s) and/or unwanted/untoward effect(s) of CRS, ARDS, or alveolar capillary membrane injury on the abnormal condition of the subject. Therefore, a treatment may include treating a subject to attenuate symptoms of the illness or injury, the symptoms of which may include, but are not limited to, shortness of breath, tachypnea, or low blood pressure, or may include removing or decreasing the severity of the root cause of the abnormal condition or injury of the subject. Moreover, the treatment may also reduce signs of the distress or injury of the subject that may include hypoxia, hypoxemia, lung and systemic inflammatory and oxidative stress responses that contribute to lung and other organ dysfunction, including multiple organ failure.

As used herein, the terms "patient" and "a subject" and similar phrases, are intended to refer to subjects who have been diagnosed with CRS, ARDS, or alveolar capillary injury. The terms "Healthy subject", "non-CRS subject", "non-ARDS subject", "a subject who does not have CRS", "a patient who does not have ARDS", and similar phrases, are intended to refer to a subject who has not been diagnosed with CRS, ARDS, or alveolar capillary injury. A healthy subject has no other acute systemic disease.

As used herein, the term "sample" or "biological sample" includes a sample of any cell type or from any tissue or body fluid, body fluids including, but not limited to: cerebrospinal fluid (CSF), serum, plasma, blood, or fluid from any suitable tissue. In a preferred embodiment, the biological sample is blood or any component of blood (e.g., serum, plasma, etc.).

As used herein the term "administer," "administering," and "administration" is intended to mean introducing at least one compound into a subject. When administration is for the purpose of treatment, the compound or substance may be provided before, during, and/or after the onset of or progression of a symptom or sign of CRS, ARDS, and/or alveolar capillary membrane injury.

As used herein, a "symptom" is a subjective manifestation from the point of view of the patent, e.g. shortness of breath.

A "sign" on the other hand, is an objective, clinical manifestation that is often measurable or quantifiable, e.g. low blood oxygen levels or rapid respiratory rate or an abnormal chest x-ray. The therapeutic administration of compounds and peptides hereof may serve to attenuate any symptom or sign, or prevent additional symptoms or signs from arising. In at least some instances the substance or compound may be provided in advance of any visible or detectable symptom or sign of either alveolar capillary membrane injury, cytokine release syndrome, or acute respiratory distress syndrome. The prophylactic administration of the compounds and peptides hereof may serve to attenuate subsequently arising symptoms or signs or prevent symptoms or signs from arising altogether. For example, a specific peptide hereof, may be administered intravenously in an intensive care unit to individuals who are "at-risk" because of predisposing conditions and/or who have developing or established CRS or ARDS. In at least some instances, the developments hereof, contemplate the peptides hereof being administered to patients who may have contracted COVID-19 and thus have a risk of developing CRS or ARDS simply by their exposure and contraction of the viral illness. Alternatively, other implementations of the developments contemplate oral administration that may be used for mass casualty situations in which the peptide is given by first responders to individuals exposed to an insult as a matter of course.

Thus, the route of administration of the compounds and peptides hereof includes, but is not limited to, topical, transdermal, intranasal, intralung (insufflation or aerosolization), transmucosal, oral, subcutaneous, intravenous, intraarterial, intramuscular, intraosseous, intraperitoneal, epidural, and intrathecal administration.

The peptides, compounds, and methods hereof may be useful in decreasing the severity of CRS, ARDS, and/ alveolar capillary membrane injury directly and/or by decreasing factors such as CD40+ T cell mediated inflammation and/or hyperglycemia that contributes to ARDS.

Thus the treatment and prevention methods hereof include administering a therapeutically effective amount of peptides to subjects in need thereof. Peptides useful in these methods include a peptide that has a least a portion of the amino acid sequence of a CD154 protein such that the peptide interacts with CD40 protein in such a manner as to modulate, affect, interfere, block, change, or otherwise alter the interaction of a CD40 complex with CD154. These peptides may comprise 4, 5, 6, 7, 8, 9, 10, 11, 12, 13, 14, or 15 more contiguous amino acids from the human CD40 ligand (CD154), and interact with CD40 in such a manner as to modulate, affect, interfere, block, change, or otherwise alter the interaction. The peptides may in certain implementations may preferably include a core sequence of lysine-glycine-tyrosine-tyrosine (KGYY; SEQ ID NO: 3-see Table 1). These peptides may alternatively include at least one sequence selected from the group of SEQ ID NO: 4, 5, 6, 7, 8; SEQ ID NO: 27, 28, 29, 30; and SEQ ID NO: 32, 33, 34. These peptide sequences are set forth in the following Table 1:

TABLE 1

| SEQ ID NO | SEQUENCE | Description |
|---|---|---|
| 1 | MIETYSQPSP RSVATGLPA MKIFMYLLTV FLITQMIGSV LFAVYLHRR DKVEEEVNLH EDFVFIKKLK RCNKGEGSL LLNCEEMRRQ FEDLVKDITL NKEEKKENS EMQRGDEDPQ IAAHVVSEAN SNAASVLQ KKGYYTMKSN LVMLENGKQL TVKREGLYY YTQVTFCSNR EPSSQRPFIV GLWLKPSSG ERILLKAANT HSSSQLCEQQ SVHLGGVFE QAGASVFVNV TEASQVIHRV GFSSFGLLKL | SwissPro 27548.2 Mouse Ligand (CD154 Protein) |
| 2 | MIETYNQTSP RSAATGLPIS MKIFMYLLTV FLITQMIGSA LFAVYLHRRL DKIEDERNLH EDFVFMKTIQ RCNTGERSLS LLNCEEIKSQ FEGFVKDIML NKEETKKENS FEMQKGDQNP QIAAHVISEA SSKTTSVLQW AEKGYYTMSN NLVTLENGKQ LTVKRQGLYY IYAQVTFCSN REASSQAPFI ASLCLKSPGR FERILLRAAN THSSAKPCGQ QSIHLGGVFE LQPGASVFVN VTDPSQVSHG TGFTSFGLLK L | SwissPro 29965 Human CD40 Ligand (CD154 Protein) |
| 3 | KGYY | Core-sequence |
| 4 | AKKGYY | 6-mer |
| 5 | AKKGYYTM | 8-mer-mouse |
| 6 | AEKGYYTM | 8-mer human |
| 7 | VLQWAKKGYYTMKSN | 15-mer-mouse |
| 8 | VLQWAEKGYYTMSNN | 15-mer human |
| 9 | NAASVLQW AKKGYYTMKSNL VMLE | 24-mer mouse |
| 10 | ISQAVHAAHAEINEAGR | 15-mer from ovalbumin; control peptide |
| 11 | G-L-Q-W-A-K-K-G-Y-Y-T-M-K-S-N | Gly-1 |
| 12 | V-G-Q-W-A-K-K-G-Y-Y-T-M-K-S-N | Gly-2 |
| 13 | V-L-G-W-A-K-K-G-Y-Y-T-M-K-S-N | Gly-3 |
| 14 | V-L-Q-G-A-K-K-G-Y-Y-T-M-K-S-N | Gly-4 |
| 15 | V-L-Q-W-G-K-K-G-Y-Y-T-M-K-S-N | Gly-5 |
| 16 | V-L-Q-W-A-G-K-G-Y-Y-T-M-K-S-N | Gly-6 |
| 17 | V-L-Q-W-A-K-G-G-Y-Y-T-M-K-S-N | Gly-7 |
| 18 | V-L-Q-W-A-K-K-G-G-Y-T-M-K-S-N | Gly-9 |
| 19 | V-L-Q-W-A-K-K-G-Y-G-T-M-K-S-N | Gly-10 |
| 20 | V-L-Q-W-A-K-K-G-Y-Y-G-M-K-S-N | Gly-11 |
| 21 | V-L-Q-W-A-K-K-G-Y-Y-T-G-K-S-N | Gly-12 |
| 22 | ISQAVHAAHAEINEAGR | 15-mer from ovalbumin; control peptide |
| 23 | YVQGKANLKSKLMYT | Scrambled peptide |
| 24 | WAKKGYYTMK | 10-mer mouse |
| 25 | VLQWAKKGYYTMK | 13-mer mouse |
| 26 | AASVLQW AKKGYYTMKSNL VMLEN | 24-mer mouse |
| 27 | KGYYTM | 6-mer (Form 2) human |
| 28 | AEKGYY | 6-mer (Form 3) human |
| 29 | AKKGYY | 6-mer (Form 4) mouse |
| 30 | AKGYYT | 6-mer (Form 5) synthetic |

TABLE 1-continued

| SEQ ID NO | SEQUENCE | Description |
|---|---|---|
| 31 | YKNVKQMAYWLTGKS | Scrambled peptide |
| 32 | VLRWA PKGYY TISSN | 15-mer-Form 3 |
| 33 | VLQWA PKGYY TISSN | 15-mer-Form 4 |
| 34 | VLQWA QKGYY TISNN | 15-mer-Form 5 |
| 35 | YGRKKRRQRRR | TAT |
| 36 | XGRKKRRQRRR | TAT variant-where X is an amino acid other than Y |
| 37 | GRKKRRQRRR | I TAT variant |

The peptides may often have sequences that are entirely responsible for the interaction of the peptide with a CD40 protein; however, the peptides hereof may additionally contain amino acid sequences that do not interact with a CD40 protein as they may have other useful functions as well. For example, in addition to the amino acid sequence responsible for interacting with a CD40 protein, a peptide of the present invention can contain amino acid sequences that are useful for visualizing or purifying the peptide. Such sequences act as labels (e.g., enzymes) or tags (antibody binding sites). Examples of such labels and tags include, but are not limited to, B-galactosidase, luciferase, glutathione-s-transferase, thioredoxin, HIS-tags, biotin tags, and fluorescent tags. Other useful sequences for labeling and tagging proteins are known to those of skill in the art.

Likewise, peptides of the present invention can be modified, so long as such modification does not significantly affect the ability of the peptide to treat CRS, ARDS, or alveolar capillary membrane injury. Such modifications can be made, for example, to increase the stability, solubility or absorbability of the protein. Examples of such modifications include, but are not limited to pegylation, glycosylation and chemical modification of the peptide.

Peptides hereof may be formed as a fusion with another peptide that may enhance one or more properties of the peptide. In one version, the peptide may be fused to another peptide that imparts favorable pharmacokinetic characteristics to the peptide. In another example, the peptide may be fused with a peptide that enhances the intracellular transport of the therapeutic peptide. Examples of these peptides may include TAT derived from HIV, antennapedia derived from Drosophilia, VP22 from herpes simplex virus, complementary-determining regions (CDR) 2 and 3 of anti-DNA antibodies, 70 KDa heat shock protein, and transportan. For example, in at least one implementation the HIV internalization peptide YGRKKRRQRRR (SEQ ID NO: 35) may be utilized. Other known variants of this sequence may also be further implemented to confer some additional properties to be used with the peptide. Additional peptides such as XGRKKRRQRRR (SEQ ID NO: 36), where X is an amino acid other than Y may also be utilized in this manner, thus for example GRKKRRQRRR (SEQ ID NO: 37) is a variant of a peptide that may be used as a TAT variant in implementations hereof.

Also contemplated in the context of the methods and compositions hereof is the alteration of the therapeutic peptides by chemical or genetic means. Examples of this type of alteration or modification may include the construction of peptides of partial or complete sequences with non-natural amino acids in L or D enantiomeric forms.

Accordingly, any of the peptides hereof and disclosed herein, and any variants, thereof could be produced in all-D form. Additionally, the peptides hereof may be further modified to contain carbohydrate or lipid moieties, such as sugars or fatty acids, covalently linked to the side chains of the N- or C-termini of the amino acids. Furthermore, the peptides may be additionally altered or enhanced by glycosylation and/or phosphorylation. Likewise, the peptides hereof may be acetylated or amidated at N- or C-termini as this may confer desirable properties or characteristics to the peptide.

In addition to the alterations, modifications, and enhancements previously described, the peptides hereof may be modified to enhance solubility and/or half-life upon being administered. For example, polyethylene glycol (PEG) and related polymers may be used to stabilize the peptide and extend the half-life of the peptide in the blood or patient tissue. A variety of PEG enhancements and modifications are contemplated hereby including two PEG side chains linked via the primary amino groups of a lysine. Moreover, a peptide hereof may be modified by acetylation on the N-terminus and/or amidation on the C-terminus, which may be used to stabilize the peptide.

In yet another implementation, the peptides hereof may be linked to one or more domains of an Fc region of mouse, human, canine, feline, or equine, IgG immunoglobin, or the equivalent in each species, and/or may be linked to an epitope tag polypeptide comprising between 6 and 50 amino acid residues. In some instances, the peptides and proteins fused to an Fc region have been observed to exhibit substantially greater half-life in vivo than the unfused counterpart. Additionally, a fusion to an Fc region may allow for dimerization/multimerization of the fusion polypeptide. The Fc region may a naturally occurring Fc region, or may be altered to improve certain qualities, including but not limited to therapeutic qualities, circulation time, and reduced aggregation.

In some implementations, the peptides hereof may also be modified to contain, conjugated to, and/or administered with phosphorus, sulfur, manganese, magnesium, calcium, halogens, metals, etc. Amino acid mimics may be used to produce polypeptides, and therefore, the polypeptides of this disclosure may include amino acids mimics that have enhanced properties, such as resistance to degradation.

The peptides and methods hereof may also comprise administering pro-drugs that metabolize to an active form of these peptides. As used herein, a "pro-drug" is a compound that a biological system metabolizes to an active compound as a result of spontaneous chemical reaction(s), enzyme catalyzed reaction(s), and/or metabolic chemical reaction(s), or a combination of each. Standard prodrugs are formed using groups attached to functionality, e.g. HO—, HS—, HOOC—, R2N—, associated with the drug, that cleave in vivo. Standard prodrugs include, but are not limited to, carboxylate esters where the group is alkyl, aryl, aralkyl, acyloxyalkyl, alkoxycarbonyloxyalkyl as well as esters of hydroxyl, thiol and amines, where the group attached is an acyl group, an alkoxycarbonyl, aminocarbonyl, phosphate or sulfate. The groups illustrated are exemplary and not exhaustive, and one skilled in the art could prepare other known varieties of prodrugs. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved bioavailability, pharmacodynamic half-life, etc.

The methods of treatment hereof may include co-administering the peptides with a least one additional compound. The term "co-administer" indicates that each of at least two compounds is administered during a time frame wherein the respective periods of biological activity or effects overlap, but they need not be administered simultaneously. Thus, the term "co-administer" includes sequential as well as co-extensive administration of the compounds of the present developments. Similar to "administering," "co-administering" of more than one substance may be for therapeutic and/or prophylactic purposes. If more than one substance is co-administered, the routes of administration of the two or more substances need not be the same. In one specific implementation, the peptide is co-administered with a derivative of L-ergothioneine, N-acetylcysteine (NAC), an organoselenium, a thiol-yielding compound, a glutathione enhancing compound and/or alpha-lipoic acid. The development contemplates the possibility of administering a variety of agents alone and/or in combination with the peptide in any order and by any means. The scope of the developments are not limited by the identity of the substance which may be co-administered.

In yet another implementation of treatment hereof, the peptides may be provided as a sterile solution in 10 mM acetate buffer, in 5% glucose, in water. In this implementation the pH may be approximately 5.5. The peptide in at least one implementation will be provided as a sterile solution in 10 mM acetate buffer, in 5% glucose in water, pH 5.5, 5 mL at 20 mg/mL, 100 mg/vial. On the day of administration, the product will be diluted in saline to result in 50 mL for intravenous (IV) infusion over 30 minutes. The developments hereof further contemplate using alternative buffer systems that may facilitate efficacious delivery and treatment with the peptide.

One property of the inhibitor peptides provided herein may be that they decrease hyperglycemia during ARDS development. Thus the methods hereof may include treating or preventing hyperglycemia in a subject by administering to the subject a composition comprising a peptide of any one of SEQ ID NOs: 4, 5, 6, 7, 8; SEQ ID NO: 27, 28, 29, 30; and SEQ ID NO: 32, 33, 34, and functional fragments and/or analogs thereof, in an amount and under conditions effective to prevent hypoglycemia. Thus, these methods may include the treatment of both non-diabetic and diabetic subjects.

The methods hereof may also include the treatment of a subject developing ARDS or suspected of developing ARDS and/or at risk of developing ARDS in order to decrease or prevent hyperglycemia associated with developing ARDS that may exacerbate or intensify the severity or rate of developing ARDS. In these methods, the blood glucose levels of the subject may be reduced to less than 140 mg/dl, or less than 120 mg/dl, or less than 110 mg/dl. In these methods the blood glucose levels of the subject may be maintained greater than 80 mg/dl, or greater than 90 mg/dl, or greater than 100 mg/dl. It should be recognized that these methods are not limited only to treating CRS or ARDS but may also be useful in reducing hyperglycemia in the treatment of toxemia, inflammation, infection, bacteremia, sepsis, septic shock, acute lung injury, severe acute respiratory syndrome (SARS), systemic inflammatory response syndrome (SIRS), or multiple organ dysfunction syndrome (MODS).

It is contemplated hereby, that the peptide and other compounds may be potentially used to pretreat large numbers of potentially exposed individuals before symptoms of CRS or ARDS develop. Practically, a major concern arises if thousands of individuals are exposed simultaneously and unexpectedly to a virus such as COVID-19, that not enough ICU beds and diagnostic tests would be available to afflicted individuals in a timely manner. Thus the methods and compositions of this disclosure provide a potentially safe and reasonable approach at mitigation CRS and ARDS and other serious illnesses following a mass tragedy. These peptides and/or other compounds may even be given by first responders and given to first responders in non-clinical settings to prevent the development of CRS and ARDS.

When administered or co-administered, the compounds of the present developments are given in a therapeutically effective amount to the subject. As used herein, the phrase "therapeutically effective amount" means an amount that has any beneficial effect in treating the syndrome (CRS or ARDS), condition, or alveolar membrane injury. Determining the therapeutically effective amount of the active compound of the peptides of the present development may depend on such factors, including but not limited to, the extend to the condition, syndrome or injury to be treated, the age and condition of the subject to be treated, and other factors that may be considered by a prescribing physician. Determining the therapeutic index of the active compounds may be a matter of routine optimization and titration in the art. The term "therapeutic index" or "therapeutic window" refers to the ratio of the dose of a drug or pro-drug that produces a therapeutically beneficial response relative to the does that produces an undesired response, such as death, an elevation of markers that are indicative of toxicity, and/or pharmacological side effects.

The peptides used and utilized in the methods may be administered to the subject in a pharmaceutically acceptable carrier, adjuvant, or vehicle. Select examples of pharmaceutically acceptable carriers, adjuvants, and vehicles, which are well-known in the art are disclosed in Remington: The Science and Practice of Pharmacy, 2ist Ed., Hendrickson, R., et al., Eds., Lippincott Williams & Wilkins, Baltimore, Md. (2006). The selection of a pharmaceutically acceptable carrier, adjuvant, or vehicle will depend on a variety of factors including but not limited to, the route of administration, dosage levels, the age, weight and/or condition of the subject, etc.

The pharmaceutical compositions may be adapted for administration by any appropriate route, for example by oral (including buccal and sublingual), nasal, rectal, intratracheal, aerosol, topical, transdermal, parenteral, subcutaneous, intramuscular, intravenous, or intradermal routes. Such compositions may be prepared by any method known in the art of pharmacy, for example, by admixing the active ingredient with carrier(s) or excipient(s) under sterile conditions. Such compositions may also include liposomal compositions as drug carriers.

In implementations where the pharmaceutical compositions hereof are adapted for nasal, intratracheal, or aerosolized delivery and administration, the carrier may be a solid and may include a coarse powder having a particle size, for example, in the nanometer range up to the micron range. Additionally, particles may range from about 20 to 500 microns and may be administered via rapid inhalation through the nasal passage from a container of the powder that is held close up to the nose. Suitable compositions wherein the carrier is a liquid for administration as nasal spray or nasal drops may include aqueous or oil solutions of the active ingredient.

In yet another implementation, pharmaceutical compositions may be adapted for inhalation via fine dusts or mists that may be generated by means of various type of metered dose pressurized aerosols, supercritical fluid aerosolization, nebulizers, or insufflators.

In yet another implementation, pharmaceutical compositions adapted for parenteral administration include aqueous and non-aqueous sterile injection solution which may contain antioxidants, buffers, bacteriostats, and solutes which render the formulation substantially isotonic with the blood of the intended recipient; and aqueous and non-aqueous sterile suspensions which may include suspending agents and thickening agents. Excipients which may be used for injectable solutions include water, alcohol, polyols, glycerin, and vegetable oils, for example. The compositions may be presented in unit-dose or multi-dose containers, for example, in sealed ampoules and vials, and may be stored in freeze-dried (lyophilized) condition requiring only the addition of sterile liquid carrier, for example water for injections, immediately prior to use. Extemporaneous injection solutions and suspensions may be prepared from sterile powders, granules, and tablets. The pharmaceutical compositions may contain preserving agents, solubilizing agents, stabilizing agents, wetting agents, emulsifiers, sweeteners, colorants, odorants, salts (substances of the present developments may themselves be provided in the form of a pharmaceutically acceptable salt), buffers, coating agents, or antioxidants. Salts may include acetate salts, hydrochloride salts, sodium chloride salts, or other salts acceptable and useful for the delivery of the peptide.

Markers of CRS, ARDS, and alveolar capillary membrane injury may be known in the art and include but are not limited to the presence of inflammatory cytokines. Examples, of inflammatory cytokines may include, but are not limited to, interleukin-1 (IL-1), interferon gamma (IFNγ), tumor necrosis factor alpha (TNFα), and interleukin-8 (IL-8). Assaying for specific cytokines may be well known in the art and may include assays such as ELISA assays, Northern blots, Western blots, activity assays, and the like. Other markers of CRS, ARDS, and alveolar capillary membrane injury may include, but are not limited to, changes in blood pressure, increased number of lung neutrophils, increased levels of lung GSSG, increased concentration of expired H202, increased levels of lactate dehydrogenase (LDH) and a lung leak index. Other markers can be assayed using morphological assays of lung injury, physiologic derangements including measurements of hypoxia, and abnormalities of including GSH depletion, alterations of GSH/GSSG ration, increased measurements of oxidative stress, e.g. increased levels of 8-iso-PGFa. IL-6 is also recognized as being associated and indicative of CRS and/or ARDS. Assays for measuring each of the markers of CRS, ARDS, and alveolar capillary membrane injury may be known in the art.

The following examples are provided for purpose of illustration and are not intended to limit the scope of the present invention.

EXAMPLES

Example 1

FIG. 1, which includes FIG. 1A to FIG. 1E, demonstrates that Th40 cells from T1D subjects respond to diabetes self-antigens and are induced to make pro-inflammatory cytokines. Percent of CD4+CD40+ T cells expressing: TNFα (A); IFNγ (B); the pro-inflammatory cytokine IL-6 (C); and the anti-inflammatory Th2 cytokine, IL-4 (D). Dashed line represents, background levels of cytokine+ T cells. T cells from T1D and control subjects were challenged with PHA, a TCR non-specific mitogen and compared for Th1 (IFNγ) versus Th2 (IL-4) cytokine production for 18 h. Graphs represent percentage of cells producing each cytokine (E). Data represent an average from T cells of four T1D and four control subjects. For analysis, samples were gated on CD4loCD40+ or CD4hiCD40- and levels of cytokine are reported from each subset. Levels reported are above isotype controls within each subset.

Example 2

FIG. 2 which includes FIGS. 2A and 2B demonstrates that memory phenotype Th40 cells from MS patients produce both IL-17 and IFNγ. Total blood lymphocytes were stained and gated for CD4 and CD45RO expression to delineate memory cells. (A) Within that population Th40 cells were assayed for IFNγ and IL-17 production by intra-cellular staining. Levels of IL-17 and IFNγ were determined above isotype controls. Cells were examined immediately ex vivo. (B) Graph represents levels of IFNγ only, IL-17 only and IFNγ/IL-17 double positive cells from 11 RRMS subjects. Statistics were done by ANOVA, Tukey comparison, using the Graph Pad Prism program.

Example 3

Figure 3A:
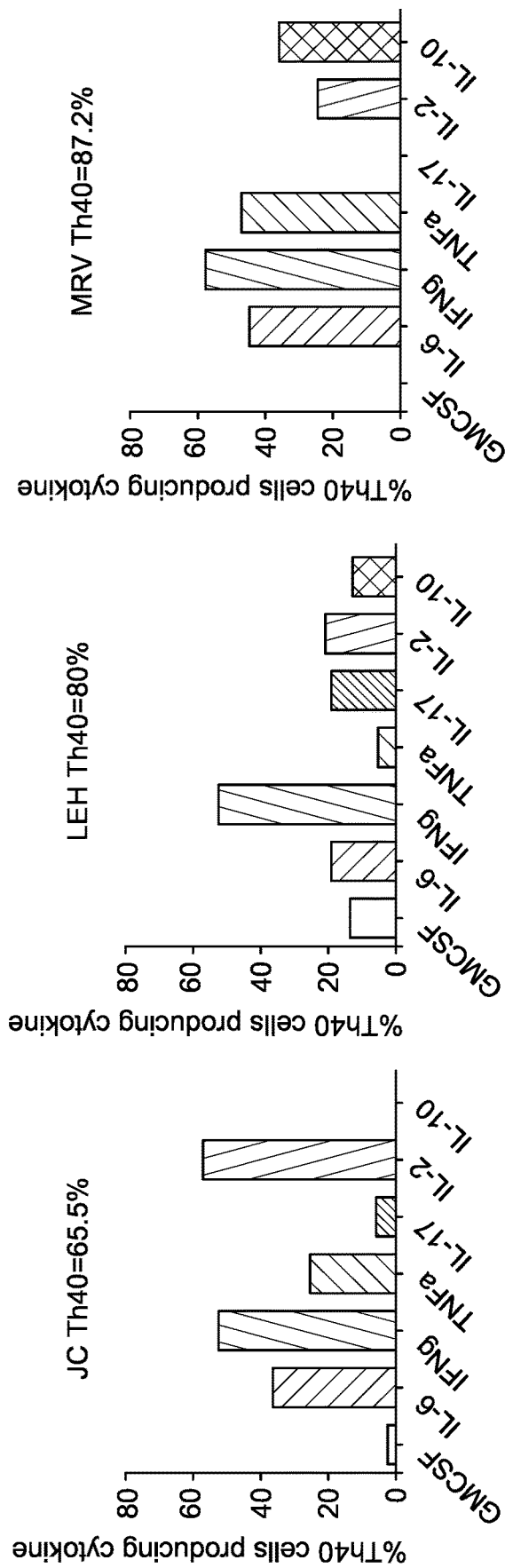
FIGS. 3A-3C provide graphs and charts of Th40 cells producing specific inflammatory cytokines.
Figure 3B:
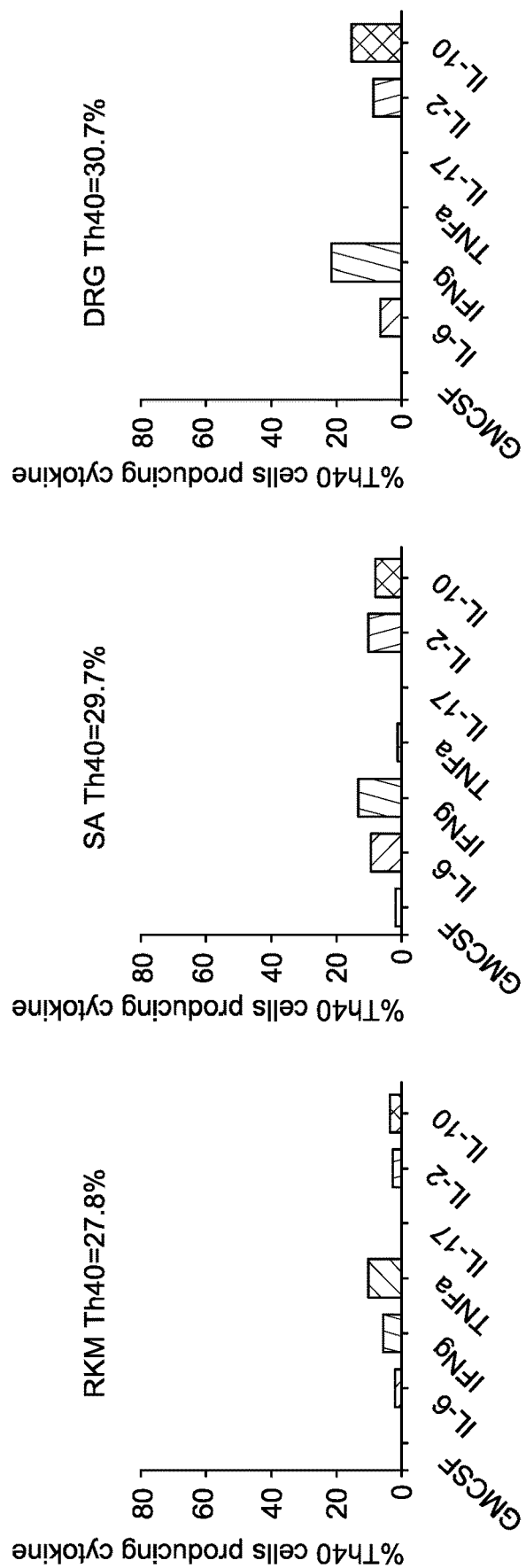
Figure 3C:
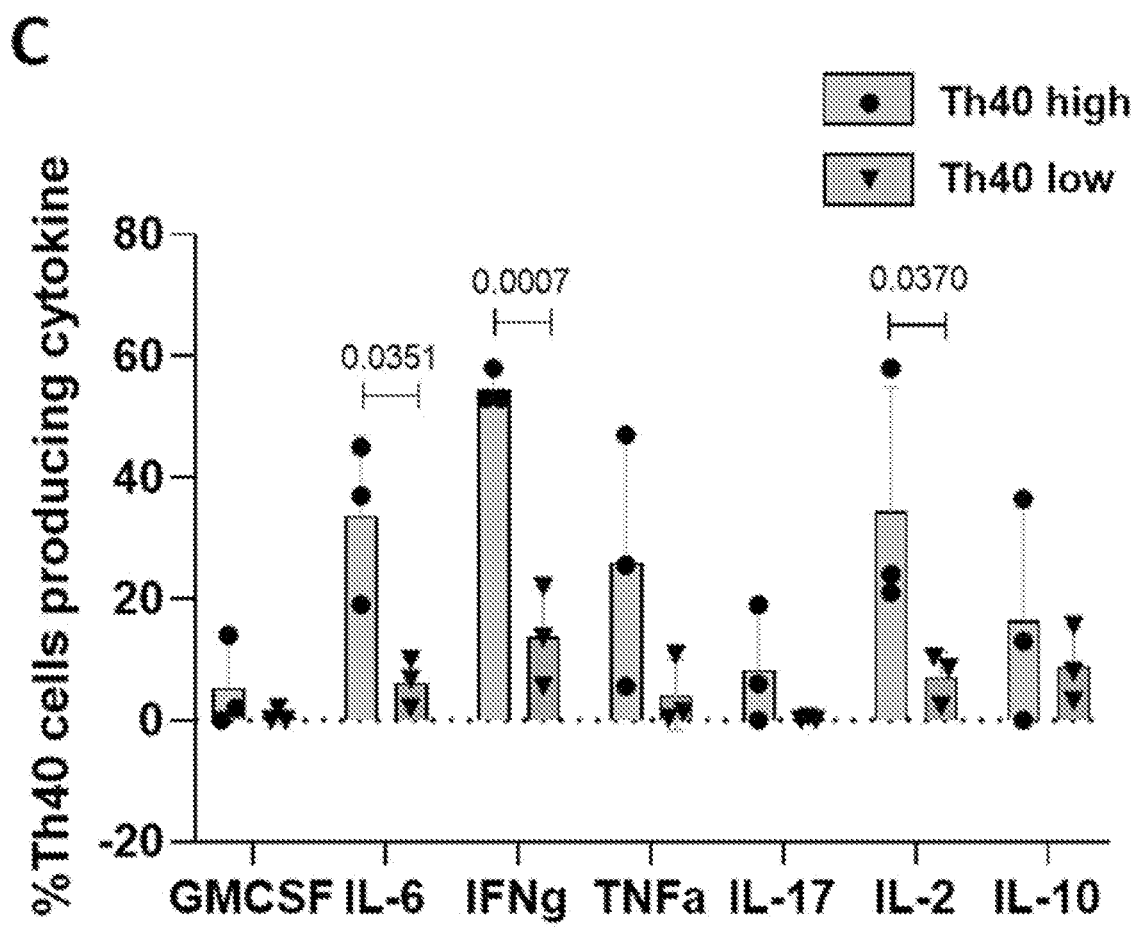
Figure 4A:
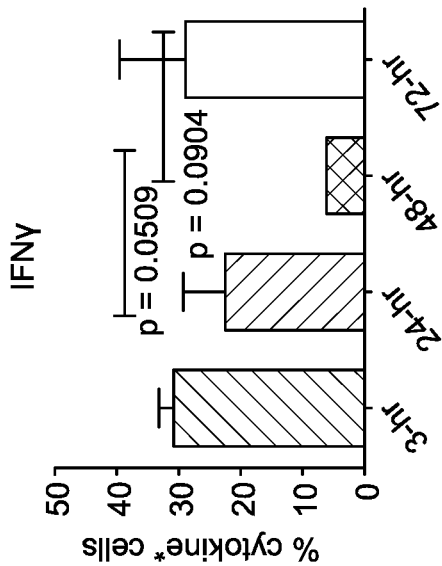
FIGS. 4A-4D provide graphs of cytokine levels in CD4+ and Th40 from brain cells of CA/CPR mice.
Figure 4B:
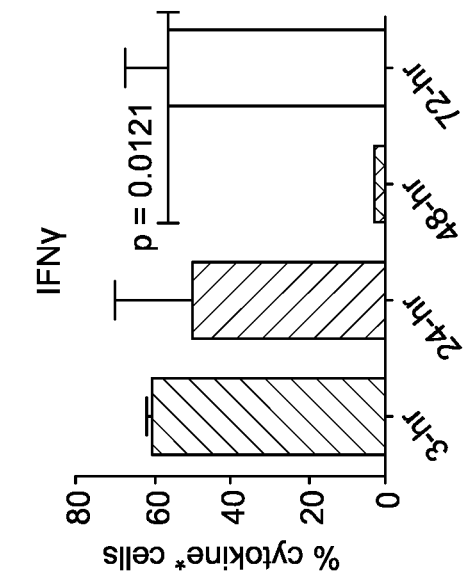
Figure 4C:
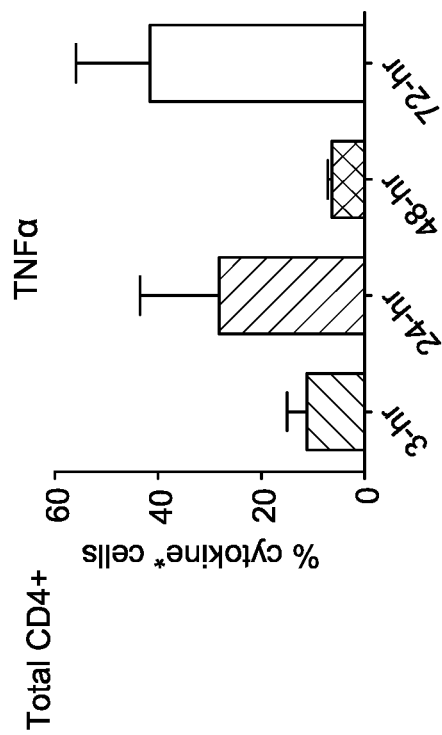
Figure 4D:
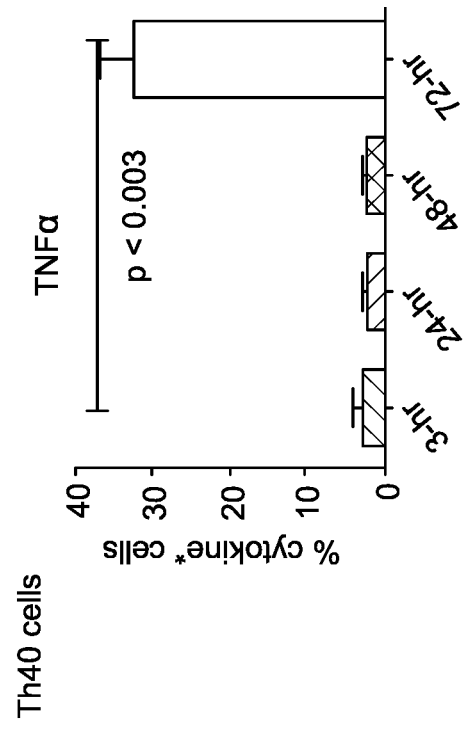

FIG. 3 includes sub-parts FIGS. 3A, 3B, and 3C. FIG. 3 includes data on MS patients with high Th40 cell levels in peripheral blood express inflammatory cytokines. Purified peripheral blood lymphocytes from MS patients with high (A) or low (B) Th40 cell levels were stained for CD3, CD4, CD40 and intracellularly for different cytokines then analyzed by flow cytometry. Cells were gated on CD4 versus CD40 and CD3 expression was confirmed for Th40 cells then cytokine expression was analyzed within the Th40 population. (C) Graphic representation and statistical analysis. IL-6, IFNγ and IL-2 were statistically different between Th40 high and Th40 low (Two-way ANOVA with Sidak's multiple comparisons test).

Example 4

FIG. 4 provides several graphs showing the cytokine production from lymphocytes in brains of CA/CPR mice. Lymphocytes were isolated from CA/CPR induced mice at 3 hr., 24 hr., 48 hr. and 72 hr. post injury. Cells were stained intracellularly for the Th 1, pro-inflammatory cytokines TNFα and IFNγ. FIGS. 4A and 4B show cytokines in total CD4+ T cells; FIGS. 4C and 4D show cytokines in the Th40 subset of CD4+ cells.

Example 5

Figure 5:
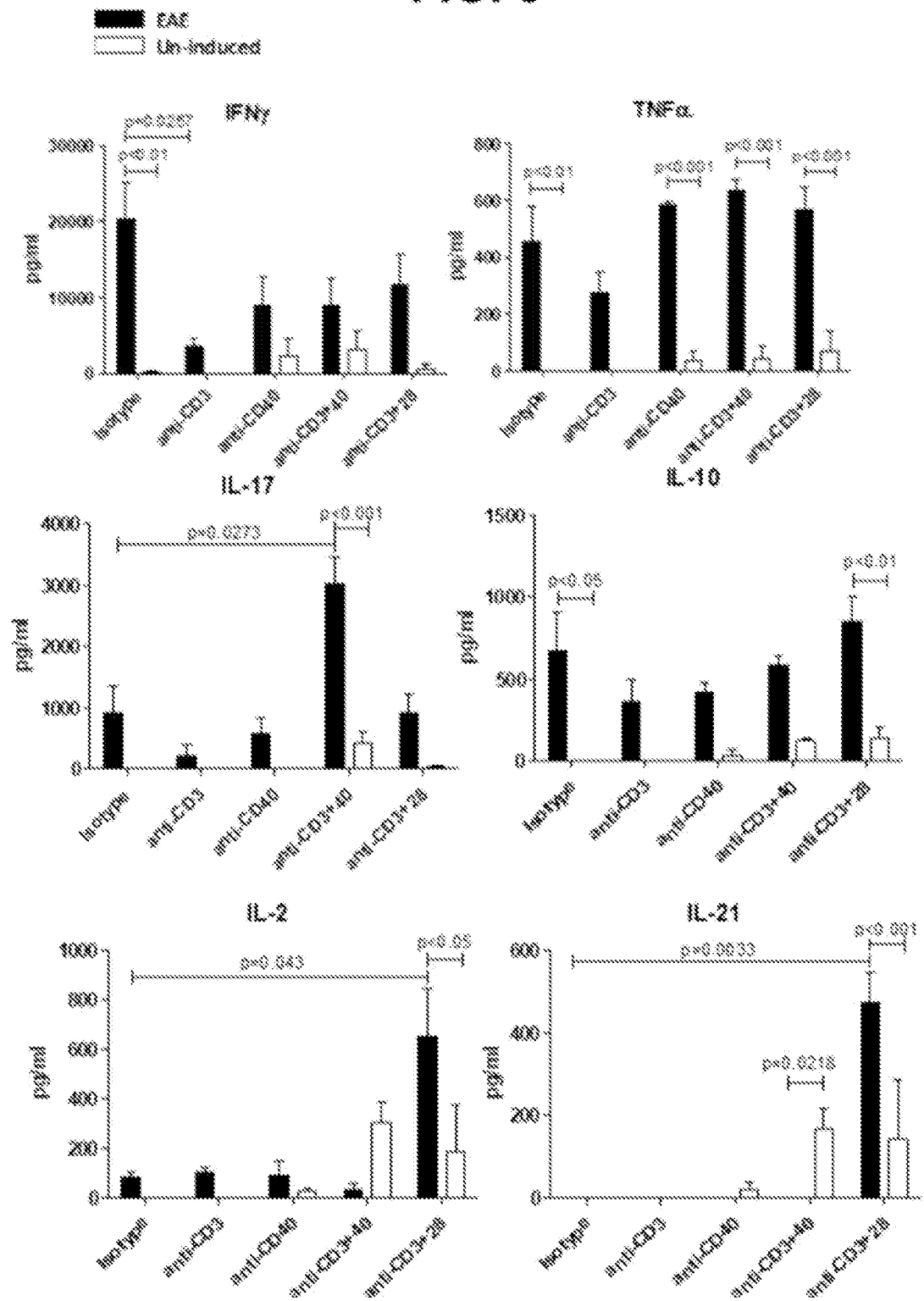

FIG. 5 provides several graphs showing that draining lymph nodes (dLN) lymphocytes from EAE mice secrete high levels of IFNγ. dLN were isolated from control (n=2) and EAE induced mice (10 days post-EAE-induction; n=3; EAE scores 2, 2, and 0) and lymphocytes purified. Lymphocytes were cultured in the absence/presence of CD3, CD28, and CD40 stimulation for 5 days. Cytokines in the supernatant were assayed. There were significant differences in cytokine production between lymphocytes from EAE and control mice (Two-way ANOVA) as well as between stimulated and isotype treated EAE lymphocytes (two-tailed t-test).

Example 6

Figure 6A:
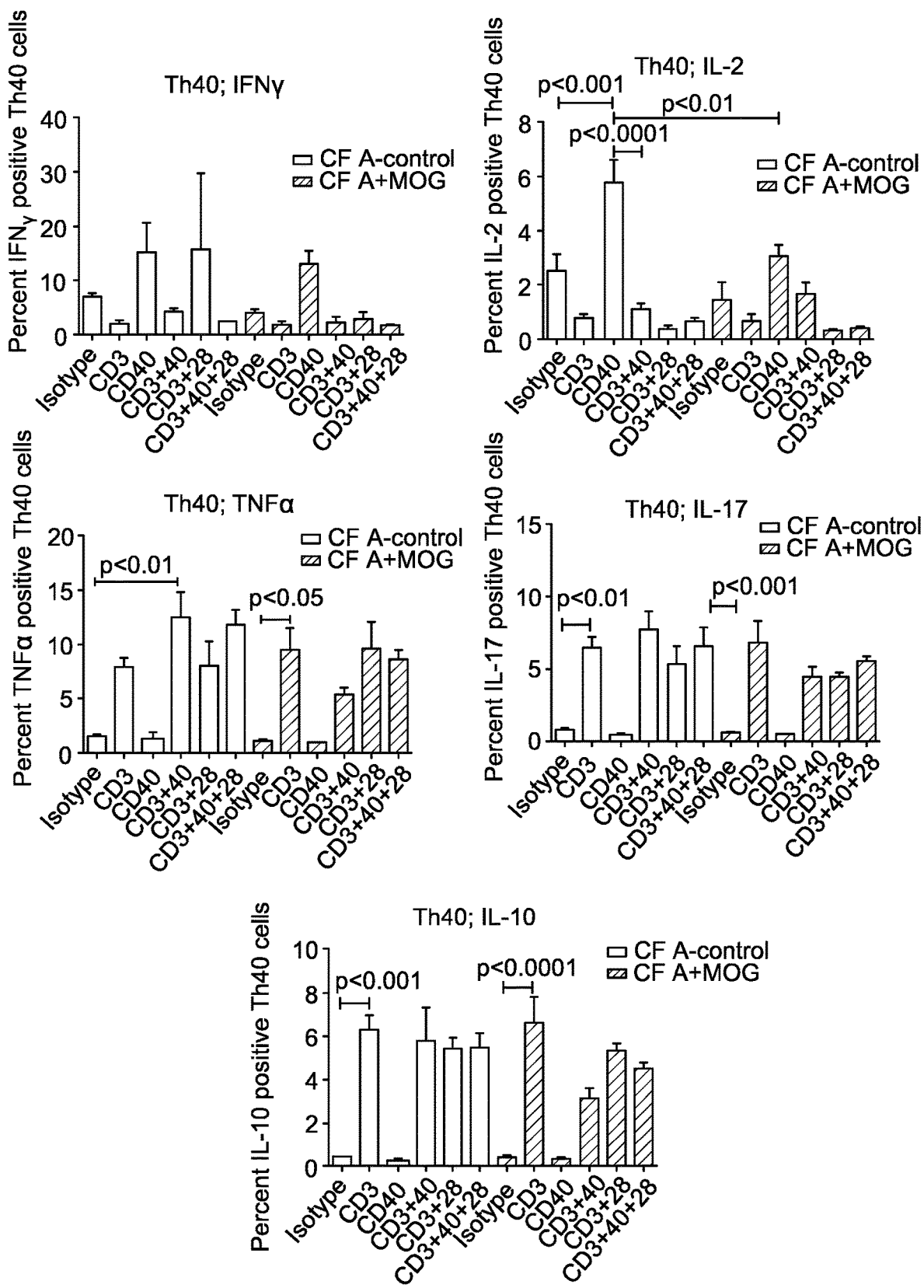
FIG. 6A shows cytokine production by Th40 cells from CFA-control and Th40 cells from CFA+MOG challenged mice.
Figure 6B:
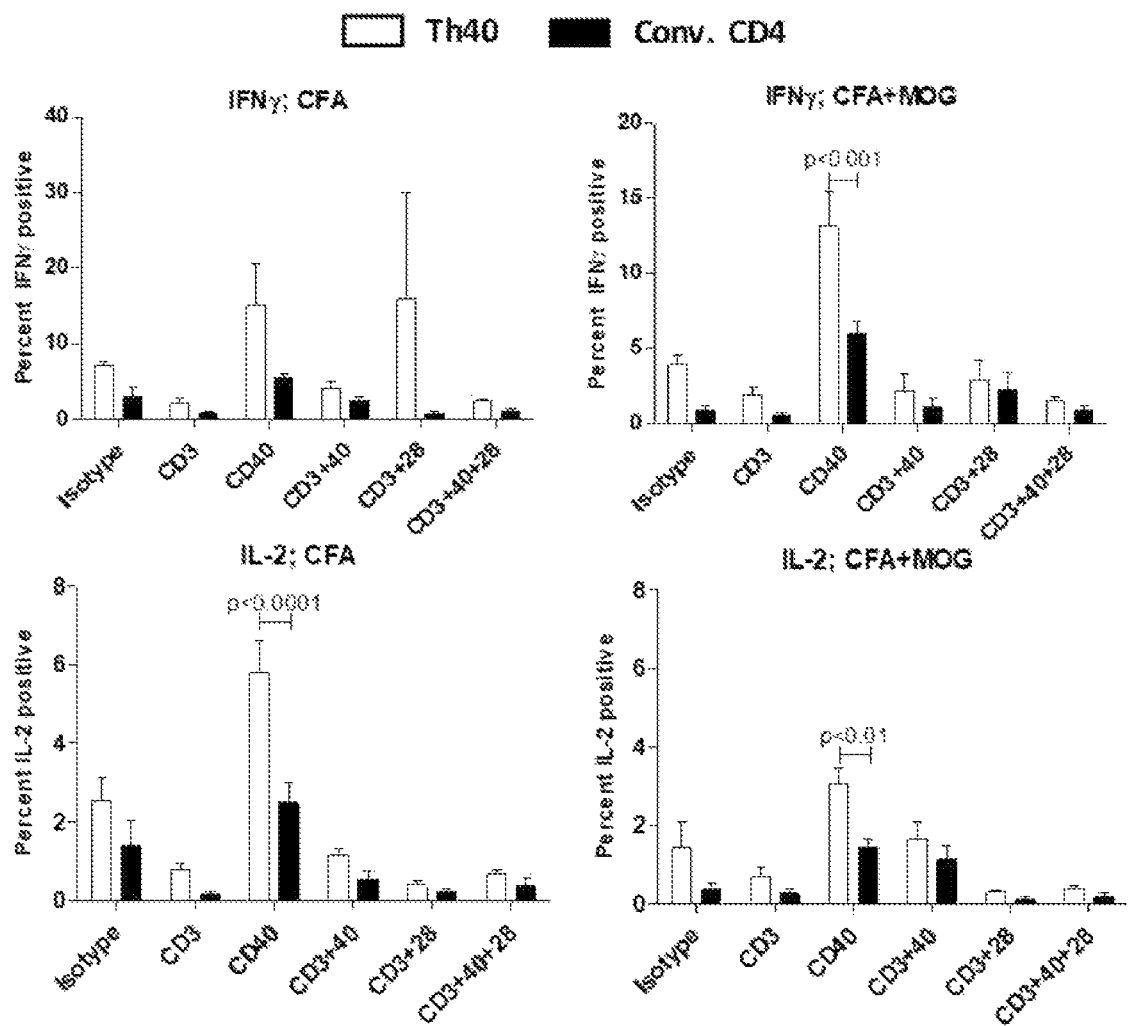
FIG. 6B compares cytokine production by Th40 cells to cytokine production by conventional CD4 T cells within either CFA-control (left) or CFA+MOG (right) generated cells. Statistical differences in A were calculated by One-Way ANOVA with Bonferroni post-test. Statistical differences in B were calculated by Two-Way ANOVA.
Figure 6B:
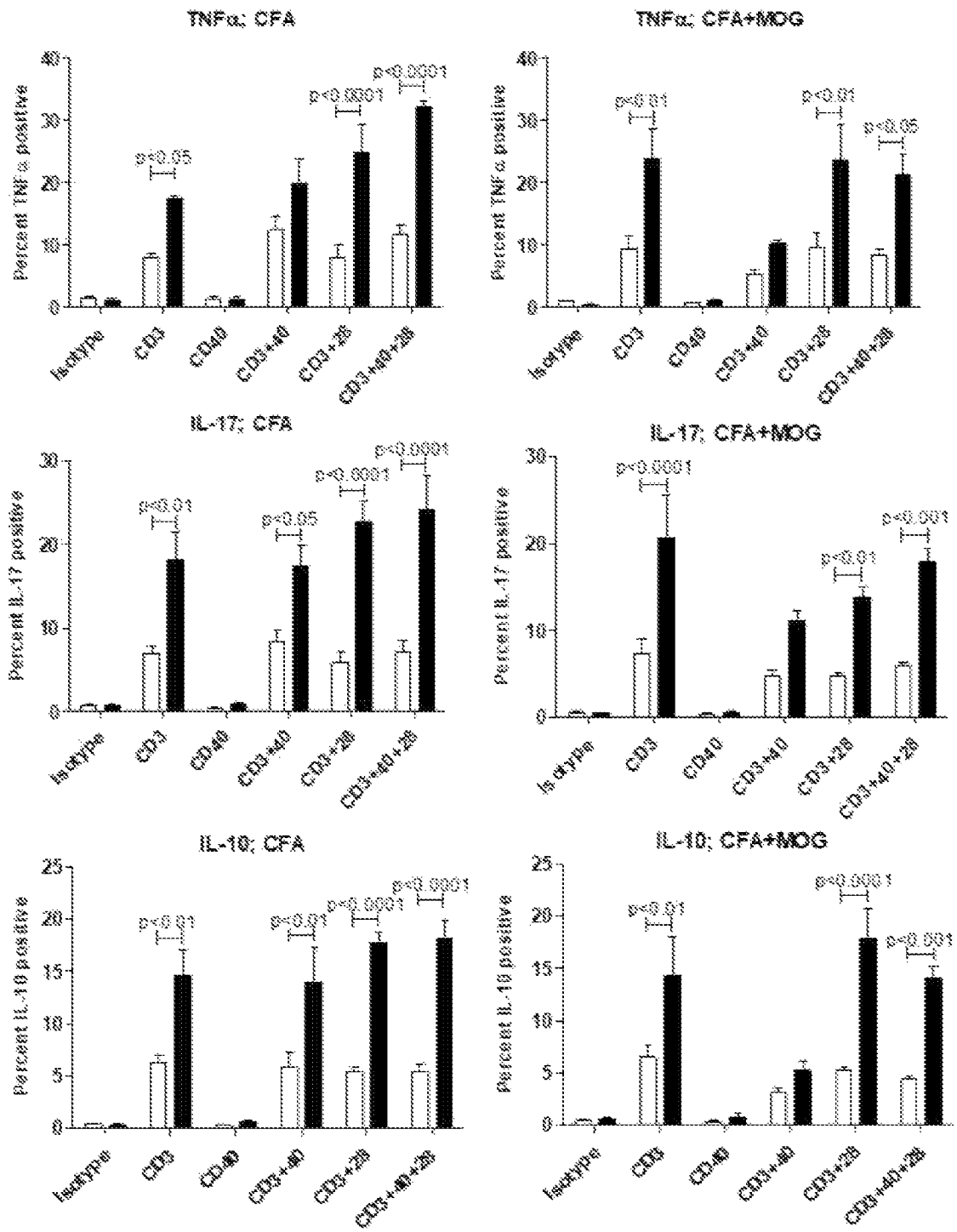

FIG. 6 which includes FIG. 6A and FIGS. 6B-1 and 6B-2, demonstrates that T cells from CFA-control challenged mice have a similar cytokine production potential compared to those from CFA+MOG35-55 challenged mice. dLN lymphocytes were purified from CFA-control and CFA+MOG challenged mice, 12 days after challenge, then the cells were cultured in the absence/presence of CD3, CD28, and/or CD40 stimulation or cultured with isotype antibodies for 3 days. Brefeldin A was added the last 2 hours, then the cells were stained for CD3, CD4, CD40, as well as for different cytokines (intracellularly). Cells were gated on CD4+CD40+(Th40) and CD4+CD40− (Cony. CD4; CD3 expression was confirmed in both populations) then cytokine levels were assessed. Gates were set from isotype controls. (A) Graphs depicting cytokine production by Th40 cells from CFA-control and Th40 cells from CFA+MOG challenged mice. ((B1-B2)) Graphs comparing cytokine production by Th40 cells to cytokine production by conventional CD4 T cells within either CFA-control (left) or CFA+MOG (right) generated cells. Statistical differences in A were calculated by One-Way ANOVA with Bonferroni post-test. Statistical differences in B were calculated by Two-Way ANOVA

Example 7

Figure 7:
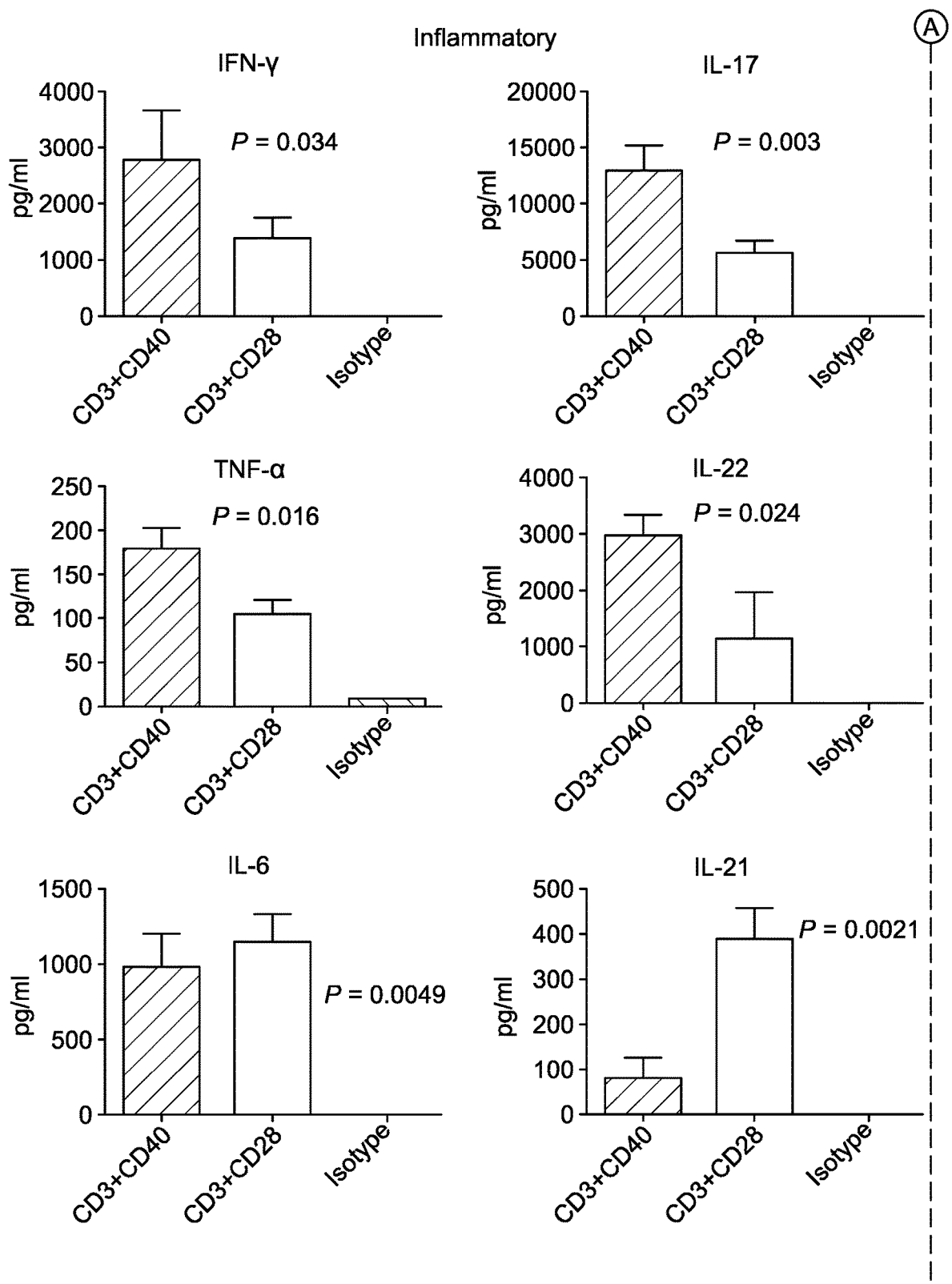
FIG. 7 provides several graphs of cytokine production in Th40 cells.
Figure 7:
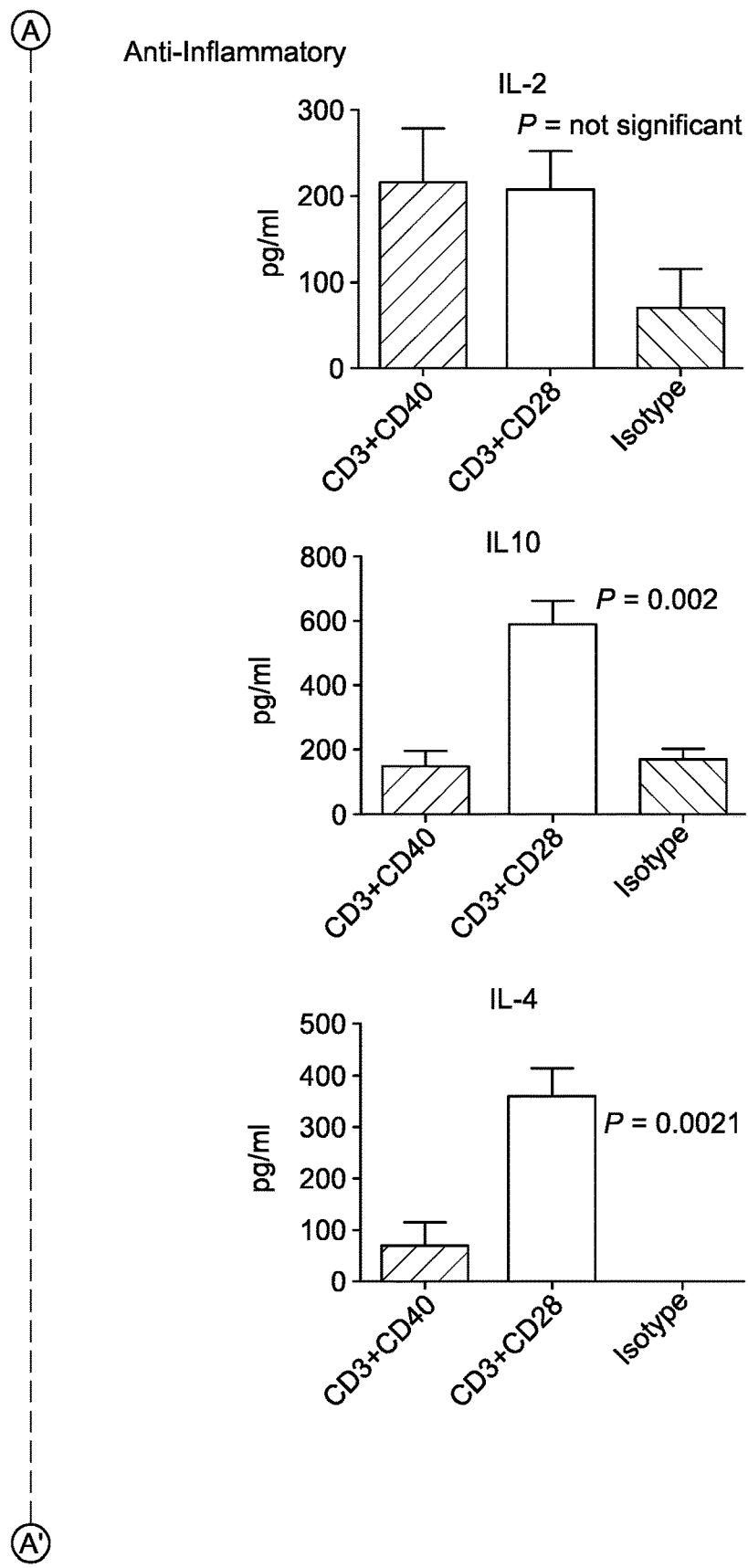

FIG. 7 shows the cytokine production in Th40 cells. Purified Th40 cells from spleens of 9- to 12-week-old female NOD mice were treated with antiCD3+anti-CD28 (classical T-cell co-stimulus), anti-CD3+ anti-CD40, or isotype controls. Cytokine production was measured after 24 hr. One-way analysis of variance was performed and significant differences are indicated.

Example 8

Figure 8:
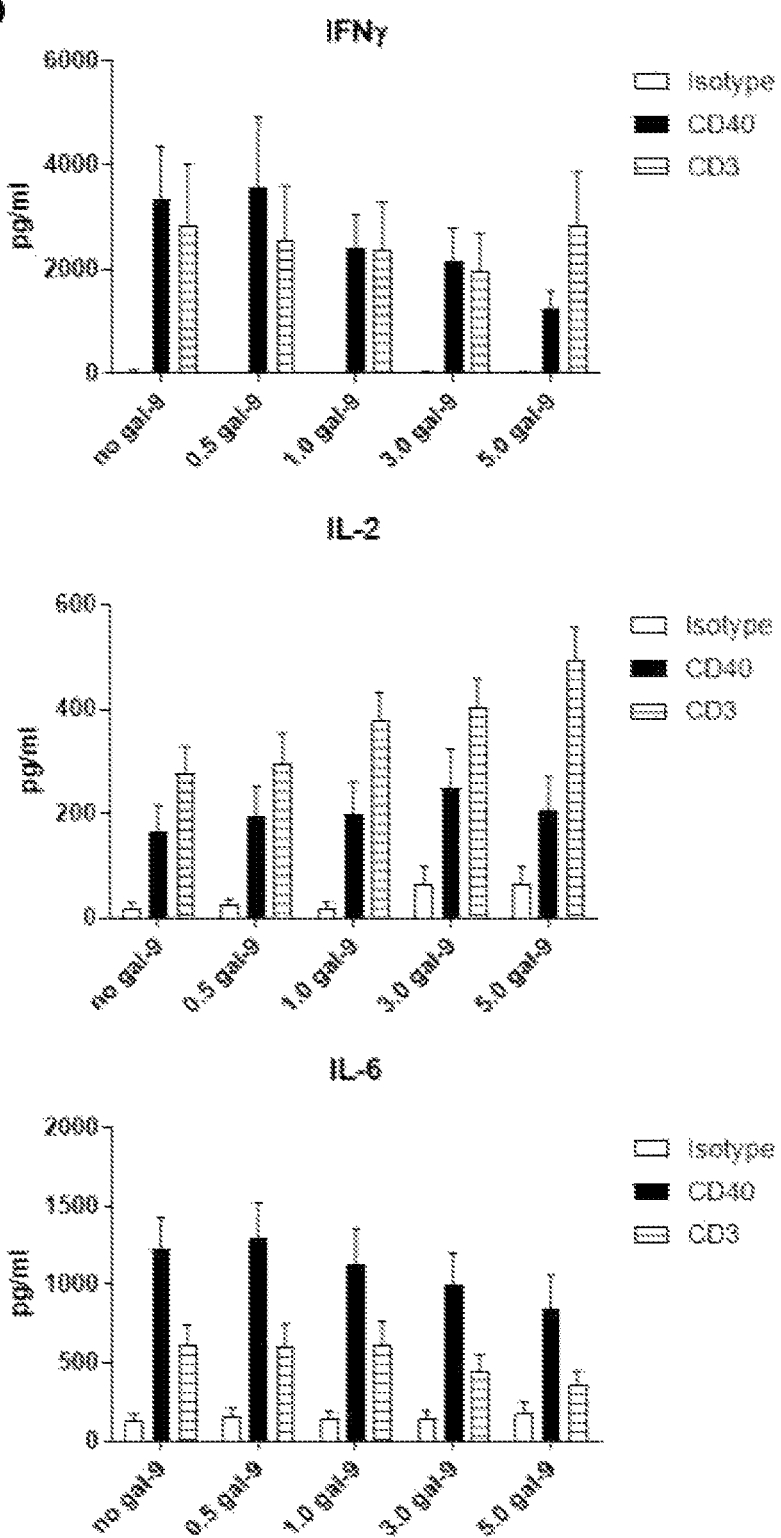
FIG. 8 provides several graphs of CD40 and CD3 induced cytokine phenotypes differ and galectin-9 alters the production levels.

FIG. 8 shows CD40 and CD3 induced cytokine phenotypes differ and galectin-9 alters the production level. CD4loCD40+ T cells (Th40 cells) were sorted from 7-20 weeks old female NOD spleens. Cells were either isotype treated, CD40- or CD3-stimulated in the absence/presence of indicated concentrations of galectin-9 (gal-9; mg/ml) for 3 days then cytokines were measured. Bar graphs depict means with SEM. Asterisks denote significant differences determined by one-way Anova; *-P between 0.01 and 0.05; -P, 0.01; *-P, 0.001. Measurements were done on four individual mice of different ages.

Example 9

Figure 9A:
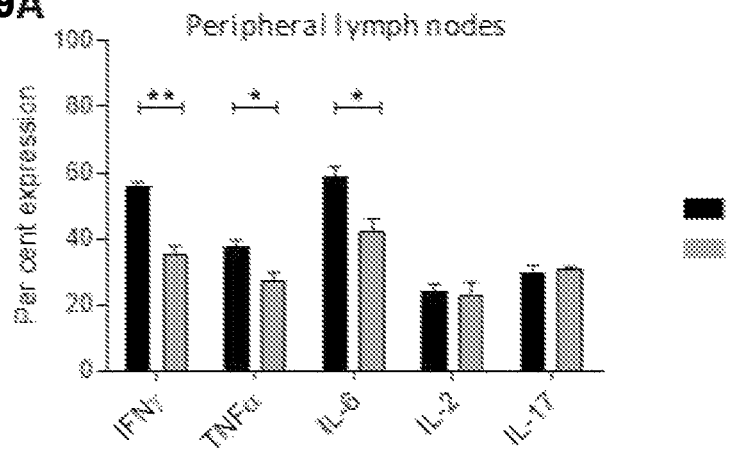
FIGS. 9A-9C provide graphs of KGYY-15 and its effects on production of inflammatory cytokines of Th40 cells.
Figure 9B:
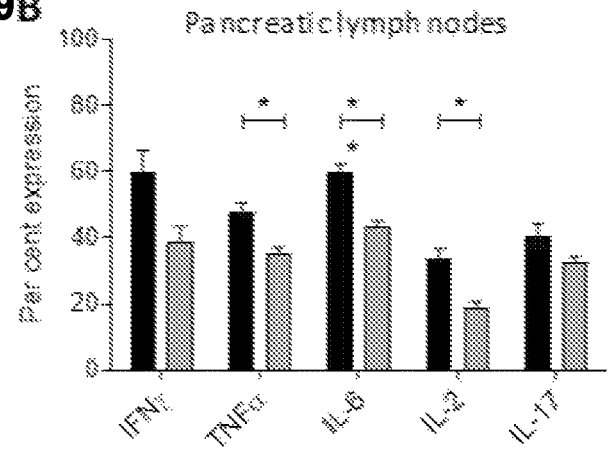
Figure 9C:
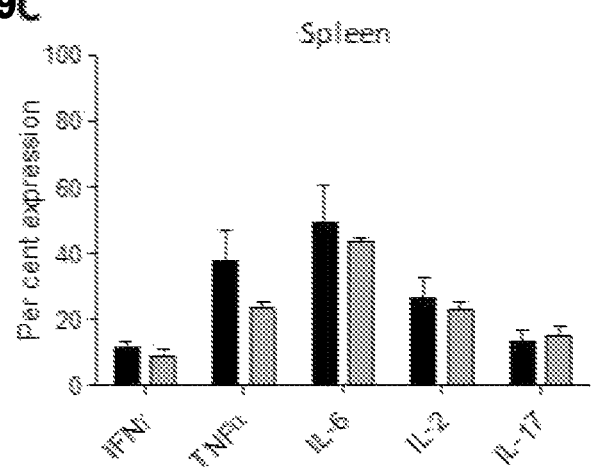

FIG. 9, includes sub-parts 9A, 9B, and 9C, and shows KGYY15 controls the production of inflammatory cytokines by Th40 cells. Immediately ex-vivo lymphocytes from NOD mice treated with KGYY15 (grey) and control mice (black) were stained for cytokines. Data for lymphocytes from (A) peripheral lymph node; (B) pancreatic lymph node; and (C) spleen. Bars show cytokine-positive cells within gated CD4+CD40+ cell populations (Th40), represented as a percentage. Data are from three individual mice from each group and are represented as the mean±SEM. *p<0.05, **p<0.01 by two-tailed unpaired t test.

Example 10

Figure 10:
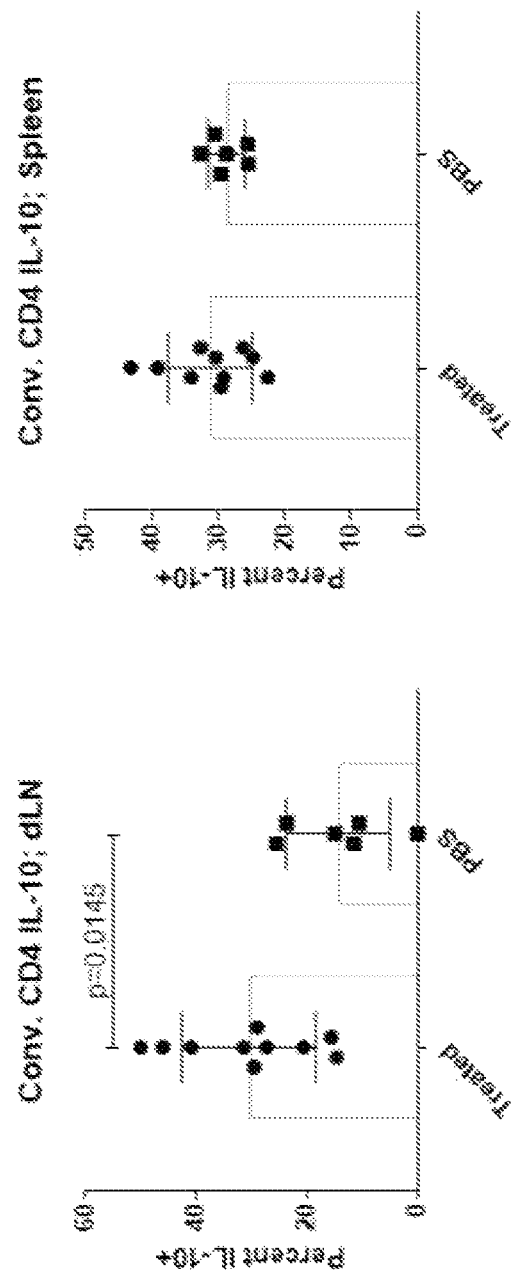
FIG. 10 provides two graphs which show how KGYY-6 treatment alters IL-10 production by conventional CD4 T cells.

FIG. 10 shows that KGYY6 treatment alters IL-10 production by conventional CD4 T cells. Intracellular cytokine expression profiles were examined in conventional CD4 T cells immediately ex-vivo at the end of the EAE experiment, after 33 days. In conventional CD4 T cells from draining lymph nodes (dLN), but not spleen, of KGYY6 treated animals there was an increase in intracellular IL-10 compared to the same cells from untreated animals (p=0.0145; t-test).

Example 11

Figure 11:
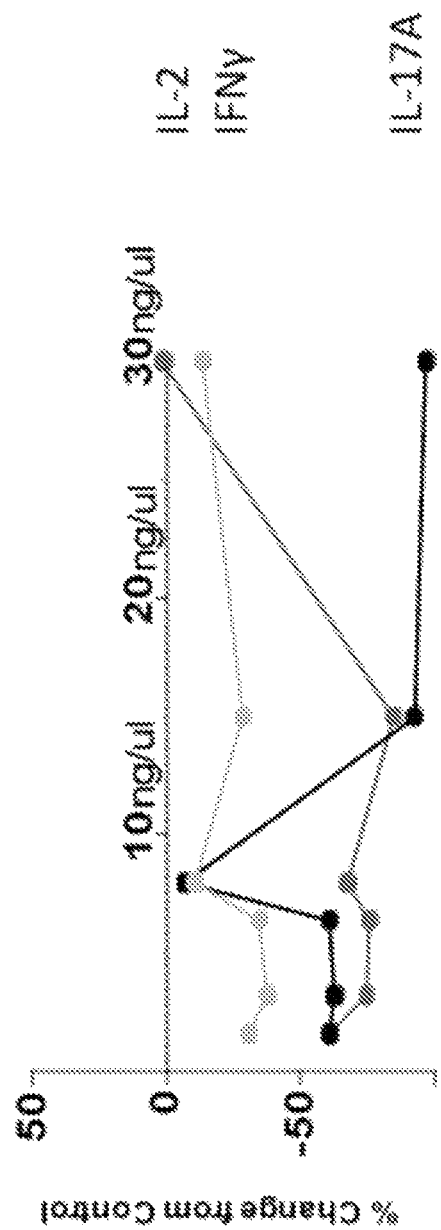
FIG. 11 provides a graph that shows the effect of KGYY-6 on inflammatory cytokines.

FIG. 11 shows KGYY6 decreases production of inflammatory cytokines. CD3+CD4+CD40+(Th40) splenic cells were purified from ApoE−/− with cardiovascular disease. The cells were cultured overnight in the absence/presence of varying concentrations of KGYY6 peptide. Treated cells demonstrated varying degrees of reduction in the inflammatory cytokines IL-2, IFNγ and IL-17A compared to the untreated cells.

Example 12

Figure 12A:
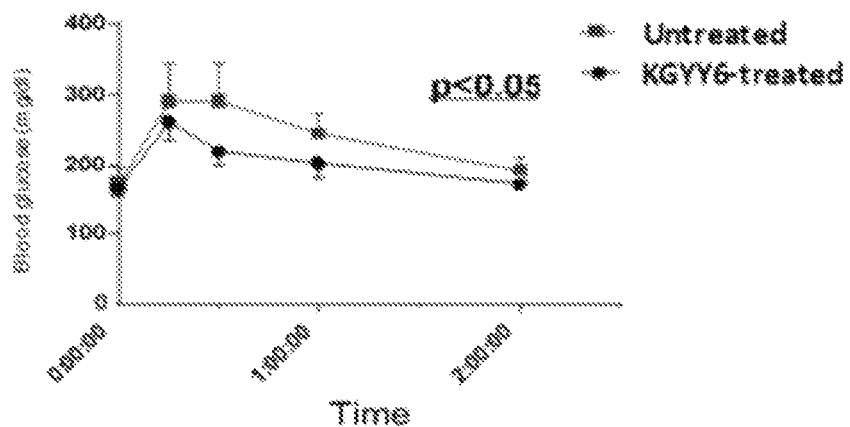
FIGS. 12A and 12B provide graphs demonstrating how KGYY6 may improve glucose tolerance and insulin sensitivity.
Figure 12B:
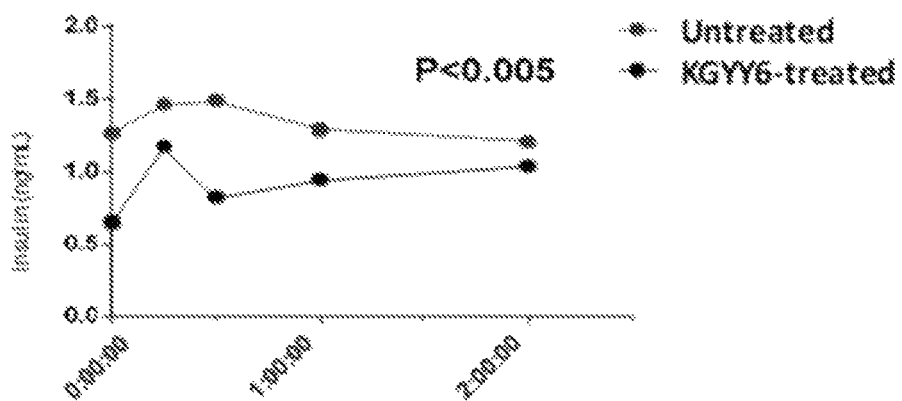

FIG. 12 which includes sub-parts FIGS. 12A and 12B demonstrates that KGYY6 improves glucose tolerance and insulin sensitivity. Graphs represent a statistically significant improvement in glucose tolerance (A; p<0.05) and insulin sensitivity (B; p<0.005). ApoE −/−mice example 13

Figure 13:
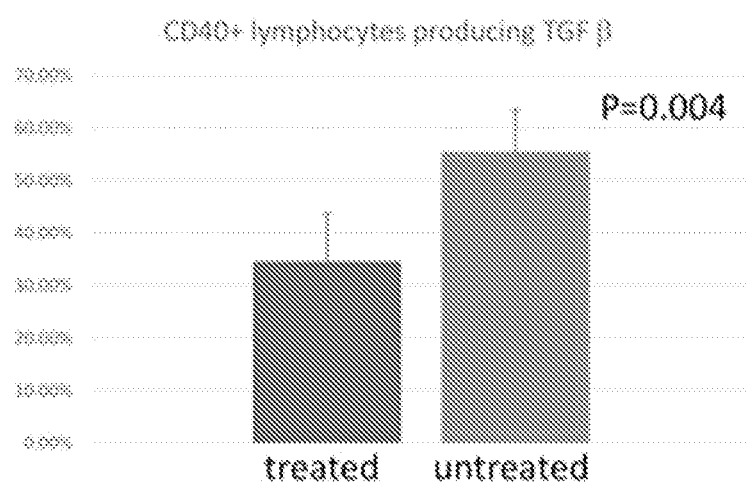
FIG. 13 provides a chart that shows that mice treated with KGYY-6 decrease production of TGF.

FIG. 13 shows ApoE−/−mice treated with KGYY6 decrease production of TGF. Th40 cells were purified from ApoE−/−mice with cardiovascular disease as well as from ApoE−/−mice that were treated with KGYY6. Immediately ex-vivo, the cells were stained for CD3, CD4, and CD40 and intracellular TGF and analyzed by flow cytometry. Cells were gated on CD3 then CD4 and CD40 for Th40 cells then levels of TGF were assessed.

Example 14

Figure 14A:
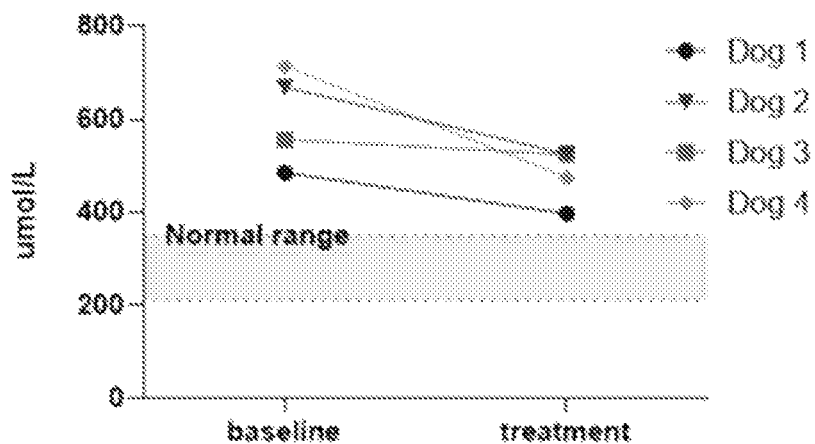
Figure 14B:
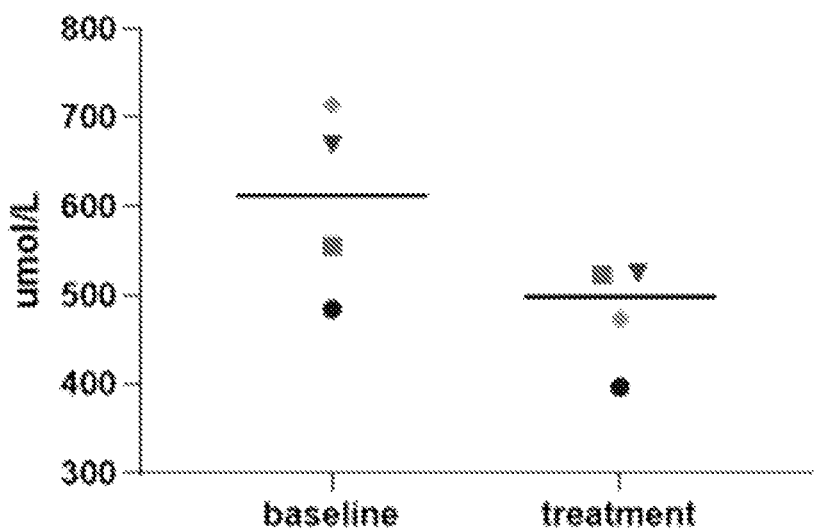

FIG. 14, which includes sub-parts FIGS. 14A, 14B, and 14C demonstrates that Dog 15-mer peptide treatment significantly decreases fructoseamine levels in TID dogs. Four longstanding TID domestic dogs were treated with i.v. infusions of dog 15-mer peptide, twice in the first week then weekly thereafter. Levels of fructoseamine were measured before the first infusion and several weeks after initiation of treatment.

Example 15

Figure 15A:
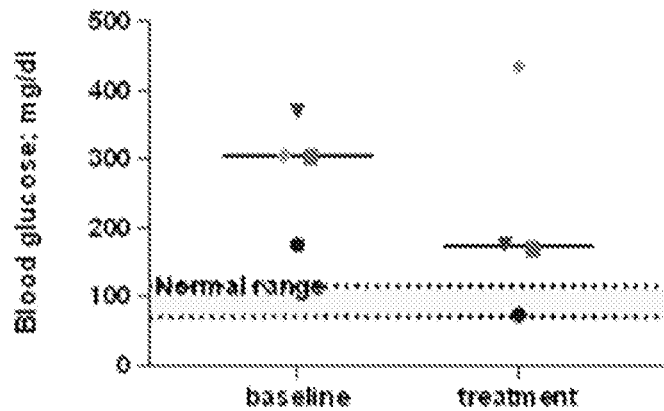
FIGS. 15A-15B provides charts showing that 15-mer peptide decreases blood glucose levels in TID dogs.
Figure 15B:
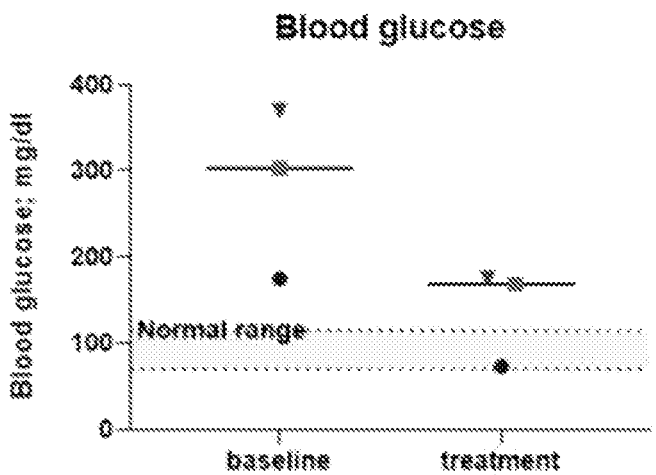

FIG. 15, which includes sub-parts FIGS. 15A and 15B demonstrates that 15-mer peptide used to treat diabetic dogs was able to positively impact and help control blood glucose levels. Dog 15-mer peptide treatment decreases average blood glucose levels in T1D dogs. Four longstanding T1D domestic dogs were treated with i.v. infusions of dog 15-mer peptide, twice in the first week then weekly thereafter. Levels of blood glucose were measured before the first infusion and several weeks after initiation of treatment. All but one of the 4 dogs achieved better blood glucose control.

Example 16

Figure 16:
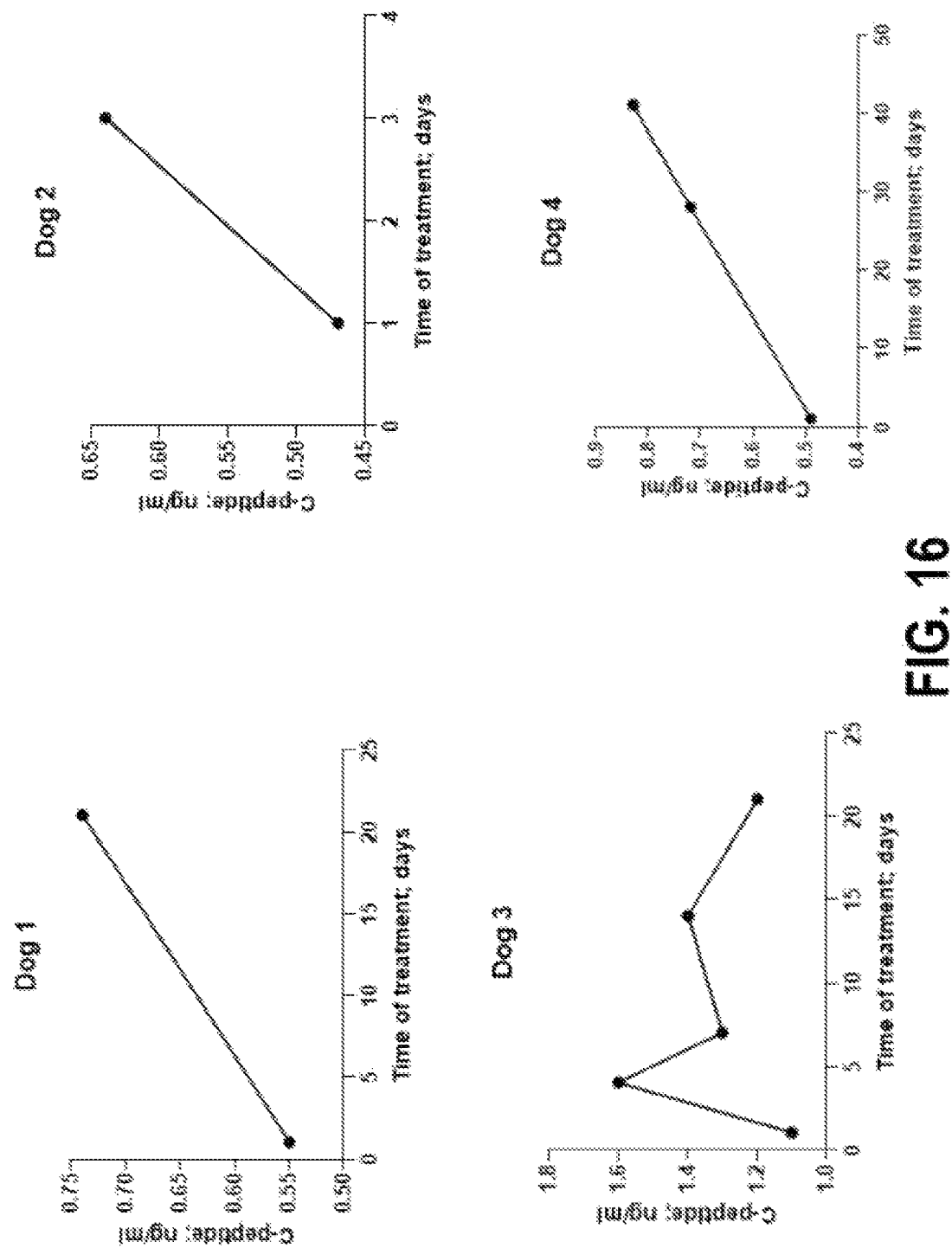
FIG. 16 provides several graphs demonstrating the 15-mer peptide may increase c-peptide in T1D dogs.

FIG. 16 provides graphs of four dogs treated with 15-mer peptide and demonstrates that Dog 15-mer peptide treatment increases c-peptide in T1D dogs. Four longstanding T1D domestic dogs were treated with i.v. infusions of dog 15-mer peptide, twice in the first week then weekly thereafter. Levels of c-peptide were measured before the first infusion and several weeks after initiation of treatment.

Example 17

Figure 17:
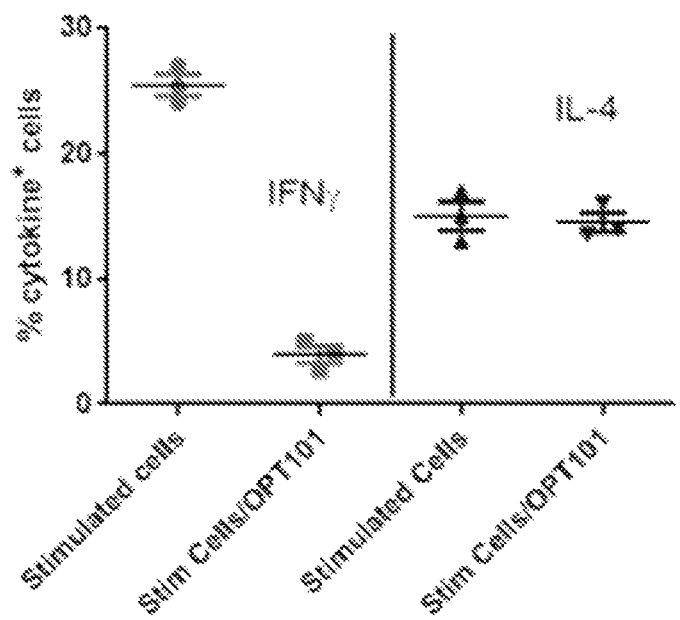
FIG. 17 provides a graph showing that KGYY-15 may affect the inflammatory cytokine IFNγ.

FIG. 17 provides a graph of that demonstrates that KGYY15 regulates the inflammatory cytokine IFNγ without impacting production of non-inflammatory IL-4. Human T cells, isolated from peripheral blood of T1D subjects, were stimulated with autologous antigen presenting cells loaded with human islets in the absence/presence of KGYY15 then intracellular IFNγ and IL-4 was measured by flow cytometry. $P<0.0001$ for IFNγ.

The various features, processes, and implementations described above may be used independently of one another, or may be combined in various ways. All possible combinations and sub-combinations are intended to fall within the scope of this disclosure. In addition, certain method or process blocks may be omitted in some implementations. While certain example implementations have been described, these implementations have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and compositions described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms and modifications as would fall within the scope and spirit of certain of the inventions disclosed herein.

REFERENCES

Bai B, Hu Q, Hu H, Zhou P, Shi Z, Meng J, Lu B, Huang Y, Mao P, Wang H. Virus-like particles of SARS-like coronavirus formed by membrane proteins from different origins demonstrate stimulating activity in human dendritic cells. PLoS One. 2008 Jul. 16; 3(7): e2685. doi: 10.1371/journal.pone.0002685.

Chou F C, Shieh S J, Sytwu H K. Attenuation of Th 1 response through galectin-9 and T-cell Ig mucin 3 interaction inhibits autoimmune diabetes in NOD mice. Eur J Immunol. 2009, 39: 2403-2411.

de Pablo R, Monserrat J, Reyes E, Diaz D, Rodriguez-Zapata M, de la Hera A, Prieto A, Alvarez-Mon M. Sepsis-induced acute respiratory distress syndrome with fatal outcome is associated to increased serum transforming growth factor beta-1 levels. Eur. J. Internal Med., June 2012, Volume 23, Issue 4, Pages 358-362.

Deng G, Carter J, Traystman R J, Wagner D H, Herson P S. Pro-inflammatory T-lymphocytes rapidly infiltrate into the brain and contribute to neuronal injury following cardiac arrest and cardiopulmonary resuscitation. J Neuroimmunol. 2014 Sep. 15; 274(1-2): 132-40. doi: 10.1016/j.jneuroim.2014.07.009. Epub 2014 Jul. 22.

Faulkner L, Cooper A, Fantino C, Altmann D M, Sriskandan S. The Mechanism of Superantigen-Mediated Toxic Shock: Not a Simple Th 1 Cytokine Storm. The Journal of Immunology, 2005, 175: 6870-6877.

Fatkhullina A R, Peshkova I O, Koltsova E K. The Role of Cytokines in the Development of Atherosclerosis. Biochemistry (Mosc). 2016 November; 81(11): 1358-1370. doi: 10.1134/S0006297916110134

Lee D W, Gardner R, Porter D L, Louis C U, Ahmed N, Jensen M, Grupp S A, Mackall C L (July 2014). Current concepts in the diagnosis and management of cytokine release syndrome. Blood. 124 (2): 188-95. doi: 10.1182/blood-2014-05-552729

Ma D Y, Clark E A The role of CD40 and CD40L in Dendritic Cells. Semin Immunol. 2009 October; 21 (5): 265-272.

Medscape—Apr. 4, 2020. Huge Global Push for RCTs in COVID-19: From Random to Randomized.

Mehta P, McAuley D F, Brown M, et al. (16 Mar. 2020). COVID-19: consider cytokine storm syndromes and immunosuppression. The Lancet. 395: 1033-34. doi: 10.1016/50140-6736 (20)30628-0.

Poe J C, Wagner D H, Miller R W, Stout R D, Suttles J. IL-4 and IL-10 modulation of CD40-mediated signaling of monocyte IL-I beta synthesis and rescue from apoptosis. J. Immunol 1997; 159:846-852; www.jimmunol.org/content/159/2/846.

Ruan Q, Yang K, Wang W, Jiang L, Song J (March 2020). Clinical predictors of mortality due to COVID-19 based on an analysis of data of 150 patients from Wuhan, China. Intensive Care Medicine. doi: 10.1007/s00134-020-05991-x.

Vaitaitis G M, Poulin M, Sanderson R J, Haskins K, Wagner D H. Cutting edge: CD40– induced expression of recombination activating gene (RAG) 1 and RAG2: a mechanism for the generation of autoaggressive T cells in the periphery. J Immunol. 2003 Apr. 1; 170 (7): 3455-9.

Vaitaitis G M, Wagner D H. High distribution of CD40 and TRAF2 in Th40 T cell rafts leads to preferential survival of this auto-aggressive population in autoimmunity. PLoS One. 2008 Apr. 30; 3 (4):e2076. doi: 10.1371/journal.pone.0002076.

Vaitaitis G, Waid D, Wagner D H. The Expanding Role of TNF-Receptor Super Family Member CD40 (tnfrsf5) in Autoimmune Disease: Focus on Th40 Cells. Current Immunology Reviews, 2010, 6, 130-136.

Vaitaitis G M and Wagner D H. Galectin-9 Controls C D40 Signaling through a Tim-3 Independent Mechanism and Redirects the Cytokine Profile of Pathogenic T Cells in Autoimmunity. PLoS ONE, 2012, 7(6): e38708. doi: 10.1371/journal.pone.0038708

Vaitaitis G M, Olmstead M H, Waid D M, Carter J R, Wagner D H. A CD40-targeted peptide controls and reverses type 1 diabetes in NOD mice. Diabetologia. 2014 November; 57(11): 2366-2373. doi: 10.1007/s00125-014-3342-5.

Vaitaitis G M, Waid D M, Yussman M G, Wagner D H. CD40-mediated signaling influences trafficking, T-cell receptor expression, and T-cell pathogenesis, in the NOD model of type 1 Diabetes. Immunology, 2017, 152, 243-254. doi: 10.1111/imm.12761.

Vaitaitis G M, Yussman M G, Waid D M, Wagner D H. Th40 cells (CD4+CD40+ T cells) drive a more severe form of Experimental Autoimmune Encephalomyelitis than conventional CD4 T cells. PLoS One. 2017 Feb. 13; 12 (2):e0172037. doi: 10.1371/journal.pone.0172037. eCollection 2017.

Vaitaitis G M, Yussman M G, Wagner D H. A CD40 targeting peptide prevents severe symptoms in experimental autoimmune encephalomyelitis. Journal of Neuroimmunology, Volume 332, 15 Jul. 2019, Pages 8-15.

Wagner D H, Hagman J, Linsley P S, Hodsdon W, Freed J H, Newell M K. Rescue of thymocytes from glucocorticoid-induced cell death mediated by CD28/CTLA-4 costimulatory interactions with B7-1/B7-2. J Exp Med. 1996 Nov. 1; 184(5): 1631-8.

Wagner D H, Vaitaitis G, Sanderson R, Poulin M, Dobbs C, Haskins K. Expression of CD40 identifies a unique pathogenic T cell population in type 1 diabetes. Proc Natl Acad Sci U S A 2002 Mar. 19; 99(6):3782-7. Epub 2002 Mar. 12.

Waid D M, Vaitaitis G M, Wagner D H. Peripheral C D4loCD40+ auto-aggressive T cell expansion during insulin-dependent diabetes mellitus. Eur J Immunol. 2004 May; 34(5): 1488-97.

Waid D M, Wagner R J, Putnam A, Vaitaitis G M, Pennock N D, Calverley D C, Gottlieb P, Wagner D H. A unique T cell subset described as CD4loCD40+ T cells (TCD40) in human type 1 diabetes. Clin Immunol. 2007 August; 124(2): 138-48. Epub 2007 Jun. 8.

Waid D M, Vaitaitis G M, Pennock N D, Wagner D H. Disruption of the homeostatic balance between auto-aggressive (CD4+CD40+) and regulatory (CD4+CD25+FoxP3+) T cells promotes diabetes. J Leukoc Biol. 2008 August; 84(2):43 1-9. doi: 10.1 189/jlb.1207857. Epub 2008 May 9.

Waid D M, Schreiner T, Vaitaitis G, Carter J R, Corboy J R, Wagner D H Jr. Defining a new biomarker for the autoimmune component of Multiple Sclerosis: Th40 cells. J Neuroimmunol. 2014 May 15; 270 (1-2): 75-85. doi: 10.1016/j.jneuroim.2014.03.009. Epub 2014 Mar. 15.

Yussman M, Wagner D, Vaitaitis G, Waid D. Abstract 189: Novel Drug Development Controlling Residual Inflammatory Risk in Diabetic Atherosclerotic Disease. Originally published 12 Mar. 2019https://doi.org/10.1161/atvb.38.suppl 1.189 Arteriosclerosis, Thrombosis, and Vascular Biology. 2018; 38:A1 89

Zhang C, Wu Z, Li J-W, Zhao H, Wang G-Q. The cytokine release syndrome (CRS) of severe COVID-19 and Interleukin6 receptor (IL-6R) antagonist Tocilizumab may be the key to reduce the mortality. International Journal of Antimicrobial Agents (2020). doi:https://doi.org/10.1016/j.ijantimicag.2020.105954

Vox. 12 Mar. 2020. Retrieved 14 Mar.2020. How doctors can potentially significantly reduce the number of deaths from Covid-19.

www.scientificamerican.com/article/heres-what-we-know-about-the-most-touted-drugs-tested-for-covid-191/, last accessed Apr. 16, 2020.

www.nhlbi.nih.gov/health-topics/acute-respiratory-distress-syndrome, last accessed Apr. 17, 2020.

Protocol Title: Treatment of Cytokine Release Syndrome in COVID-19 Patients

This study will be conducted in compliance with the clinical study protocol (and amendments), the World Medical Association Declaration of Helsinki, International Council for Harmonisation of Technical Requirements for Pharmaceuticals for Human Use (ICH) Guideline for Good Clinical Practice E6 (R2), applicable US Food and Drug Administration (FDA) regulatory requirements, and local regulations governing the conduct of clinical studies.

The protocol, informed consent form(s), recruitment materials, and all patient materials will be submitted to the Institutional Review Board (IRB) for review and approval. Approval of both the protocol and the consent form must be obtained before any patient is enrolled. Any amendment to the protocol will require review and approval by the IRB before the changes are implemented to the study. In addition, all changes to the consent form will be RB-approved; a determination will be made regarding whether a new consent needs to be obtained from patients who provided consent, using a previously approved consent form.

Abbreviations

| Abbreviation | Definition |
|---|---|
| ADA | anti-drug antibody |
| AE | adverse event |
| aPTT | activated partial thromboplastin time |
| AST | aspartate transaminase (SGOT) |
| AUCo-t | area under the curve from zero up to time t |
| ATC | Anatomical Therapeutic Chemical |
| BUN | blood urea nitrogen |
| CD | cluster of differentiation |
| CDC | Centers for Disease Control and Prevention |
| CFR | Code of Federal Regulations |
| CHO | Chinese hamster ovary |
| Cmax | maximum observed serum drug concentration |
| CNS | central nervous system |
| CONSORT | Consolidated Standards of Reporting Trials |
| COVID-19 | Coronavirus disease of 2019 |
| CTCAE | Common Terminology Criteria for Adverse Events |
| CRO | contract research organization |
| CRP | C-reactive protein |
| DLT | dose-limiting toxicity |
| DRF | dose range finding |
| ECG | Electrocardiogram |
| ECL | electro-chemi-luminescent |
| eCRF | electronic case report form |
| EDC | electronic data capture |
| EDTA | ethylene diamine tetra-acetic acid |
| FDA | Food and Drug Administration |
| FOB | functional observational battery |
| GCP | Good Clinical Practice |
| GGT | gamma glutamyltransferase |
| GLP | good laboratory practice |
| GM-CSF | granulocyte-macrophage colony-stimulating factor |
| HIPAA | Health Insurance Portability and Accountability Act |
| HIV | human immunodeficiency virus |
| IB | Investigator's Brochure |
| ICF | informed consent form |
| ICH | The International Council for Harmonization of Technical Requirements for Pharmaceuticals for Human Use |
| ICR | Institute of Cancer Research |
| ID | Identification |
| IEC | independent ethics committee |
| IFN | Interferon |

Abbreviations

| Abbreviation | Definition |
|---|---|
| IgG | Immunoglobulin G |
| IL | Interleukin |
| INR | International Normalized Ratio |
| IP | investigational product |
| IRB | institutional review board |
| IV | Intravenous |
| KGYY15 | another designation for OPT101 |
| LDH | lactate dehydrogenase |
| mAb | monoclonal antibody |
| MCP-1 | monocyte chemoattractant protein- I |
| MedDRA | Medical Dictionary for Regulatory Activities |
| MRI | magnetic resonance imaging |
| MSD | Meso Scale Discovery ® |
| msec | Millisecond |
| MTD | maximum tolerated dose |
| n | number of subjects with an observation |
| N | number of subjects in the dataset or population |
| NCI | National Cancer Institute |
| NOAEL | no-observed-adverse-effect level |
| NOD | non-obese diabetic |
| PDF | Portable Document Format |
| PK | Pharmacokinetic |
| PT | preferred term |
| QTcF | Corrected QT interval using Fridericia |
| RBC | red blood cell |
| TNF-a | tumor necrosis factor-a |
| SAD | single ascending dose |
| SAE | serious adverse event |
| SAP | statistical analysis plan |
| SC | Subcutaneous |
| SD | standard deviation |
| soc | system organ class |
| SOP | standard operating procedure |
| TCR | tissue cross-reactivity |
| TEAE | treatment-emergent adverse event |
| TK | Toxicokinetics |
| TNF | tumor necrosis factor |
| us | United States |
| WBC | white blood cell |
| WOCBP | women of childbearing potential |

Protocol Summary PROTOCOL SYNOPSIS

| | |
|---|---|
| Protocol Title: | Treatment of Cytokine Release Syndrome in COVID-19 Patients |
| Study Number: | OPT-100-30 |
| Development Phase: | Phase 1 |
| Sponsor: | Op-T LLC, Inc. |
| Study Center(s): | This study will be conducted in a minimum of 2 and a maximum of 4 centers in the US. |
| Primary Objective or Aim: | The primary objective of the study is to assess the safety of OPT101 in the treatment of COVID-19 infected patients who are critically ill with cytokine release syndrome. |
| Secondary Objective(s): | Changes to one or more blood cytokine levels, specifically IL-1β, IL-6, TNF α, IFN-γ, IL-2, IL-17A,, IL-12, IL-4, IL-10, IL-2rec, IL-5, IL-8 (research) <br> Changes to any combination of the following: CD3+, CD4+, CD45RA+, CD45RO+, CD8+ and CD 19+ lymphocytes, and NK cells (research) <br> Changes to ferritin, high-sensitivity C-reactive protein (hs CRP), LDH <br> No abnormal increase in the clotting cascade. <br> Evaluate the clinical outcomes including. <br> survival, <br> No increase in oxygen requirement and no increase in respiratory support measures <br> Supplemental oxygen requirement to maintain oxygen saturation >90% stable or decreased without escalation of respiratory measures (addition of CPAP, initiation of mechanical ventilation) <br> Improvement of end organ pathology (cardiac, liver, kidney, brain) <br> Improvement of blood pressure <br> Improvement in time of discharge from ICU |
| Investigational Product: | The investigational product, OPT101, is a 15-mer peptide derived from the sequence of mouse CD154, which is 87% identical to human sequences and contains the highly conserved KGYY amino acid sequence (lysine glycine tyrosine tyrosine) that is involved in binding to CD40 (Vaitaitis et al 2014). Severe COVID-19 patients have been shown to have increased blood cytokines (hypercytokinemia) which contributes significantly to the progress of the disease. OPT101 has been shown to interfere with the CD40/CD154 lymphocyte interaction. CD40 deficient mice, with no CD40/CD154 interaction, have been shown to be protected from hypercytokinemia after an endotoxin challenge. In normal mice challenged with endotoxin, OPT101 IV pre-treatment at 5 to 20 mg/kg resulted in significant decrease in the hypercytokinemia response. Human peripheral blood lymphocytes challenged in vitro with tetanus toxoid results in cytokine release and in vitro treatment with OPT101 resulted in a decrease of this cytokine release. These data suggest that targeting the CD40 receptor with OPT101 and inhibiting the CD40/CD154 interaction could prove therapeutic in COVID-19 induced hypercytokinemia <br> Potential safety issue with OPT101 have been evaluated in rat and dog IV repeat-dose 8-week GLP studies. When OPT101 was given by slow IV infusion over 30 minutes, once weekly for 8 weeks, no toxicity was seen after dosing to the highest dose of 200 mg/kg in rats and 400 mg/kg in dogs with the exception of a transient infusion reaction mediated at least in part by histamine; this reaction was associated with transient hematology and clinical chemistry changes. The infusion reaction no observable adverse effect levels (NOAEL) were 200 and 10 mg/kg for rats and dogs respectively. |

| | |
|---|---|
| Intervention | This is a first-in-human study, phase 1, non-randomized, open label study. The study incorporates a fast-track approach for dose escalation. Up to 8 total daily IV treatments with 4 escalating doses (0.5, 1.0, 2.0 and 4.0 mg/kg; two daily doses at each dose level) will be administered to a total of 3 patients in the first cohort. If no dose limiting toxicity (DLT) is observed during dose escalation, 3 additional subjects will be enrolled in a second cohort and receive up to 8 total IV treatments with 2.0 mg/kg OPT101 followed by 3 additional subjects enrolled in a third cohort and receive up to 8 total IV treatments with 4.0 mg/kg OPT101.<br>Safety data from the lower dose cohort<br>Safety data from the lower dose cohort<br>(2) will be reviewed by the Safety Review Committee (SRC) before subjects are enrolled in the higher dose cohort (3). Additional subjects may be added to any cohort if dose limiting toxicity (DLT) is observed for a maximum of up to 6 subjects per cohort. An additional 6 subjects may also be enrolled in an intermediate dose cohort between the dose level which exceeds the defined maximum tolerated dose (MTD) and the previous defined dose level. Safety and tolerability will be assessed at each dose, and escalation to the next highest dose will occur only if no DLT is observed.<br>The starting dose of 0.5 mg/kg was calculated from 1/10 the 10 mg/kg NOAEL in the dog toxicity study, converted to the human dose on a mg/m2 basis. OPT101 will be administered by a slow IV infusion over 30 minutes. For all cohorts 3 subjects will be enrolled to the assigned dose level of OPT101. If 0/3 subject experiences DLT, dose escalation will continue to the next dose level. If 1/3 subject experiences DLT, an additional 3 subjects will be enrolled at the same dose level. A maximum of 6 subjects may be enrolled in each dose cohort. For all cohorts, if <1/6 subject experiences DLT, dose escalation will continue to the next dose level. Dose escalation will be stopped if >2/6 subjects experience DLT and the dose will be de-escalated to the previous dose level, unless it is at the lowest dose. A new cohort of 6 subjects may be enrolled to receive an intermediate dose between the previous dose level and the dose level that exceeded the MTD. MTD is defined as a dose at which less than 33% of subjects have a DLT during the first 2 days of the treatment, regardless if the IP is considered responsible. All subjects will be in the ICU and will receive 24-hour monitoring.<br>Patients will be followed for safety, immunological (blood cytokine levels and blood lymphocyte subset numbers), and clinical assessments for 3 days after the last treatment. An additional immunological assessment will be performed the day prior to discharge along with vital signs. Impossible, follow up via phone call or text message with all patients will occur at 30 days post last day of treatment if discharge has already occurred. Patients experiencing immunological and/or clinical effects may be followed for longer, until the immunological or clinical variables return to baseline levels. |
| Dose Escalation Stopping Criteria | Data for all subjects will be reviewed by the Safety Review Committee (SRC) before dose escalation or de-escalation, or at any time point as needed when safety concerns arise. In addition to the SRC oversight and recommendations, the following stopping criteria will be implemented:<br>Subject stopping criteria: If a subject experiences an AE that is deemed by the clinical site Principal Investigator to be at least "possibly" drug-related and is Grade 2::3 in severity (using the Common Terminology Criteria for Adverse Events (CTCAE v 5), that subject will be withdrawn from dosing, return for all scheduled evaluation visits, and be followed until the AE resolves or stabilizes.<br>Cohort stopping criteria: If 33% (2 of the first 6 patients), at any time experience any of the following events not clearly due to the underlying disease or extraneous causes and is deemed by the clinical center Principal Investigator to be at least "possibly" drug-related and Grade 2::3 in severity by CTCAE. Dosing in that cohort, as well as further dose escalation, will be suspended within that study arm. Events such as:<br>An SAE occurs that is not clearly unrelated to IP<br>Any Grade 2:: 3 (this may exclude Grade 3 nausea/vomiting or diarrhea for <72 hours with adequate supportive care, Grade 3 fatigue for >1 week, Grade 2:: 3 uncomplicated electrolyte abnormality that resolves spontaneously or in response to conventional medical intervention, and Grade 2:: 3 abnormalities in laboratories within a few standard deviations)<br>Increases in Von Willebrand Factor from baseline<br>Increases in Factor VIII from baseline<br>Hy's law cases |
| Treatment | The investigational product, OPT 101, will be provided as a sterile solution in 10 mM acetate buffer, in 5% glucose, in water, pH 5.5, 5 mL at 20 mg/mL, 100 mg/vial. On the same day as the investigational product administration, the product will be diluted in saline to a total volume of 5O mL, at the concentration of OPT101 required for each dose level, and administered by intravenous (IV) infusion over 30 minutes. |

| | |
|---|---|
| Study Population: | The study population will be in patients 18 years and older, with COVID-19 infection who are critically ill with cytokine release syndrome. Up to 12 patients with COVID-19 infection confirmed by PCR will be enrolled in up to 2 investigational sites. Treatment will be based on the following criteria:<br>1. The patient has a life-threatening condition that needs immediate treatment.<br>2. No generally acceptable alternative treatment for the condition exists; and<br>3. Patients with the virus infection as documented by prior exposure to a virus and a positive blood PCR test for virus are eligible. |
| Entry Criteria | Inclusion:<br>Laboratory confirmation of COVID-19 infection by PCR.<br>Demonstration of cytokine release syndrome. Signs of cytokine release syndrome defined as ANY of the following:<br>serum ferritin concentration >1000 mcg/L and rising since last 24 h<br>single ferritin above 2000 mcg/L in patients requiring immediate high flow oxygen device or mechanical ventilation<br>lymphopenia defined as <800 lymphocytes/microliter) and two of the following extra criteria<br>Ferritin >700 mcg/L and rising since last 24 h<br>increased LDH (above 300 IU/L) and rising last 24 h<br>D-Dimers >1000 ng/mL and rising since last 24 h<br>CRP above 70 mg/L and rising since last 24 h and absence of bacterial infection<br>if three of the above are present at admission, no need to document 24 h rise<br>COVID-19 with the following disease characteristics:<br>Early acute lung injury (ALl)/early acute respiratory distress syndrome (ARDS).<br>Severe disease, defined as:<br>dyspnea,<br>respiratory frequency ≥30/min,<br>blood oxygen saturation ≤93%,<br>partial pressure of arterial oxygen to fraction of inspired oxygen ratio of <300, and/or<br>lung infiltrates >50%.<br>Life-threatening disease, defined as:<br>respiratory failure,<br>septic shock, and/or<br>multiple organ dysfunction or failure.<br>Admission to the ICU.<br>Stable blood pressure not requiring vasopressors initially.<br>Informed consent from the patient or legal representative using the associated Patient Informed Consent form must be completed.<br>Male or female aged ≥18 years on the day of signing informed consent<br>Exclusion:<br>Patients with a history of venous and arterial thromboembolic events including, but not limited to, the following: deep venous thrombosis, pulmonary embolism, myocardial infarction, stroke, transient ischemic attack or arterial insufficiency causing digital gangrene should be excluded. In addition, patients with an already known increase in Von Willebrand Factor or Factor IV as can be seen in COVID-19 infections.<br>1Patients with a prior history of abnormal prothrombotic laboratories such as congenital or inherited deficiency of antithrombin III, protein C, protein S, or confinmed diagnosis of antiphospholipid syndrome should also be excluded<br>Patients who are intubated prior to starting peptide therapy (peptide therapy may be continued if patient is intubated after enrollment)<br>Biopsy proven cancer not in remission<br>Known pre-existing non-COVID-19 related hypercoagulability or other coagulopathy.<br>Severe hemodynamic instability<br>History of hypersensitivity to antihistamines<br>Participation in another competing investigational drug, investigational product or vaccine trial<br>Is pregnant<br>Advance directive indicating no desire for heroic measures |

-continued

| | |
|---|---|
| Study Procedures: | Study procedures, frequency, and timing are provided in Schedule of Activities (SoA Table 1). |
| Safety Review Committee | A Safety Review Committee (SRC) consisting of investigators/sub-investigators, the medical monitor, and the Sponsor. The SRC will review relevant safety data and make recommendations regarding (a) safety profile of the first subject for continued enrollment within a cohort, dose-escalation to the next cohort. (b) safety monitoring procedures; and (c) any other modifications to the protocol that may be necessary to protect subject safety or support the objectives of the trial. |

TABLE 1

Schedule of Activities (SoA)

| Study Visit | Before First Tx (Screening) | Before Each Daily Tx | 20 min after start of Tx | After EOI (an hour to two hours after) | 8 hours After EOI | 3 days after last Tx and/or 24 hours prior to discharge | 30 day +/−3 days |
|---|---|---|---|---|---|---|---|
| Informed Consent | X | | | | | | Follow-up Call |
| Demographics | X | | | | | | |
| Inclusion/Exclusion | X | | | | | | |
| Medical history | X | | | | | | |
| Brief Physical Exam | X | X | | X | X | X | |
| Vital Signs | X | X | X | X | X | X | |
| Q 5 minutes during infusion then proceed with SOC in the ICU | | | | | | | |
| Blood Sample; COVID-19 | X | | | | | | |
| Blood Cytokine Levels | X | X | | X | | X | |
| Blood Lymphocyte Subsets (Research samples) | X | X | | | | X | |
| CBC with differential | X | X | | X | | | |
| C-Reactive Protein, D-dimer | X | X | | X | X | X | |
| Ferritin | X | X | | X | X | X | |
| Von Willebrand Factor | X | X | | X | X | X | |
| Factor VIII | X | X | | X | X | X | |
| PT(INR), PTT, Fibrinogen | X | X | X | X | | | |
| Chem7 panel (renal panel) | | X | | X | | X | |
| Hepatic Function panel | X | X | | X | | X | |
| Concomitant Meds | X | X | X | X | | X | |
| Adverse Events | | X | X | X | X | X | |

1 Vital signs to include temperature, pulse oxygen, respirations, blood pressure, pulse, cardiac rhythm (as per cardiac monitor)
2 Minimum of q2 hours vital signs (blood pressure, oxygen, pulse, respiratory rate and brief nursing assessment).
3 EOI: end of infusion
4 Within 24 hours of First Tx
5 Brief physical exam includes a cardiac, lung, abdominal and extremity exam with examination of IV access site, plus any other examination deemed necessary by the treating providers.

Introduction Study Rationale

One of the identified causes of death in the most severe cases of SARS-CoV-2 infections, or COVID-19, is hypercytokinemia, also known as a cytokine storm. In the most severe cases acute lung injury and acute respiratory distress syndrome (ARDS), are seen; each associated with hypercytokinemia. In addition, multi-organ failure involving heart, liver and kidneys occurs (Huang et al 2020).

Increased plasma concentrations of the cytokines TNFα, IL-1β, IL-2, IL-7, G-CSF, GM-CSF, MCP-1, MIP-1α, and IFNγ are being reported in severe COVID-19 subjects (Chau et al 2020). T cells that concomitantly produce IFNγ and GM-CSF are reported in effected tissues. Th40 cells are a subset of conventional CD4 T cells that express the CD40 receptor. Th40 cells are highly pro-inflammatory, producing each of the cytokines described during hypercytokinemia. Th40 cells transmigrate into various tissues including lung, heart, liver, and brain during trauma including models of infection.

CD40 is a proven *nexus* for inflammatory cytokine induction. CD40 engagement with its ligand, CD154, leads to large scale production of IL-1a, IL-1β, IL-2, IL-6, IL-17a, IL-21, IL-22, TNFα, GM-CSF and IFNγ. CD154 is expressed on T cells, some antigen presenting cells and on platelets, and in soluble form. Research has demonstrated that Th40 cells express pro-inflammatory cytokines that drive auto-inflammation in both type-1 diabetes and multiple sclerosis (Vaitaitis et al 2019; Vaitaitis et al 2017; Vaitaitis et al 2014; Wagner et al 1994; Alderson et al 1993). Moreover, additional research suggests that SARS-like viral particles may induce CD40 expression on dendritic cells (Bai et al 2008). Controlling the CD40/CD154 mediated signals on T cells, but also on monocytes and macrophages, could disrupt hypercytokinemia and tissue migration of culprit cells during an infectious disease like COVID-19. A crucial question is how to inhibit the CD40/CD154 interaction.

It is proposed that during severe cases of COVID-199, the CD40/CD154 interaction promote hypercytokinemia. The investigational drug, OPT101, is a small peptide derived directly from the CD154 protein sequence that has proven to be highly successful in controlling the autoimmune diseases type I diabetes and multiple sclerosis (Vaitaitis et al 2014; Vaitaitis et al 2019). These diseases experience elevated levels of inflammatory cytokines including IL-1β, TNFα, IFNγ, GM-CSF and IL-6 (Abrahamian et al 2007; de Souza Bastos et al 2016; Wen et al 2006; Siebert et al 2008). When CD40/CD154 interaction was inhibited by OPT101, inflammatory cytokines were substantially and significantly reduced (Vaitaitis et al 2014). This suggests that controlling CD40/CD154 interaction could control hypercytokinemia in COVID-19 patients.

Nonclinical Toxicology

In a preliminary toxicity study rats and dogs were given a single dose of OPT 101 as an IV bolus. Rats dosed at 50 or 100 mg/kg by bolus IV injection did not tolerate the treatment due to the mortality of two rats, and adverse clinical signs. When OPT101 was administered to beagle dogs at 50 or 100 mg/kg by bolus IV injection OPT101 was not tolerated due to adverse clinical signs, including prostration, slight salivation, decreased activities, purple or red skin colored in the abdomen ventral, lateral ears or conjunctiva(s), lips, or periorbital, soft stool, medium food-like, red/brown, or small and frothy vomitus, increased respiratory rate, and labored breathing. Clinical pathology effects included increases in leukocyte count, erythrocyte and platelet counts. There was a notable increase of prothrombin time (increase 288%) and slight decrease of fibrinogen (down to 32%).

There were no increases in serum C5b-9 complement levels for either 50 or 100 mg/kg dose levels, suggesting lack of complement activation. There were notable increases of alanine aminotransferase, aspartate aminotransferase, alkaline phosphatase, γ-glutamyltransferase, urea, creatinine, calcium, phosphorus, total bilirubin, and creatine kinase, and a decrease of potassium for one at 50 and 100 mg/kg by IV injection compared with pretest values. These effects were considered to be adverse at 100 mg/kg, however, no liver or kidney lesions were seen at histopathology evaluation Due to these adverse effects in the rats and dogs after a bolus IV injection, the administration of OPT101 was changed to IV infusion over 30 minutes for the definitive GLP toxicity studies. Rats and dogs were treated once a week for 8-weeks, by 30-minute IV infusions. The PK of OPT101 was also determined following the first and last dose in each study. Doses of 10, 100 or 200 mg/kg/dose in rats were well tolerated and did not result in any adverse effects. The no observable adverse effect level (NOAEL) for OPT101 was considered to be the 200 mg/kg level. Doses of 10, 100, or 400 mg/kg/dose in dogs were well tolerated. The only effects observed were infusion reactions in all treated animals. Due to the incidence and severity of the infusion reactions, the clinical signs were considered adverse at 100 and 400 mg/kg, but because of the lower incidence and severity at 10 mg/kg, the effects at the 10 mg/kg were considered non-adverse. Plasma drug levels increased with increasing dose and there was no marked drug accumulation over the 8-week study.

The clinical signs seen in the rat and dog studies were consistent with a release of histamine and other immune mediators. To test this, rats were given a single bolus IV dose of OPT101 at 12.5 mg/kg of OPT101 The treatment resulted in clinical observation consistent with a histamine reaction, and serum histamine levels were increased significantly 10-minutes post-treatment. At 1-hour post-treatment there was no decreases in serum C3 levels (as measured by conversion to human SC5b-9), suggesting no complement activation, and no changes in serum IFN-γ, TNF-α, IL-10, IL-4, IL-5, IL-6, IL-10, or IL-13 levels. There was a 1.6-fold increase in serum in one chemokine (KC/GRO (CXCL1)).

Since some of the clinical signs were consistent with a drop in blood pressure, a single dose dog study was done, giving doses of 0.3, 1 or 100 mg/kg by a 30-minute IV infusion, and focused on cardiovascular effects. There was no OPT101-related body weight, food consumption, body temperature, respiratory rate and coagulation changes. However, the dogs dosed at 100 mg/kg showed significantly elevated serum levels of histamine at 5 and 30 minutes after start of infusion. Apparent histamine related clinical observations included salivation, vomitus, incontinence, discolored skin, swelling and rash at both 1 and 100 mg/kg. The 100 mg/kg group had much more severe clinical observations compared to 1 mg/kg. These effects were associated with decreases in blood pressure and heart rate for the dogs treated with 100 mg/kg. The blood pressure and heart rate returned to normal by 1 hour after end of infusion. There were no clinical observations or physiological changes seen with the 0.3 mg/kg group, so 0.3 mg/kg was considered a no observable effect level (NOEL).

It has been shown that using an anti-CD154 monoclonal therapeutic approach to interfere with the CD40-CD154 interaction there was efficacy in animal models, but in the clinical trial of one of the monoclonal antibodies there was binding to platelets resulting in emboli. Therefore, the clinical trials were halted (Kawai et al 2000, abstract). To determine if OPT101 has similar effects as the monoclonal antibody, an in vitro study was done with human platelets to determine if OPT101 would affect platelet aggregation, as measured by light transmission aggregometry. Platelet aggregation induced with adenosine diphosphate or collagen were not affected when treated with OPT101 at 0.1, 0.3, 3 or 30 μg/mL. In addition, no spontaneous platelet aggregation was observed in samples treated with OPT101 at 30 μg/mL. Therefore, OPT101 had no impact on human platelet aggregation in vitro. Importantly, there was no evidence of thromboemboli in rats and dogs in the 8-week toxicology studies.

There was clear difference between the infusion reactions seen in the rats and dogs, and IgE-mediated anaphylaxis or other antigen-dependent hypersensitivity. IgE/antigen-dependent degranulation of mast cells is associated with a sustained release of larger and more heterogeneously shaped granule structures, whereas peptide-activated mast cells rapidly secrete small and relatively spherical granule structures (Gaudenzio 2016). This results in a more sustained, severe response with immunologic IgE-mediated anaphylactic reactions compared to the peptide infusion reaction (Bochner 1990; Lawrence et al 2017; Lu et al 2017). In the animal studies, the clinical signs and release of histamine was very transient. In addition, the infusion reactions were also elicited by a scrambled version of OPT101 (same amino acids but in a different sequence), showing the reaction was not OPT101-dependent. The non-immunologic infusion reactions have been shown to be mediated by complement activation as well as release of histamine and other mediators (Simons 2014). There was no evidence of complement activation in the animal studies.

Other peptides have been shown to cause infusion reactions. For example, the FDA-approved peptide drug icatibant causes a reaction due to histamine release that is quickly reversed after end of infusion, similar to OPT101 (NDA 022150). Except for the infusion reactions, and related effect on clinical pathology, there were no other adverse effects seen in the rat and dog 8-week GLP toxicity studies.

OPT101 was negative in the standard reverse bacterial mutation assay (Ames assay).

Risk Assessment

Anticipated Adverse Events

Animal toxicity studies have shown transient histamine-induced infusion reactions which may manifest as some of the following:
Pyrexia
Chills
Flushing
Hypotension
Dyspnea
Wheezing
Back pain
Abdominal pain
Urticaria

Benefit Assessment

There are potential direct benefits to the patient in the study as OPT101 may reduce the hypercytokinemia resulting from the SARS-CoV-2 infection.
Overall Benefit: Risk Conclusion Since no approved alternative therapies exist for COVID-19, and COVID-19 has been associated with a high risk of mortality, the probable risk of using the OPT101 Infusion therapy is deemed to be no greater than the probable risk from the disease.

The concept of risk is generally understood to refer to the combination of the probability and magnitude of some future harm. According to this understanding, risks are considered "high" or "low" depending on whether they are more (or less) likely to occur, and whether the harm is more (or less) serious. This study presents minimal risk as the probability and magnitude of harm or discomfort anticipated in the research are not greater in and of itself than those encountered with the COVID-19 disease. For additional information on risk, see the IB.

Study Design

Rationale for Study Design

This first-in-human, Phase 1 is non-randomized, open label, sequential ascending dose study in subjects >18 years old. A total of up to 12 patients will be dosed. All subjects will receive a total of 8, one per day treatments via a 30-minute slow infusion. For the first cohort (3 subjects), the dose will escalate after 2 days of treatment with 4 escalating doses being administered over the course of treatment (up to 8 days). The planned dose levels are 0.5, 1.0, 2.0 and 4.0 mg/kg. Safety and tolerability, and immunological variables will be assessed at each dose for this cohort, and escalation to the next highest dose will occur only if no DLT is observed. If dose limiting toxicity (DLT) is observed for any dose level, an intermediate dose level between the dose level that exceeds the maximum tolerated dose (MTD) and the previous defined dose level may be used for the remainder of infusions for all patients. Infusion reactions were seen in the nonclinical toxicity studies. All patients will be in ICU-level care, equipped to treat allergic reactions, including continuous vital sign monitoring. MTD is defined as a dose at which less than 33% of subjects have a DLT during the first 2 days of the treatment, regardless if the IP is considered responsible.

Subjects will be initially selected for the study based upon their medical histories and laboratory studies obtained prior to the study, according to the inclusion and exclusion criteria enumerated in the protocol. During the subject recruitment, the investigator will explain the study in detail to the patient or their representative (e.g. power of attorney) and provide a copy of the informed consent to the subject for review. If the patient agrees to participate, the IRB approved consent form will be signed. Each patient will receive a copy of the signed consent form. When consent is obtained from a legally authorized representative, a subject's incapacity to consent will first be verified and documented by two physicians, one of whom will be independent of the study team for patients who are unconscious or have documented diagnosis of delirium. In the case of conscious, non-delirious patients, documentation of incapacity to consent will include evaluation by a psychiatrist or psychologist.

Once patients are identified and consented, each patient in the first cohort will receive 1 infusion treatment that will be performed with 0.5 mg/kg for 2 days. Patients will receive 1 thirty (30) minute long infusion of peptide therapy daily until the patient is showing signs of improvement with laboratory markers and or improved shortness of breath, fever and cough. If no safety concerns are raised, the patient will receive 1 infusion treatment with 1 mg/kg of peptide daily for an additional 2 days. If no dose limiting toxicity is observed, the dose will be raised again to 2 mg/kg and 4 mg/kg for the remaining 4 days (2 days at each dose).

Safety data from the lower dose will be reviewed by the PI before patients receive the next higher dose. Safety, tolerability, immunological, and clinical effects will be assessed up to the 8 total days of infusion.

Patients will be followed for safety, immunological, and clinical assessments for 3 days after the last (up to Day 8) treatment. An additional cytokine assessment will be performed the day prior to discharge along with vital signs. Follow up via call or text with all patients will occur at 30 days post last day of treatment if discharge has already occurred. Patients experiencing immunological and/or clinical effects may be followed for longer, until the immunological or clinical variable returns to baseline levels.

The starting dose of 0.5 mg/kg was calculated from 1/10 the 10 mg/kg NOAEL in the dog toxicity study, converted to the human dose on a mg/m2 basis.

Justification for Use

COVID-19 viral infection is associated with a high case mortality. Currently, there are no documented specific therapies for COVID-19.

End of Study Definition

A patient is considered to have completed the study if they have completed all phases of the study as shown in the SoA, Table 1, Study Procedure Frequency and Timing Overview. The end of the study is defined as 3 days after completion of the last treatment.

Patients will participate in the study for up to eight days for active peptide therapy, with last assessments performed 3 days after the last infusion. A 30 day follow up will occur with cytokine panel and vitals performed the day before discharge from the ICU as applicable. If the patient has been discharged prior to the 30 days, a follow up via call or text will be completed.

Study Population 5.4.1 Inclusion Criteria

Patients are eligible to be included in the study only if all of the following criteria apply:
1. Laboratory confirmation of COVID-19 infection by PCR
2. Demonstration of cytokine release syndrome. Signs of cytokine release syndrome defined as ANY of the following:
   serum ferritin concentration >1000 mcg/L and rising since last 24 h
   single ferritin above 2000 mcg/L in patients requiring immediate high flow oxygen device or mechanical ventilation
   lymphopenia defined as <800 lymphocytes/microliter) and two of the following extra criteria
   Ferritin >700 mcg/L and rising since last 24 h
   increased LDH (above 300 IU/L) and rising last 24 h
   D-Dimers >1000 ng/mL and rising since last 24 h
   CRP above 70 mg/L and rising since last 24 h and absence of bacterial infection
     if three of the above are present at admission, no need to document 24 h rise
3. COVID-19 with the following disease characteristics:
   i. Early acute lung injury (ALI)/early acute respiratory distress syndrome (ARDS).
   ii. Severe disease, defined as:
     dyspnea,
     respiratory frequency ≥30/min,
     blood oxygen saturation ≤93%,
     partial pressure of arterial oxygen to fraction of inspired oxygen ratio of <300, and/or
     lung infiltrates >50%.
   iii. Life-threatening disease, defined as:
     a. respiratory failure,
     b. septic shock, and/or
     c. multiple organ dysfunction or failure.
   Admission to the ICU.
   Stable blood pressure not requiring vasopressors initially.
   Informed consent from the patient or legal representative using the associated Patient
   Informed Consent form must be completed.
   Male or female aged 2:18 years on the day of signing informed consent 5.4.2 Exclusion Criteria Patients are excluded from the study if any of the following criteria apply:
  Patients with a history of venous and arterial thromboembolic events including, but not limited to, the following: deep venous thrombosis, pulmonary embolism, myocardial infarction, stroke, transient ischemic attack, or arterial insufficiency causing digital gangrene should be excluded. In addition, patients with an already known increase in Von Willebrand Factor or Factor IV as can be seen in COVID-19 infections. Patients with a prior history of abnormal prothrombotic laboratories such as congenital or inherited deficiency of antithrombin III, protein C, protein S, or confirmed diagnosis of antiphospholipid syndrome should also be excluded
  Known pre-existing non-COVID-19 related hypercoagulability or other coagulopathy.
  Patients who are already intubated prior to starting peptide therapy (peptide therapy may be continued if patient is intubated after enrollment)
  Biopsy proven cancer not in remission
  Worsening hemodynamic instability
  History of hypersensitivity to antihistamines
  Is pregnant
  Participation in another competing investigational drug, investigational product or vaccine trial
  Advance directive indicating no desire for heroic measures
  Voluntary refusal of the patient or the designated legal representative 5.5 Enrollment Failures A minimal amount of screen failure data will be recorded to ensure transparent reporting of screen failure patients, to meet publishing requirements and to respond to queries from regulatory authorities. The information to be recorded on screen failure patients will include but not be limited to demography, eligibility criteria, and any adverse events.

5.6 Study Intervention

| Intervention Name | OPT101 |
| --- | --- |
| Type | Peptide |
| Use | OPT101 is indicated for use in the Treatment of Cytokine Release Syndrome in COVID-19 Patients |
| Manufacturer | University of Iowa Pharmacy - College of Pharmacy |
| Packaging and Distribution | TBD |
| Storage | Frozen at −20° C. |
| Pharmacy Manual | Pharmacy Manual will be provided to each site for IP preparation |

5.7 Study Intervention Compliance

If there are any deviations from the planned procedures, these will be recorded in the CRF.

5.8 Concomitant Therapy

For this protocol, a prescription medication is defined as a medication that can be prescribed only by a properly authorized/licensed clinician. Medications to be reported in the eCRF are concomitant prescription medications. Patients will be allowed to remain on their routine medications throughout the active study period unless prohibited in exclusion criteria. Prohibited therapies include:
  Any types of thromboembolic treatment prior to COVID-19 hospitalization 5.9 Patient Discontinuation/Withdrawal The patient may withdraw from the study at any time at his/her own request or may be withdrawn at any time at the discretion of the investigator for safety, behavioral, compliance, or administrative reasons. This is expected to be uncommon.

At the time of discontinuing from the study, if possible, an early discontinuation visit should be conducted, as shown in the SoA. See SoA for data to be collected at the time of study discontinuation and follow-up and for any further evaluations that need to be completed. The patient will be permanently discontinued both from the study intervention and from the study at that time. If a patient withdraws from the study, he/she may request destruction of any samples taken and not tested, and the investigator must document this in the site study records.

5.10 Study Assessments and Procedures

Study procedures and their timing are summarized in the Schedule of Activities (SoA). Adherence to the study design requirements, including those specified in the SoA, is essential and required for study conduct. All evaluations must be completed and reviewed to confirm that potential patients meet all eligibility criteria.

A screening log will be maintained to record details of all patients screened and to confirm eligibility or record reasons for screening failure or early termination, as applicable. Procedures conducted as part of the patient's routine clinical management (e.g., blood count) and obtained before signing of the ICF may be utilized for baseline purposes provided the procedures met the protocol-specified criteria and were performed within the time frame defined in the SoA.

5.10.1 Vital Signs

To be measured and recorded on the treatment log sheet every 5 minutes during treatment or more often if symptoms so indicate. Vital signs will include blood pressure, heart rate, respiratory rate and temperature. If a clinically significant abnormality is found prior to, during or immediately after infusion of OPT101, during the study, and/or at any of the follow-up visits, or if the investigator feels that there has been a clinically significant change from screening/baseline, it should be recorded as an adverse event and the study patient will be followed until the vital sign has normalized or stabilized.

5.11 Safety Assessments

Planned time points for all safety assessments are provided in SoA in Section 3.

5.11.1 Laboratory

The following laboratory tests will be done during the study:

| COVID-19 Test | CBC with differential |
|---|---|
| CD3+, CD4+, CD45RA+, CD45RO+, CD8+ and CD19+ lymphocytes, and NK cells (research) | PT (INR), PTT, Fibrinogen, Glucose, Von Willebrand's Factor, Factor VIII |
| C-Reactive Protein, D-dimer | Ferritin |
| Blood cytokine levels, specifically, IL-1β, IL-6, TNFα, IFN-γ, IL-2, IL-17A, , IL-12, IL-4, IL-10, IL-2rec, IL-5, IL-8 (research) | Serum pregnancy test (if applicable) |
| Hepatic function panel (Chem7 panel) | |

Any value outside the normal range will be flagged for the attention of the investigator or designee at the site. The investigator or designee will indicate whether the value is of clinical significance. If the result of any test (or repeat test, if done) from the samples taken during the screening is indicated as clinically significant, the study patient will NOT be allowed into the study without permission of the OP-T LLC Medical Monitor.

Additional testing during the study may be done if medically indicated. If a clinically significant abnormality is found in the samples taken after dosing, during the study, and/or at the follow-up visit, it should be recorded as an adverse event and the study patient will be followed until the test(s) has (have) normalized or stabilized.

5.11.2 Schedule of Assessments

A detailed schedule of assessments is provided in SoA.

5.11.2.1 Before Treatment

The patient will be assessed for study participation based on the inclusion and exclusion criteria. During this period, study procedures will be explained in detail by study staff, informed consent will be obtained, fully executed with copy provided to the patient or Legally Authorized Representative (LAR). The following activities will be performed:

Identify appropriate patients via inclusion/exclusion criteria;

Fully execute informed consent;

Begin adverse event/concomitant medication monitoring;

Demographics: race, ethnicity, sex, date of birth;

Physical exam: noting all abnormal findings

Vital Signs; temperature, pulse oxygen, respiration, blood pressure, pulse, cardiac rhythm (as per cardiac monitor)

Serum Pregnancy (if applicable);

Collect blood sample for assessment of baseline levels of COVID-19 virus and baseline labs immediately prior to initiating OPT101 treatment;

Consequently, the clinical response to any administered medications should be monitored closely to determine if increasing the dose may be warranted;

Place OPT101 IV for infusion if one is not already in place

Prepare Investigational product per pharmacy manual

5.12 Study Treatments Administered

The investigational product, OPT101, will be provided as a sterile solution in 10 mM acetate buffer, in 5% glucose, in water, pH 5.5, 5 mL at 20 mg/mL, 100 mg/vial. On the same day as the investigational product administration, the product will be diluted in saline to a volume of 50 mL to the concentration of OPT101 required for each dose level, and administered by intravenous (IV) infusion over 30 minutes.

The table below (Table 2) provides an example of dose preparation procedure for all 5 doses to be used in this trial. The dose will be adjusted based on body weight (kg) and is provided below for a subject with a body weight of 70 kg. Calculations and final formulation must be documented on the appropriate case report form (CRF).

TABLE 2

Example Dosing Preparation Procedure
for OPT101 based on bodyweight

| OPT101 - Example dosing procedure | Vials - 100 mg/vial in 5 mL, 20 mg/mL |
| --- | --- |
| body weight (kg) | 70 |
| total dose volume (mL) | 50 dose volume constant across doses |
| infusion time (min) | 30 infusion rate constant across doses |
| vial concentration (mg/mL) | 20 100 mg in 5 mL |

| mg/kg | body wt (kg) | mg/dose of OPT101 | dose vol (mL) | desired final concentration (mg/mL) | mL from 20 mg/mL vial |
| --- | --- | --- | --- | --- | --- |
| 0.5 | 70 | 11.2 | 50 | 0.22 | 0.56 |
| 1 | 70 | 29.4 | 50 | 0.59 | 1.47 |
| 2 | 70 | 77 | 50 | 1.54 | 3.85 |
| 4 | 70 | 196 | 50 | 8.92 | 9.8 |

5.13 OPT101 Treatment Instructions

The IP infusion will be conducted unblinded to the dose level, and study staff (not performing any study related procedures) will be unblinded to prepare the IP for infusion. The IP is to remain frozen in −20° C. freezer until preparation for infusion. Detailed instructions on the preparation and administration of the drug are provided in the Infusion Dose Preparation Instructions that will be provided by the Sponsor. If infusion reactions are observed anytime during the study for a subject, pre-medication with an antihistamine should occur for that subject prior to additional dosing.

5.14 Treatment Assignment

Each patient will be assigned a subject ID and will only be identified by this unique ID. If, as an exception, it is necessary for safety or regulatory reasons to identify the subject, all parties will be bound to keep this information confidential. The subject ID will be used for patient identification throughout the study. The numbers will be assigned sequentially. The subject ID should be used on all study documents relating to the subject from screening and throughout the study.

5.15 Dose Modification

The investigational product will be prepared by an unblinded study staff member and administered by the Investigator or authorized study site staff. All subjects will be given the assigned dose level without dose modification. The 30-minute infusion may be terminated if AE are observed.

5.15.1 Stopping Criteria

5.15.1.1 Dose Escalation Stopping Criteria

Data for all subjects will be reviewed by the Safety Review Committee (SRC) before dose escalation or de-escalation, or at any time point as needed when safety concerns arise. In addition to the SRC oversight and recommendations, the following stopping criteria will be implemented:

Subject stopping criteria: If a subject experiences an AE that is deemed by the clinical site Principal Investigator to be at least "possibly" drug-related and is Grade 2:3 in severity (using the Common Terminology Criteria for Adverse Events (CTCAE v 5), that subject will be withdrawn from dosing, return for all scheduled evaluation visits, and be followed until the AE resolves or stabilizes.

Cohort stopping criteria: If 33% (2 of the first 6 patients), at any time experience any of the following events not clearly due to the underlying disease or extraneous causes and is deemed by the clinical center Principal Investigator to be at least "possibly" drug-related and Grade 2:3 in severity by CTCAE. Dosing in that cohort, as well as further dose escalation, will be suspended within that study arm. Events such as:

An SAE occurs that is not clearly unrelated to IP

Any Grade 2: 3 (this may exclude Grade 3 nausea/vomiting or diarrhea for <72 hours with adequate supportive care, Grade 3 fatigue for >1 week, Grade 2: 3 uncomplicated electrolyte abnormality that resolves spontaneously or in response to conventional medical intervention, and Grade 2: 3 abnormalities in laboratories within a few standard deviations)

Increases in Von Willebrand Factor from baseline

Increases in Factor VIII from baseline

Placement on a ventilator

Hy's law cases

Any other event that is deemed by the Investigator or Sponsor to pose an unacceptable risk to subjects as a result of dose escalation Grade and severity of AEs will be assessed as defined by the National Cancer Institute—Common Terminology Criteria for Adverse Events (CTCAE) Version 5.0.

5.15.2 Infusion-Related Reactions

Subjects will be monitored for signs and symptoms of infusion-related reactions, including pyrexia, chills, flushing, hypotension, dyspnea, wheezing, back pain, abdominal pain, and urticaria. Interrupt or slow the rate of infusion for mild (Grade 1) or moderate (Grade 2) infusion-related reactions.

Permanently discontinue OPT101 for severe (Grade 3) or life-threatening (Grade infusion-related reactions.

Treatment recommendations are provided below and may be modified based on local treatment standards and guidelines, as appropriate:

For Grade I symptoms (Mild reaction; infusion interruption not indicated; intervention not indicated):

Remain at bedside and monitor subject until recovery from symptoms. The following prophylactic pre-medications are recommended for future infusions: diphenhydramine 50 mg IV (or equivalent) and/or acetaminophen/paracetamol 325 to 1000 mg PO at least 30 minutes before additional investigational product administrations.

For Grade 2 symptoms ((urticaria or erythema; stable vital signs; moderate reaction requires therapy or infusion interruption but responds promptly to symptomatic treatment (e.g., antihistamines, non-steroidal anti-inflammatory drugs, prophylactic medications indicated for <24 hours)).

Treat the subject with diphenhydramine 50 mg IV (or equivalent) and/or acetaminophen/paracetamol 325 to 1000 mg PO; remain at bedside and monitor subject until resolution of symptoms.

For future infusions, the following prophylactic premedications are recommended:

Diphenhydramine 50 mg (or equivalent) and/or acetaminophen/paracetamol 325 to 1000 mg should be administered at least 30 minutes before study drug infusions.

If necessary, corticosteroids (up to 25 mg of SoluCortef or equivalent) may be used.

For Grade 3 or 4 symptoms (hypotension, hypoxia, unstable vitals; severe reaction, Grade 3: prolonged (i.e., not rapidly responsive to symptomatic medication and/or brief interruption of infusion); recurrence of symptoms following initial improvement; hospitalization indicated for other clinical sequelae (e.g., renal impairment, pulmonary infiltrates). Life-threatening, Grade 4: pressor or ventilatory support indicated).

Immediately discontinue infusion of the study drug. Begin an IV infusion of normal saline and treat the subject as follows: Recommend bronchodilators, epinephrine 0.2 to 1 mg of a 1:1000 solution for subcutaneous (SC) administration or 0.1 to 0.25 mg of a 1:10,000 solution injected slowly for IV administration, and/or diphenhydramine 50 mg IV with methylprednisolone 100 mg IV (or equivalent), as needed. Subject should be monitored until the Investigator is comfortable that the symptoms will not recur.

All study drug will be permanently discontinued. Investigators should follow their institutional guidelines for the treatment of anaphylaxis. Remain at bedside and monitor subject until recovery of the symptoms.

In case of late-occurring hypersensitivity symptoms (e.g., appearance of a localized or generalized pruritus within 1 week after treatment), symptomatic treatment may be given (e.g., oral antihistamine or corticosteroids).

5.15.3 During Treatment Evaluations

Continue to monitor adverse event/concomitant medication.

The entire OPT101 infusion treatment will be attended and continuously monitored by a designated care-giver.

The following parameters will be recorded on the treatment log sheet; Vital signs every 5 minutes until the treatment is terminated with one last battery of parameters being recorded just prior to treatment termination.

Blood samples collected at the time points listed in SOA.

5.15.4 After Treatment

Collect after treatment blood tests
Vitals signs
Concomitant Medications
Adverse Events

Assessment of Safety

6.1 Adverse Event (AE)

An AE is any untoward medical occurrence in a subject receiving the study drug and which does not necessarily have a causal relationship with this treatment. For this protocol, the definition of AE also includes worsening of any pre-existing medical condition. An AE can therefore be any unfavorable and unintended or worsening sign (including an abnormal laboratory finding), symptom, or disease temporally associated with the use of OPT101, whether related to use of the OPT101. Abnormal laboratory findings without clinical significance (based on the Principal Investigator's judgment) should not be recorded as AEs. But laboratory value changes that require therapy or adjustment in prior therapy are considered AEs. From the time the subject signs the informed consent form through the Follow-Up Visit all AEs must be recorded in the subject medical record and AE CRF.

AEs will be assessed according to the CTCAE version 5.0, which has been harmonized to MedDRA (Medical Dictionary for Regulatory Activities) coding. If CTCAE grading does not exist for an AE, the severity of the AE will be graded as mild (1), moderate (2), severe (3), life-threatening (4), or fatal (5). Attribution of AEs will be indicated as follows:

Definite: The AE is clearly related to the OPT101

Probably: The AE is likely related to the OPT101 Possible: The AE may be related to the OPT101

Unlikely: The AE is doubtfully related to the OPT101

Unrelated: The AE is clearly NOT related to the OPT101

6.1.1 Serious Adverse Event

An AE or suspected adverse reaction is considered "serious" if in the opinion of a skilled person it results in any of the following outcomes:

Death

Life-threatening adverse event

A medically significant condition (defined as an event that compromises subject safety or may require medical or surgical intervention to prevent one of the three outcomes above).

Requires inpatient hospitalization or prolongation of existing hospitalization

Results in persistent or significant incapacity or substantial disruption to conduct normal life functions Results in a congenital anomaly/birth defect.

6.2 Adverse Event by Severity or Intensity

AE severity will be graded according to the National Cancer Institute Common Terminology Criteria for Adverse Events (NCI CTCAE v5.0) available at ctep.cancer.gov/protocoldevelopment/electronic_applications/docs/CTCAE_v5_Quick_Referenc e_8.5x11.pdf. The grading scale is illustrated in Table 3. The severity of the AE should be recorded in the appropriate section of the AE page of the eCRF.

TABLE 3

| Definitions of Adverse Events Severity | |
|---|---|
| Grade 1 (Mild) | Mild; asymptomatic observed or mild symptoms (such as an asymptomatic self- limited rash); clinical or diagnostic observation's only; intervention not indicated. |
| Grade 2 (Moderate) | Moderate; minimal, local or noninvasive intervention indicated; limiting age-appropriate instrumental ADL*. |
| Grade 3 (Severe) | Severe or medically significant but not immediately life-threatening; hospitalization or prolongation of hospitalization indicated; disabling; |

TABLE 3-continued

Definitions of Adverse Events Severity

| | |
|---|---|
| Grade 4 (Life- Threatening) | Life-threatening consequences: urgent intervention indicated. |
| Grade 5 (Death) | Death related to AE |

Based on the Common Terminology Criteria for Adverse Events v5.0 (CTCAE).
*Instrumental ADL refer to preparing meals, shopping for groceries or clothes, using the telephone, managing money, etc.
**Self-care ADL refer to bathing, dressing and undressing, feeding self, using the toilet, taking medications, and not bedridden.
ADL = activities of daily living

6.3 Relationship Between Adverse Events (AEs) and Investigational Product (IP)

The causality of each AE will be assessed and classified. The determination of the relationship (if any) between the AE and the IP will be made using the guidelines in Table 4.

TABLE 4

Guidelines for Determining the Relationship (if any) Between Adverse Event and the Investigational product

| | |
|---|---|
| Definite: | This causal relationship is assigned if the AE starts a reasonable time after the administration of investigational product, stops/improves when the investigational product is stopped, and could reasonably be explained by known characteristics of the |
| Probable: | This causal relationship is assigned when the AE starts a reasonable time after the administration of investigational product, stops/improves when the investigational product is stopped, and could not be reasonably explained by known characteristics of the |
| Possible: | This causal relationship is assigned when the AE starts a reasonable time after the administration of investigational product but could be produced by the subject's clinical state or other modes of therapy administered to the subject. |
| Not Related: | This causal relationship is assigned when the time association or the subject's clinical state is such that the investigational product was not likely to have had an association with the observed AE. |

6.4 Physical Examination

Listing of all physical examination assessment will be provided.

6.5 Vital Signs

Vital signs will be recorded as standard of care per institutional guidelines to include temperature, pulse oxygen, respiration, blood pressure, pulse, cardiac rhythm (as per cardiac monitor). Change from baseline values will be presented for each post-baseline assessment.

All vital sign values will be reviewed for clinical significance. Additional vital signs will be obtained when clinically indicated.

6.7 Clinical Laboratory Evaluations (Including Coagulation Tests)

Blood study samples will be collected, processed, and shipped according to the instructions from the site's safety laboratory at the time points indicated in the Schedule of Procedures and Assessments.

6.8 Statistical Considerations

6.8.1 Statistical Analyses

No formal statistical analyses are planned however the following descriptive statistics will be collected and reported:

6.8.2 Demographic and Baseline Characteristics

The number of patients included in each study population will be summarized by treatment group and overall. Demographic and other baseline characteristics, including sex, age, age group, race, height, weight, and baseline values will be summarized by treatment group, for the Safety, and ITT populations, using descriptive statistics.

6.8.3 Safety Analyses

6.8.3.1 Adverse Events

Reported AEs will be summarized by the number of patients reporting the events, as well as by System Organ Class, Preferred Term, severity, seriousness, and relationship to study product. For the summary of AEs by severity, each patient will be counted only once within a System Organ Class or a Preferred Term by using the AEs with the highest intensity within each category for each analysis. For the summary of AEs by relationship to study product, each patient will be counted only once within a System Organ Class or a Preferred Term by using the AEs with the greatest reported relationship within each category. For the summary of AEs by relationship to study product and severity, each patient will be counted only once within a System Organ Class or a Preferred Term by using (1) the greatest reported relationship followed by (2) the highest reported intensity.

All information pertaining to AEs noted during the study will be listed by patient, detailing verbatim, System Organ Class, Preferred Term, start date, stop date, intensity, outcome, and relationship to study product. The AE onset will also be shown relative (in number of days) to the day of study product administration. SAEs will be tabulated by treatment group, relationship to the test article, and a reference to the occurrence of the SAEs to the relative day of treatment start.

6.8.3.2 Clinical Laboratory

Descriptive statistics for clinical laboratory values and changes from Baseline at each assessment time point will be presented by treatment group for each clinical laboratory parameter. Shift tables to summarized change from Baseline to post Baseline visits will also be presented (e.g., normal to high and normal to low). Separate listings of all data for all the laboratory parameters will be provided.

6.8.3.3 Prior and Concomitant Medications

Use of medications as described in Section 5.15, prior to and during the treatment period for the safety population will be coded with the World Health Organization (WHO) Drug Dictionary and listed by patient. Summary of medication classes will also be tabulated using counts and percentages in each treatment group.

6.8.3.4 Physical Examinations

Listings of all physical examination assessments will be provided.

6.8.3.5 Vital Signs

Descriptive statistics will be presented for data related to vital signs (systolic blood pressure diastolic blood pressure, pulse rate and body temperature, pulse oxygen level). Change from baseline values will be presented for each post-baseline assessment.

Shift tables from baseline to each post-baseline visits and to each timepoint describing shifts to abnormality will be provided as well. Only patients with a baseline result and a result at the specified visit for the parameter will be considered.

A listing of all vital sign assessments will be provided. In addition, a listing will be provided for each parameter where a patient had at least one abnormal result.

6.9 Consent Procedures and Documentation

Informed consent is a process that is initiated prior to the individual's agreeing to participate in the study and continues throughout the individual's study participation. Consent forms will be Institutional Review Board (IRB)—approved and the patient will be asked to read and review the document. As part of this procedure, the investigator (or designee) must explain orally and in writing the nature, duration, and purpose of the study, and the action of the investigational product in such a manner that the study patient is aware of the potential risks, inconveniences, or adverse events that may occur. The patient will sign the informed consent document prior to any specific procedures being done for the study. The investigator will not undertake any investigation specifically required for the clinical study until written consent has been obtained. Patients will have the opportunity to carefully review the written consent form and ask questions prior to signing. The patients should have the opportunity to discuss the study with their family or surrogates or think about it prior to agreeing to participate. Patients must be informed that participation is voluntary and that they may withdraw from the study at any time, without prejudice. A copy of the informed consent document will be given to the patients for their records. The informed consent document must be signed and dated; one copy will be handed to the patient, and the investigator will retain the original as part of the clinical study records. The terms of the consent and when it was obtained must also be documented. The rights and welfare of the patients will be protected by emphasizing to them that the quality of their medical care will not be adversely affected if they decline to participate in this study. If a protocol amendment is required, then the informed consent document may need to be revised to reflect the changes to the protocol. If the informed consent document is revised, it must be reviewed and approved by the responsible IRB and signed by all patients subsequently enrolled in the clinical study as well as those currently enrolled in the clinical study.

6.10 Legalized Authorized Representative (LAR)

The LAR means an individual or judicial or other body authorized under applicable law to consent on behalf of a prospective patient to the patient's participation in the procedure(s) involved in the research (45 CFR 46.102(c)). The regulations state that "no investigator may involve a human being as a patient in research covered by this policy unless the investigator has obtained the legally effective informed consent of the patient or the patient's legally authorized representative" (45 CFR 46.116).

The issue as to who can be a LAR is determined by the laws of the jurisdiction in which the research is conducted (e.g., local or state law). Some states have statutes, regulations, or common law that specifically address consent by someone other than the patient for participation in research. Most states have no law specifically addressing the issue of consent in the research context. In these states, law that addresses who is authorized to give consent on behalf of another person to specific medical procedures or generally to medical treatment may be relevant if the research involves those medical procedures or medical treatment. The LAR may be a parent, grandparent, caregiver who has the legal authority to grant consent on behalf of another who has been invited to participate in research. Patients under the age of majority will require parental or other assent.

When the laws of the jurisdiction in which the research is being conducted provide a reasonable basis for authorizing an individual to consent on behalf of a prospective patient to their participation in the research procedure(s), OHRP would consider such an individual to be a LAR as defined by HHS regulations at 45 CFR 46.102(c). IRBs may wish to consult with legal counsel when deciding who can serve as a LAR for patients of proposed research.

As a general matter, if an adult lacks capacity to consent, for example, as a result of trauma, mental retardation, some forms of mental illness, or dementia—whether temporary, progressive, or permanent—only a legally authorized representative for that adult can give consent for participation in the research, unless the requirement to obtain informed consent is waived by the IRB in accordance with the requirements at 45 CFR 46.116(c)(d), or in accordance with the provisions for emergency waiver, which are permitted under the authority of the HHS Secretary at 45 CFR 46.101 (i). Should the patient regain or develop the capacity to consent, then his or her consent must be obtained for any further research, as the consent of the legally authorized representative is no longer valid.

6.11 Electronic (eCRF) Completion

Electronic case report forms (eCRFs) will be utilized as the data capture system in this clinical study. Local laboratories will be used in this study. The data will be entered in the eCRF. Data collection processes and procedures will be reviewed and validated to ensure completeness, accuracy, reliability, and consistency. A complete audit trail will be maintained for all data changes. Within form and cross form consistency checks will be used to identify errors or inconsistencies.

This information will be provided to the respective study sites by means of queries. Queries may also be manually generated upon request by the Site Monitor (CRA) or after manual review of eCRFs.

6.13 Study Discontinuation and Closure

The study may be temporarily suspended or prematurely terminated if there is sufficient reasonable cause. Circumstances that may warrant termination or suspension include, but are not limited to:

Determination of unexpected, significant, or unacceptable risk to participants
Demonstration of efficacy that would warrant stopping
Insufficient compliance to protocol requirements
Data that are not sufficiently complete and/or evaluable
Determination that the primary endpoint has been met
Determination of futility Study may resume once concerns about safety, protocol compliance, and data quality are addressed. If conditions or events suggest a possible hazard to patients if the clinical study continues, then the clinical study may be terminated. Conditions that may warrant termination of the clinical study include, but are not limited to:
discovery of an unexpected, relevant, or unacceptable risk to the patients enrolled in the clinical study;
failure to enroll patients at the required rate.

6.14 Clinical Monitoring

The investigator must prepare and maintain adequate and accurate records of all observations and other data pertinent to the clinical study for each study patient. The investigator will make all appropriate safety assessments on an ongoing basis. All aspects of the study will be carefully monitored with respect to GCP and standard operating procedures (SOPs) as frequently as necessary to ensure compliance with the protocol, accurate data collection, and conformance with applicable government regulations.

7. References

] Abrahamian H, Endler G, Exner M, Mauler H, Raith M, Endler L, Rumpold H, Gerdov M, Mannhalter C, Prager R et al: Association of low-grade inflammation with nephropathy in type 2 diabetic patients: role of elevated CRP-levels and 2 different gene-polymorphisms of proinflammatory cytokines. Exp Clin Endocrinol Diabetes 2007, 115(1):38-41.
Alderson M R, Armitage R J, Tough T W, Strockbine L, Fanslow W C, Spriggs M K: CD40 expression by human monocytes: regulation by cytokines and activation of monocytes by the ligand for CD40. Journal of Experimental Medicine 1993, 178(2):669-674.
Bai B, Hu Q, Hu H, Zhou P, Shi Z, Meng J, Lu B, Huang Y, Mao P, Wang H. Virus-like particles of SARS-like coronavirus formed by membrane proteins from different origins demonstrate stimulating activity in human dendritic cells. PLoS One. 2008 Jul. 16; 3 (7):e2685. doi: 10.1371/journal.pone.0002685.
Bochner B S, Charlesworth E N, Lichtenstein L M et al. Interleukin-1 is released at sites of human cutaneous allergic reactions. J Allergy Clin Immunol. 1990; 86:830-839
Chau V Q, Oliveros E, Mahmood K, Singhvi A, Lala A, Moss N, Gidwani U, Mancini Dl'vl, Pinney S P, Parikh A: The Imperfect Cytoki ne Storm: Severe COVID-19 with ARDS in Patient on Durabl e LVAD Support. 0.14CC Case Rep 2020.
de Souza Bastos A, Graves D T, de Melo Loureiro A P, Junior C R, Corbi S C T, Frizzera F, Scarel-Caminaga R M, Camara N O, Andriankaj a OM, Hiyane M I et al: Diabetes and increased lipid peroxidation are associated with systemic inflammation even in well-controlled patients. J Diabetes Complications 2016, 30(8): 1593-1599.
Gaudenzio N, Sibilano R, Maricha T et al Different activation signals induce distinct mast cell degranulation strategies. J. Clin. Invest 2016; 12: 3981-3998.
Huang C, Wang Y, Li X, Ren L, Zhao J, Hu Y, Zhang L, Fan G, Xu J, Gu X et al: Clinical features of patients infected with 2019 novel coronavirus in Wuhan, China. Lancet 2020, 395(10223):497-506.
Kawai T, Andrews D, Colvin R B, Sachs D H, Cosimi A B. Thromboembolic complications after treatment with monoclonal antibody against CD40 ligand. [abstract] Nat Med. 2000 February; 6(2): 114.
Lawrence M G, Woodfolk J A, Schuyler A J et al. Half-life of IgE in serum and skin: Consequences for anti-IgE therapy in patients with allergic disease. Allergy Clin Immunol. 2017; 139:422-428.
Lu L, Kulka M, Unsworth L D. Peptide-mediated mast cell activation: ligand similarities for receptor recognition and protease-induced regulation. J Leukoc Biol. 2017; 102:237-251.
Siebert J C, Inokuma M, Waid D M, Pennock N D, Vaitaitis G M, Disis M L, Dunne J F, Wagner D H, Jr., Maecker H T: An analytical workflow for investigating cytokine profiles. Cytometry A 2008, 73(4):289-298
Simons F E R, Ardusso L R F, Bilo M B et al. World Allergy Organization Guidelines for the Assessment and Management of Anaphylaxis. WAO Journal 2011; 4:13-37. FIG. 1.1 Simons 2014
Vaitaitis G M, Olmstead M H, Waid D M, Carter J R, Wagner D H, Jr.: A CD40-targeted peptide controls and reverses type 1 diabetes in NOD mice. Diabetologia 2014, 57(11):2366-2373.
Vaitaitis G M, Rihanek M, Alkanani A K, Waid D M, Gottlieb P A, Wagner D H, Type 1 Diabetes TrialNet Study G: Biomarker discovery in pre-Type 1 Diabetes; Th40 cells as a predictive risk factor. J Clin Endocrinol Metab 2019.
Vaitaitis G M, Yussman M G, Wagner D H, Jr.: A CD40 targeting peptide prevents severe symptoms in experimental autoimmune encephalomyelitis. J Neuroimmunol 2019, 332:8-15.
Vaitaitis G M, Yussman M G, Waid D M, Wagner D H, Jr.: Th40 cells (CD4+CD40+ T cells) drive a more severe form of Experimental Autoimmune Encephalomyelitis than conventional CD4 T cells. PLoS One 2017, 12(2): e0172037.
Wagner D H, Jr.: Overlooked Mechanisms in Type 1 Diabetes Etiology: How Unique Costimulatory Molecules Contribute to Diabetogenesis. Front Endocrinol (Lausanne) 2017, 8:208.
Wen Y, Gu J, Li S L, Reddy M A, Natarajan R, Nadler J L: Elevated glucose and diabetes promote interleukin-12 cytokine gene expression in mouse macrophages. Endocrinology 2006, 147(5):2518-2525.

We claim:

1. A method of treating COVID-19, the method comprising administering to a subject having COVID-19 an effective amount of a peptide that alters or modulates the binding or interaction between CD40 complex and CD 154 proteins, wherein the peptide comprises SEQ ID NO: 4.

2. The method of claim 1, wherein the peptide binds to CD40 complex.

3. The method of claim 1, wherein the peptide disrupts or alters the interaction of CD40 complex with CD154 and reduces the number of Th40 cells in the subject.

4. The method of claim 1, wherein the peptide comprises SEQ ID NO: 7.

5. The method of claim 1, wherein administration of the peptide decreases an amount of inflammatory cytokine selected from the group of IL-2, IFNγ, IL-6, TNFα, TGF, and IL-17A, and/or increases an amount of IL-10.

6. The method of claim 1, wherein the peptide comprises a modification selected from phosphorylation, glycosylation, acetylation on the N-terminus and/or amidation on the C-terminus.

7. The method of claim 1, wherein the peptide is linked to a polyethylene glycol (PEG) molecule.

8. The method of claim 1, wherein the peptide is linked to one or more domains of an Fc region of human IgG immunoglobin.

9. The method of claim 8, wherein the Fc region is human IgG hinge, CH2, CH3 region that is fused to at least one of the amino-terminus or carboxyl-terminus of the peptide.

10. The method of claim 1, wherein the peptide is administered to the lungs of the subject.

11. The method of claim 1, wherein the peptide is linked to an epitope tag polypeptide comprising between 6 and 50 amino acid residues.

12. The method of claim 1, wherein the subject is experiencing cytokine release syndrome (CRS) and/or wherein the method treats or reduces the severity of CRS.

13. The method of claim 1, wherein the subject is experiencing acute respiratory distress syndrome (ARDS) and/or wherein the method treats or reduces the severity of ARDS.

14. The method of claim 1, wherein the peptide is constructed by chemical means.

* * * * *

SEQUENCE LISTING

<160> NUMBER OF SEQ ID NOS: 37

<210> SEQ ID NO 1
<211> LENGTH: 260
<212> TYPE: PRT

<213> ORGANISM: Mus musculus

<400> SEQUENCE: 1

```
Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260
```

<210> SEQ ID NO 2
<211> LENGTH: 261
<212> TYPE: PRT
<213> ORGANISM: Homo sapiens

<400> SEQUENCE: 2

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
```

```
                     85                  90                  95
Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
                195                 200                 205

Ala Asn Thr His Ser Ser Ala Lys Pro Cys Gly Gln Gln Ser Ile His
            210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 3
<211> LENGTH: 4
<212> TYPE: PRT
<213> ORGANISM: Mus musculus

<400> SEQUENCE: 3

Lys Gly Tyr Tyr
1

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Ala Lys Lys Gly Tyr Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

Ala Lys Lys Gly Tyr Tyr Thr Met
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide
```

```
<400> SEQUENCE: 6

Ala Glu Lys Gly Tyr Tyr Thr Met
1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 7

Val Leu Gln Trp Ala Lys Lys Gly Tyr Tyr Thr Met Lys Ser Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 8

Val Leu Gln Trp Ala Glu Lys Gly Tyr Tyr Thr Met Ser Asn Asn
1               5                   10                  15

<210> SEQ ID NO 9
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 9

Asn Ala Ala Ser Val Leu Gln Trp Ala Lys Lys Gly Tyr Tyr Thr Met
1               5                   10                  15

Lys Ser Asn Leu Val Met Leu Glu
            20

<210> SEQ ID NO 10
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 10

Ile Ser Gln Ala Val His Ala Ala His Ala Glu Ile Asn Glu Ala Gly
1               5                   10                  15

Arg

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 11

Gly Leu Gln Trp Ala Lys Lys Gly Tyr Tyr Thr Met Lys Ser Asn
1               5                   10                  15

<210> SEQ ID NO 12
<211> LENGTH: 15
```

```
<212> TYPE: PRT
<213> ORGANISM: Artificial Sequence
<220> FEATURE:
<223> OTHER INFORMATION: Synthetic Peptide

<400> SEQUENCE: 12

Val Gly Gln Trp Ala Lys Lys Gly Tyr Tyr Thr Met Lys Ser Asn
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 13

Val Leu Gly Trp Ala Lys Lys Gly Tyr Tyr Thr Met Lys Ser Asn
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 14

Val Leu Gln Gly Ala Lys Lys Gly Tyr Tyr Thr Met Lys Ser Asn
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 15

Val Leu Gln Trp Gly Lys Lys Gly Tyr Tyr Thr Met Lys Ser Asn
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 16

Val Leu Gln Trp Ala Gly Lys Gly Tyr Tyr Thr Met Lys Ser Asn
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 17

Val Leu Gln Trp Ala Lys Gly Gly Tyr Tyr Thr Met Lys Ser Asn
1               5                   10                  15

<210> SEQ ID NO 18
<211> LENGTH: 15
<212> TYPE: PRT
```

```
<213> ORGANISM: Artificial Sequence
<220> FEATURE:
<223> OTHER INFORMATION: Synthetic Peptide

<400> SEQUENCE: 18

Val Leu Gln Trp Ala Lys Lys Gly Gly Tyr Thr Met Lys Ser Asn
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 19

Val Leu Gln Trp Ala Lys Lys Gly Tyr Gly Thr Met Lys Ser Asn
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 20

Val Leu Gln Trp Ala Lys Lys Gly Tyr Tyr Gly Met Lys Ser Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 21

Val Leu Gln Trp Ala Lys Lys Gly Tyr Tyr Thr Gly Lys Ser Asn
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 22

Ile Ser Gln Ala Val His Ala Ala His Ala Glu Ile Asn Glu Ala Gly
1               5                   10                  15

Arg

<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 23

Tyr Val Gln Gly Lys Ala Asn Leu Lys Ser Lys Leu Met Tyr Thr
1               5                   10                  15

<210> SEQ ID NO 24
<211> LENGTH: 10
```

```
<212> TYPE: PRT
<213> ORGANISM: Artificial Sequence
<220> FEATURE:
<223> OTHER INFORMATION: Synthetic Peptide

<400> SEQUENCE: 24

Trp Ala Lys Lys Gly Tyr Tyr Thr Met Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 25

Val Leu Gln Trp Ala Lys Lys Gly Tyr Tyr Thr Met Lys
1               5                   10

<210> SEQ ID NO 26
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 26

Ala Ala Ser Val Leu Gln Trp Ala Lys Lys Gly Tyr Tyr Thr Met Lys
1               5                   10                  15

Ser Asn Leu Val Val Leu Glu Asn
            20

<210> SEQ ID NO 27
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 27

Lys Gly Tyr Tyr Thr Met
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 28

Ala Glu Lys Gly Tyr Tyr
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 29

Ala Lys Lys Gly Tyr Tyr
1               5
```

```
<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 30

Ala Lys Gly Tyr Tyr Thr
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 31

Tyr Lys Asn Val Lys Gln Met Ala Tyr Trp Leu Thr Gly Lys Ser
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Val Leu Arg Trp Ala Pro Lys Gly Tyr Tyr Thr Ile Ser Ser Asn
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic

<400> SEQUENCE: 33

Val Leu Gln Trp Ala Pro Lys Gly Tyr Tyr Thr Ile Ser Ser Asn
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

Val Leu Gln Trp Ala Gln Lys Gly Tyr Tyr Thr Ile Ser Asn Asn
1               5                   10                  15

<210> SEQ ID NO 35
<211> LENGTH: 11
<212> TYPE: PRT
<213> ORGANISM: Artificial Sequence
<220> FEATURE:
<223> OTHER INFORMATION: Synthetic

<400> SEQUENCE: 35

Tyr Gly Arg Lys Lys Arg Arg Gln Arg Arg Arg
1               5                   10

<210> SEQ ID NO 36
```

```
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: X is any amino acid other than Tyr
<222> LOCATION: (1)..(1)

<400> SEQUENCE: 36

Xaa Gly Arg Lys Lys Arg Arg Gln Arg Arg
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic

<400> SEQUENCE: 37

Gly Arg Lys Lys Arg Arg Gln Arg Arg
1               5                   10
```